(12) United States Patent
Lycas

(10) Patent No.: US 10,963,977 B2
(45) Date of Patent: *Mar. 30, 2021

(54) METHOD AND APPARATUS FOR PERSONAL AWARENESS AND GROWTH

(71) Applicant: Geoffrey S. Lycas, Castle Rock, CO (US)

(72) Inventor: Geoffrey S. Lycas, Castle Rock, CO (US)

( * ) Notice: Subject to any disclaimer, the term of this patent is extended or adjusted under 35 U.S.C. 154(b) by 294 days.

This patent is subject to a terminal disclaimer.

(21) Appl. No.: 16/056,649

(22) Filed: Aug. 7, 2018

(65) Prior Publication Data

US 2018/0342027 A1    Nov. 29, 2018

Related U.S. Application Data

(63) Continuation-in-part of application No. 15/429,606, filed on Feb. 10, 2017, now Pat. No. 10,055,802, which is a continuation of application No. 13/896,553, filed on May 17, 2013, now Pat. No. 9,589,475, which is a continuation of application No. 13/538,431, filed on Jun. 29, 2012, now Pat. No. 8,449,300, which is a continuation of application No.

(Continued)

(51) Int. Cl.
| | | |
|---|---|---|
| G09B 7/02 | (2006.01) | |
| G06Q 50/22 | (2018.01) | |
| G06Q 30/02 | (2012.01) | |
| G09B 5/06 | (2006.01) | |
| G09B 5/00 | (2006.01) | |
| G16H 10/60 | (2018.01) | |
| G06F 19/00 | (2018.01) | |
| G09B 19/00 | (2006.01) | |
| G09B 7/00 | (2006.01) | |
| G09B 23/28 | (2006.01) | |
| G09B 7/04 | (2006.01) | |
| G16H 20/70 | (2018.01) | |
| G16H 50/30 | (2018.01) | |

(52) U.S. Cl.
CPC ............ *G06Q 50/22* (2013.01); *G06F 19/00* (2013.01); *G06Q 30/0245* (2013.01); *G06Q 30/0269* (2013.01); *G09B 5/00* (2013.01); *G09B 5/06* (2013.01); *G09B 5/065* (2013.01); *G09B 7/00* (2013.01); *G09B 7/02* (2013.01); *G09B 7/04* (2013.01); *G09B 19/00* (2013.01); *G09B 23/28* (2013.01); *G16H 10/60* (2018.01); *G16H 20/70* (2018.01); *G16H 50/30* (2018.01)

(58) Field of Classification Search
CPC ........................................................ G09B 7/02
USPC ........................................................ 434/236
See application file for complete search history.

*Primary Examiner* — Thomas J Hong
(74) *Attorney, Agent, or Firm* — Sheridan Ross P.C.

(57) ABSTRACT

An presentation generator is disclosed for generating presentations for interacting with a user on a personal topic of, e.g., the user's selection, wherein the presentations assist the user in obtaining a greater awareness of his/her motivations and/or behaviors relating to the topic. In one embodiment, the presentation generator generates and presents to the user textual observations, questions, and/or statements for the user's consideration. Such presentations use and/or are consistent with textual descriptions obtained from: (a) the results of one or more personality/motivation test results, and (b) user inputs, e.g., regarding the selected topic together with his/her confidence in the validity of such inputs. The invention organizes the textual descriptions so that outputs to the user can be generated from various personality/motivational perspectives thereby assisting the user in viewing the topic of discussion from different perspectives and thereby becoming more aware of his/her biases, motivations, and/or concerns relating to the topic.

1 Claim, 68 Drawing Sheets

Relationship Anatomy Model: Big Picture

Related U.S. Application Data

12/987,555, filed on Jan. 10, 2011, now Pat. No. 8,226,418, which is a continuation of application No. 10/896,438, filed on Jul. 21, 2004, now Pat. No. 7,874,841, which is a continuation-in-part of application No. 10/367,074, filed on Feb. 13, 2003, now abandoned, which is a continuation-in-part of application No. 10/215,954, filed on Aug. 8, 2002, now abandoned.

(60) Provisional application No. 60/310,886, filed on Aug. 8, 2001.

Fig. 1  Block Diagram Of The Invention

Fig. 2   MOTIVATION MANAGER 3

MINDSET DEVELOPER 4

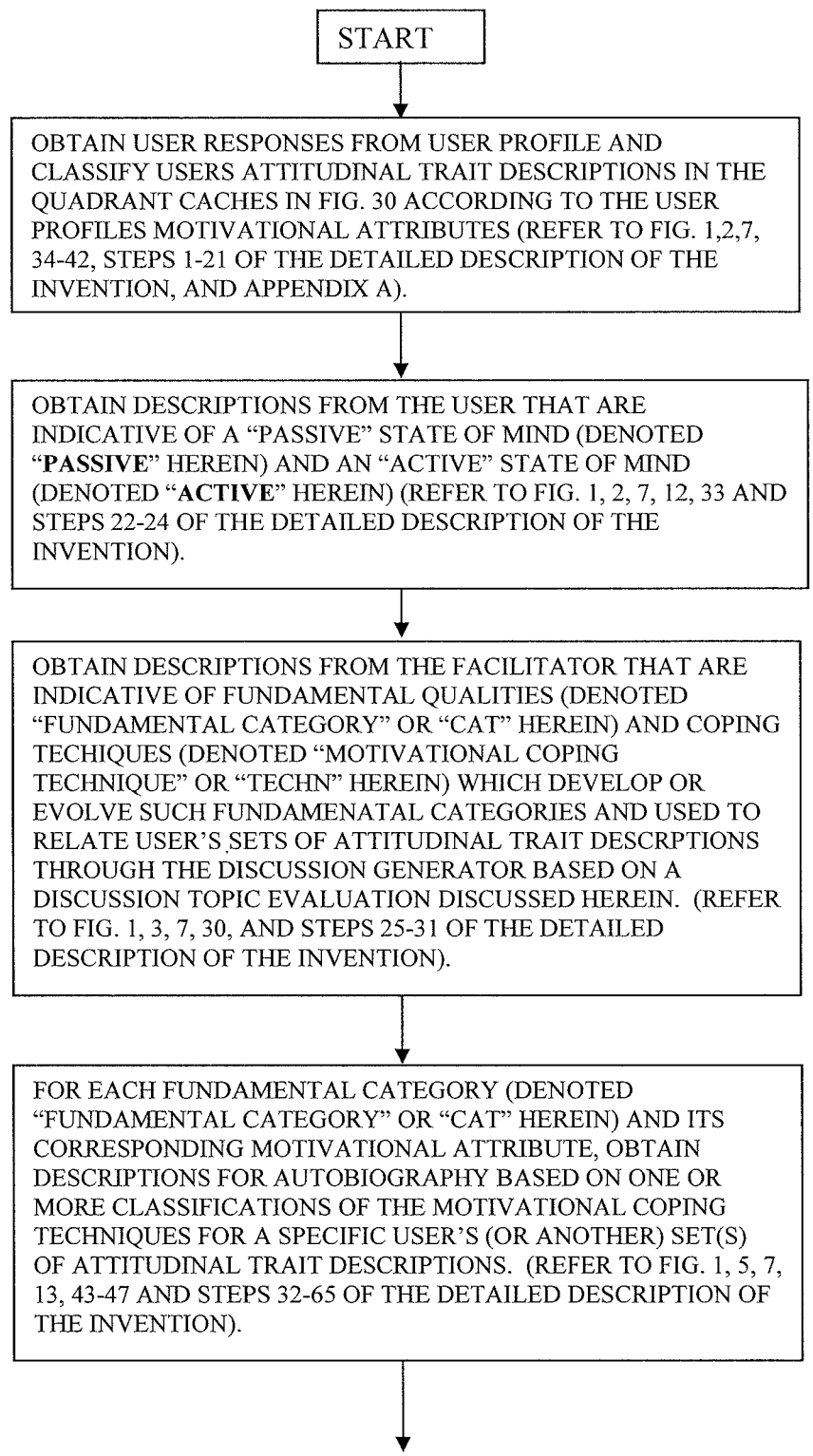
Fig. 6A — High Level Flowchart Of The Invention

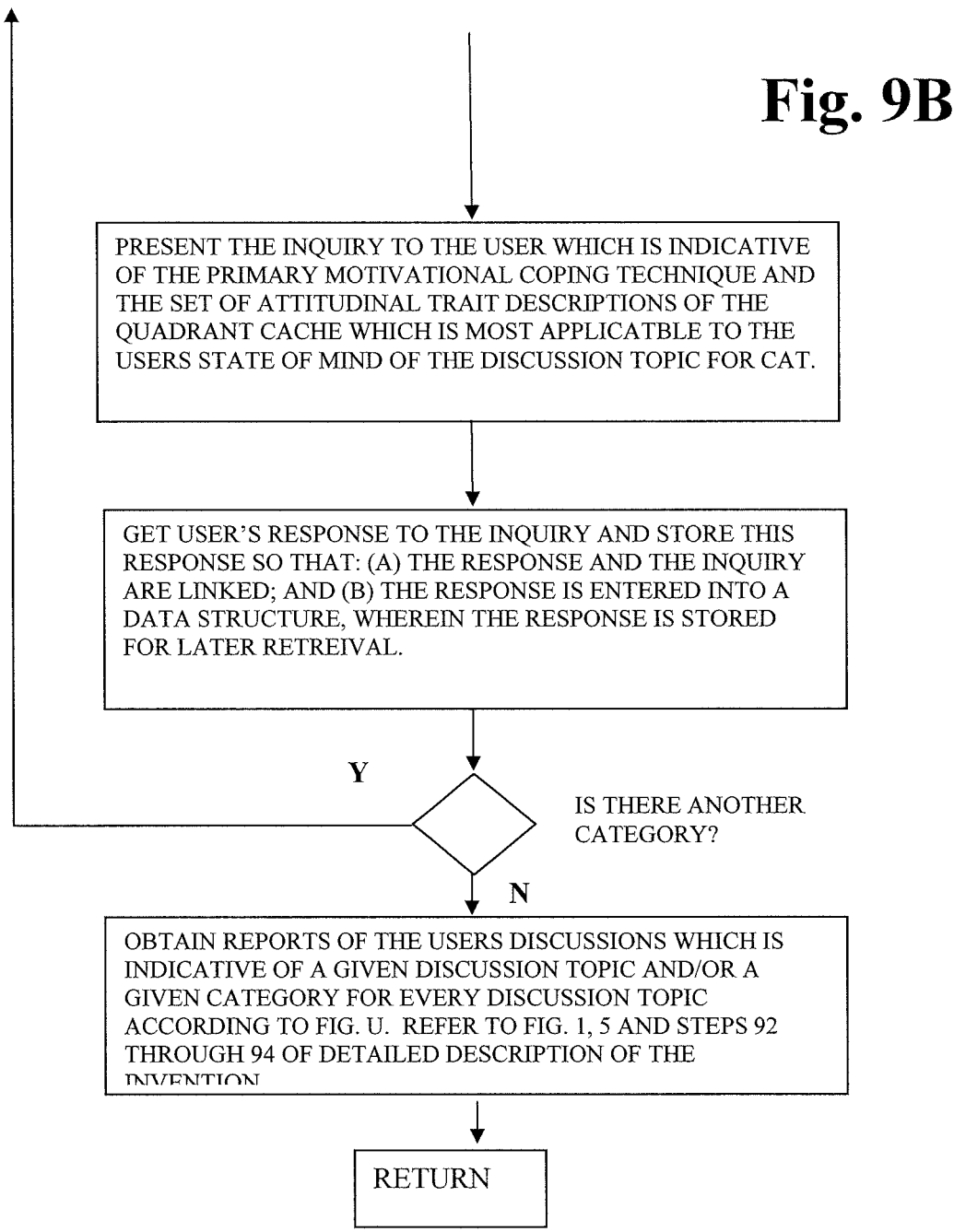

Fig. 26

View Discussion Report

Discussion Name: relationship with Karen
Date: 11/3/2003
Discussion #: 1

How could you appreciate others potential strengths?
I would create a journal entry based on the inquiry given regarding my relationship with Karen.

How can you fulfill your most passionate interests?
I would create a journal entry based on the inquiry given regarding my relationship with Karen.

How could you understand others potentially difficult stress reactions?
I would create a journal entry based on the inquiry given regarding my relationship with Karen.

What would you accept from others potentially important needs?
I would create a journal entry based on the inquiry given regarding my relationship with Karen.

Fig. 27

View Category Report

Category: Confidence

Discussion Name: relationship with Karen
Date: 11/3/2003

I would create a journal entry based on the inquiry given regarding my relationship with Karen.

Discussion Name: lack of knowing non-profit
Date: 10/28/2003

I would create a journal entry based on the inquiry given regarding my work.

Discussion Name: meeting with Birkman
Date: 10/25/2003

I would create a journal entry based on the inquiry given regarding my fun & recreation.

Discussion Name: ability to finish the patent
Date: 10/17/2003

I would create a journal entry based on the inquiry given regarding my family.

Fig. 28

My Autobiography Report

Name: <user's future self name>

Managing My Confidence
Enter answer for question or statement #1 for the Fundamental Category Confidence
Enter answer for question or statement #2 for the Fundamental Category Confidence
Enter answer for question or statement #3 for the Fundamental Category Confidence
Enter answer for question or statement #4 for the Fundamental Category Confidence

Managing My Patience
Enter answer for question or statement #1 for the Fundamental Category Patience
Enter answer for question or statement #2 for the Fundamental Category Patience
Enter answer for question or statement #3 for the Fundamental Category Patience
Enter answer for question or statement #4 for the Fundamental Category Patience

Managing My Devotion
Enter answer for question or statement #1 for the Fundamental Category Devotion
Enter answer for question or statement #2 for the Fundamental Category Devotion
Enter answer for question or statement #3 for the Fundamental Category Devotion
Enter answer for question or statement #4 for the Fundamental Category Devotion

Managing My Honor
Enter answer for question or statement #1 for the Fundamental Category Honor
Enter answer for question or statement #2 for the Fundamental Category Honor
Enter answer for question or statement #3 for the Fundamental Category Honor
Enter answer for question or statement #4 for the Fundamental Category Honor

Fig. 29  Linguistic Constructs Table

| Record # | Fundamental Category | Motivational Attribute | State of Mind Location | Begin Question | Motivational Attribute Description | Auxiliary Verb | Motivational Coping Technique | State of Mind Description | Attitudinal Trait Description ID |
|---|---|---|---|---|---|---|---|---|---|
| 1 | confidence | need | ActiveLeft | Which | your needs | will you | Allow | Passive | A.1.1 QCache 1 |
| 2 | confidence | need | ActiveLeft | Which | your most important needs | will you | Accept | Passive | A.1.2 QCache 2 |
| 3 | confidence | need | ActiveLeft | How | others potential needs | could you | Maintain | Active | A.2.3 QCache 3 |
| 4 | confidence | need | ActiveLeft | How | others potentially important needs | could you | Support | Active | A.2.4 QCache 4 |
| 5 | patience | stress reaction | ActiveLeft | Which | your stress reactions | will you | Excuse | Passive | B.1.1 QCache 1 |
| 6 | patience | stress reaction | ActiveLeft | Which | your most difficult stress reactions | will you | Forgive | Passive | B.1.2 QCache 2 |
| 7 | patience | stress reaction | ActiveLeft | How | others potential stress reactions | could you | Comprehend | Active | B.2.3 QCache 3 |
| 8 | patience | stress reaction | ActiveLeft | How | others potentially difficult stress reactions | could you | Understand | Active | B.2.4 QCache 4 |
| 9 | devotion | interest | ActiveLeft | Which | your interests | will you | Consider | Passive | C.1.1 QCache 1 |
| 10 | devotion | interest | ActiveLeft | Which | your most passionate interests | will you | Discover | Passive | C.1.2 QCache 2 |
| 11 | devotion | interest | ActiveLeft | How | others potential interests | could you | Acknowledge | Active | C.2.3 QCache 3 |
| 12 | devotion | interest | ActiveLeft | How | others potentially passionate interests | could you | Fulfill | Active | C.2.4 QCache 4 |
| 13 | honor | strength | ActiveLeft | Which | your strengths | will you | Observe | Passive | D.1.1 QCache 1 |
| 14 | honor | strength | ActiveLeft | Which | your most consistent strengths | will you | Admire | Passive | D.1.2 QCache 2 |
| 15 | honor | strength | ActiveLeft | How | others potential strengths | could you | Appreciate | Active | D.2.3 QCache 3 |
| 16 | honor | strength | ActiveLeft | How | others potentially consistent strengths | could you | Respect | Active | D.2.4 QCache 4 |
| 17 | confidence | need | ActiveRight | How | your needs | can you | Maintain | Active | A.1.1 QCache 1 |
| 18 | confidence | need | ActiveRight | How | your most important needs | can you | Support | Active | A.1.2 QCache 2 |
| 19 | confidence | need | ActiveRight | Which | others potential needs | would you | Allow | Passive | A.2.3 QCache 3 |
| 20 | confidence | need | ActiveRight | Which | others potentially important needs | would you | Accept | Passive | A.2.4 QCache 4 |
| 21 | patience | stress reaction | ActiveRight | How | your stress reactions | can you | Comprehend | Active | B.1.1 QCache 1 |
| 22 | patience | stress reaction | ActiveRight | How | your most difficult stress reactions | can you | Understand | Active | B.1.2 QCache 2 |
| 23 | patience | stress reaction | ActiveRight | Which | others potential stress reactions | would you | Excuse | Passive | B.2.3 QCache 3 |
| 24 | patience | stress reaction | ActiveRight | Which | others potentially difficult stress reactions | would you | Forgive | Passive | B.2.4 QCache 4 |
| 25 | devotion | interest | ActiveRight | How | your interests | can you | Acknowledge | Active | C.1.1 QCache 1 |
| 26 | devotion | interest | ActiveRight | How | your most passionate interests | can you | Fulfill | Active | C.1.2 QCache 2 |
| 27 | devotion | interest | ActiveRight | Which | others potential interests | would you | Consider | Passive | C.2.3 QCache 3 |
| 28 | devotion | interest | ActiveRight | Which | others potentially passionate interests | would you | Discover | Passive | C.2.4 QCache 4 |
| 29 | honor | strength | ActiveRight | How | your strengths | can you | Appreciate | Active | D.1.1 QCache 1 |
| 30 | honor | strength | ActiveRight | How | your most consistent strengths | can you | Respect | Active | D.1.2 QCache 2 |
| 31 | honor | strength | ActiveRight | Which | others potential strengths | would you | Observe | Passive | D.2.3 QCache 3 |
| 32 | honor | strength | ActiveRight | Which | others potentially consistent strengths | would you | Admire | Passive | D.2.4 QCache 4 |

Relationship Anatomy Model: Quadrant Caches

Axis Labels:
y  - Awareness Level
x  - Differentness

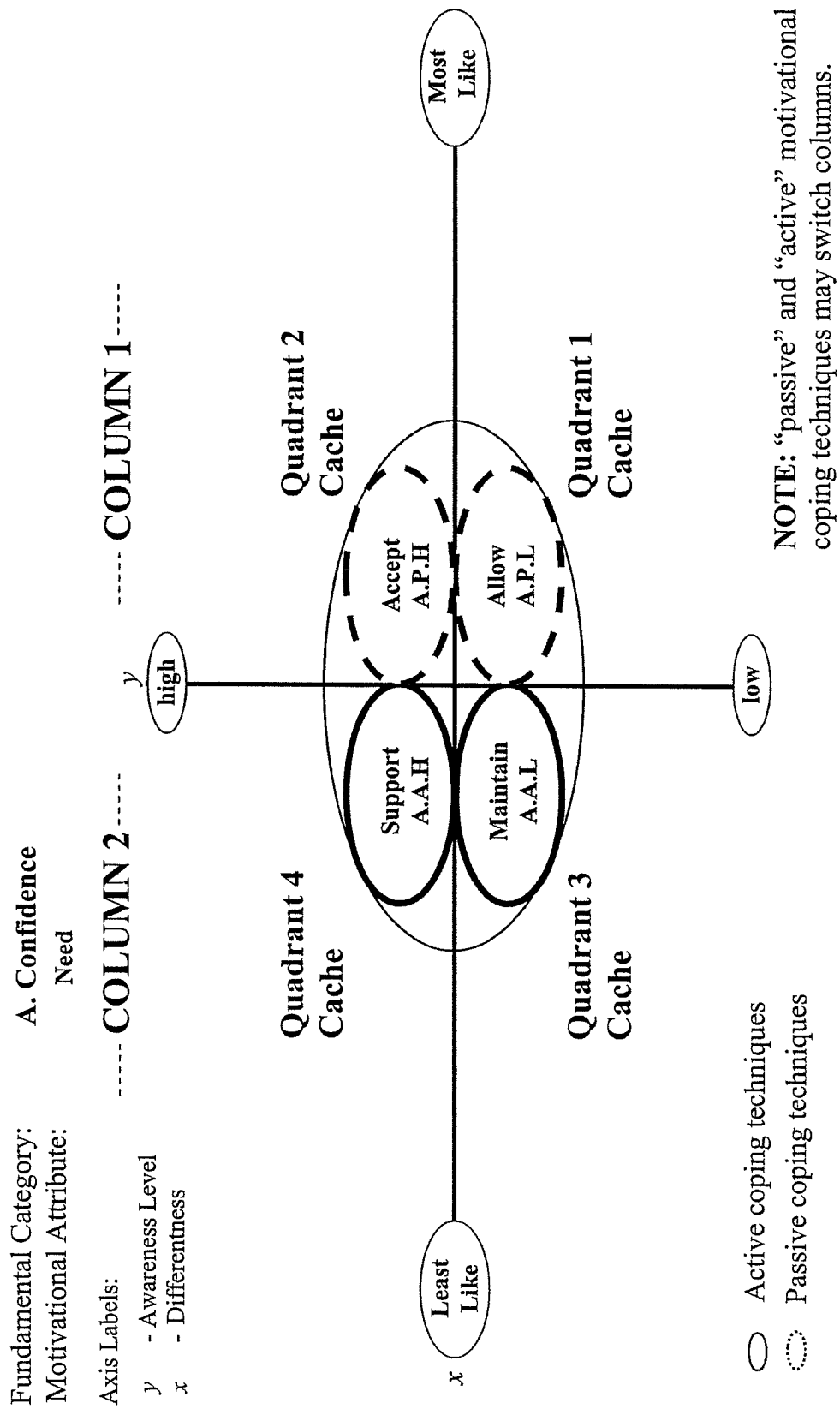

Relationship Anatomy Model: Patience & Stress Reactions

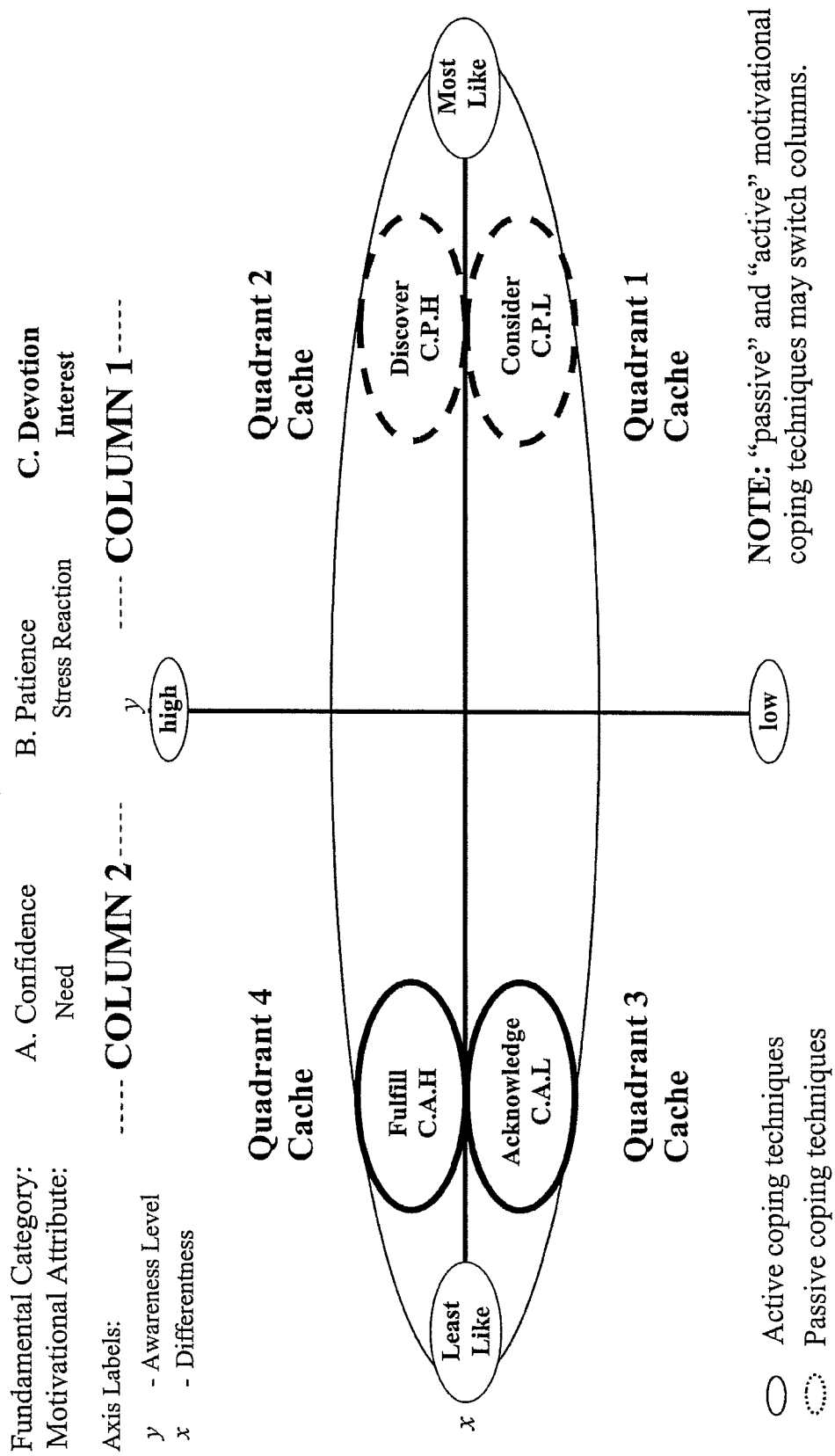

Fig. 31

Relationship Anatomy Model: Attitudinal Trait Sets

| Fundamental Category: | A. Confidence | B. Patience | C. Devotion | D. Honor |
|---|---|---|---|---|
| Motivational Attribute: | needs | stress reactions | interests | strengths |

| Column 2 | High Awareness | Column 1 |
|---|---|---|

Quadrant 4 Cache

- D.2.4. insightful and intuitive
  likes to reflect before acting
  low-key in the exercise of authority
- C.2.4. exercising strong managerial authority
  approaching issues holistically
  approaching problems factually and logically
- B.2.4. failing to accept necessary change
  being impulsive
  discomfort with unusual ideas
- A.2.4. an unemotional environment
  an environment based on trust
  issues reduced to their simplest form

Quadrant 2 Cache

- D.1.2. likes a variety of simultaneous tasks
  oriented towards general benefit
  friendly and easy to know
- C.1.2. educational approaches to development
  comfort in problem solving and crisis intervention
  managing through knowledge and expertise
- B.1.2. becoming domineering and controlling
  indecision when pressured
  failing to delegate when necessary
- A.1.2. plenty of different calls on attention
  an outlet for subjective issues
  a way to measure personal performance Least Like                  Most Like

Quadrant 3 Cache

- D.2.3. concentrates attention well
  oriented toward individual advantage
  able to work well alone
- C.2.3. completing any details
  a minimum of directive involvement
  hard work - rewarding self-motivation
- B.2.3. putting things off
  over-insistence on following procedures
  failing to address issues of control
- A.2.3. personal control over scheduling
  adequate notice of any change
  a definite plan in place

Quadrant 1 Cache

- D.1.1. takes direct action to get things done
  direct and straightforward
  directive and commanding
- C.1.1. positive relationships and mutual trust
  a commitment to major responsibilities
  imagination and intuitiveness
- B.1.1. weakness in follow-through
  getting distracted too easily
  being different for its own sake
- A.1.1. plenty of time for complex decisions
  a busy schedule
  only an outline to follow Low Awareness

Personal Core Values

Relaxing Values

First, describe my future-self exercise experience. Second, enter a name for your future self. Third, enter three values that incorporate your future self experience.

Future Self Experience: ENTER A "FUTURE SELF" DESCRIPTION

Future Self Name: ENTER A "FUTURE SELF" NAME

Incorporates... creativity, clarity, and satisfaction

Motivating Values

First, describe my peak exercise experience. Second, enter three values that incorporate your peak experience.

Peak Experience: ENTER A "PEAK EXPERIENCE" DESCRIPTION incorporates... freedom, vitality, and connecting Close

List of Potential Values
Accomplishment/Result
Achievement
Adventure/Excitement
Aesthetics/Beauty
Altruism
Autonomy
Clarity
Commitment
Community
Completion
Connecting/Bonding
Creativity
Emotional Health
Environment
Freedom
Forward the Action
Fun
Honesty
Humor
Integrity
Intimacy
Joy
Leadership
Loyalty
Openness
Personal Growth/Learning
Mastery/Excellence
Orderliness/Accuracy
Nature Add Value

Fig. 33

Personal Behavior Input

Enter your Birkman results from the Summary One Components and Interview Guide Reports:

[Submit]

Components:

| | Usual | Need | Stress |
|---|---|---|---|
| Relating to Individuals | 8 | 57 | 57 |
| Relating to People in a Group | 99 | 61 | 61 |
| Systems and Procedures | 49 | 30 | 30 |
| Directing and Controlling | 74 | 38 | 75 |
| Teamwork and Individual Competitiveness | 10 | 65 | 65 |
| Preferred Pace for Action | 99 | 92 | 92 |
| Demands for Work | 41 | 41 | 41 |
| Involvement of Feeling | 46 | 69 | 69 |
| Dealing with Change | 96 | 96 | 96 |
| Personal Independance | 67 | 36 | 75 |
| Action or Reflection | 31 | 99 | 99 |

Interview Guide:

| | Interests |
|---|---|
| Knowledge Specialist | 10 |
| Directive Management | 5 |
| Delegative Management | 1 |
| Work Motivation | 2 |
| Self Development | 10 |
| Corporate Adapt | 9 |
| Social Adapt | 9 |
| Social Responsibility | 7 |
| Public Contact | 7 |
| Detail | 4 |
| Global | 4 |
| Linear | 7 |
| Conceptual | 9 |
| Concrete | 2 |

Motivational Attributes

Click on one of the four attributes below

| Done |

1. ○ Strengths   2. ○ Interests   3. ○ Stress Reactions   4. ⊙ Needs

Complete both questions below for each category by selecting one motivation at a time and moving it with the arrows.

What three motivations are your most important needs?

...plenty of time for complex decisions
...a busy schedule
...only an outline to follow

⬆
⬇

...plenty of different calls on attention
...an outlet for subjective issues
...a means of measuring personal performance

What three motivations are others potentially important needs?

...adequate notice of any change
...personal control over scheduling
...a definite plan in place

⬆
⬇

...an unemotional environment
...an environment based on trust
...issues reduced to their simplest form

Fig. 37

Motivational Attributes

Done

Click on one of the four attributes below

1. ○ Strengths    2. ○ Interests    3. ⊙ Stress Reactions    4. ○ Needs

Complete both questions below for each category by selecting one motivation at a time and moving it with the arrows.

What three motivations are your most difficult stress reactions?

...indecision when pressured
...getting distracted too easily
...failing to delegate when necessary
...becoming domineering and controlling
...being different for its own sake
...weakness in follow-through

What three motivations are others potentially difficult stress reactions?

...being impulsive
...failing to accept necessary change
...putting things off
...failing to address issues of control
...discomfort with unusual ideas
...over-insistence on following procedures

Fig. 39

Motivational Attributes

Click on one of the four attributes below

| 1. ○ Strengths | 2. ⊙ Interests | 3. ○ Stress Reactions | 4. ○ Needs |

Done

Complete both questions below for each category by selecting one motivation at a time and moving it with the arrows.

What three motivations are your most passionate interests?

...managing through knowledge and expertise
...educational approaches to development
...imagination and intuitiveness
...a commitment to major responsibilities
...positive relationships and mutual trust
...comfort in problem solving and crisis intervention What three motivations are others' potentially passionate interests?

...a minimum of directive involvement
...approaching problems factually and logically
...hard work - rewarding self-motivation
...completing any details
...approaching issues from a holistic point of view
...exercising strong managerial authority

Fig. 42

Motivational Attributes

Click on one of the four attributes below

| Done |

1. ⦿ Strengths   2. ○ Interests   3. ○ Stress Reactions   4. ○ Needs

Complete both questions below for each category by selecting one motivation at a time and moving it with the arrows.

What three motivations are your most consistent strengths?

...takes direct action to get things done
...direct and straightforward
...directive and commanding

⬆⬇

...friendly and easy to know
...likes a variety of simultaneous tasks
...oriented towards general benefit What three motivations are others' potentially consistent strengths?

...concentrates attention well
...oriented toward individual advantage
...able to work well alone

⬆⬇

...likes to reflect before acting
...insightful and intuitive
...low-key in the exercise of authority

Fig. 44

Back | Establish a Solid Foundation

INSTRUCTIONS: Click 🔲 to enter each description for 1 through 4. IMPORTANT: When entering descriptions, write explanations that refer to the three attitudes listed.

1. Describe ways you allow or maintain others' potential needs.
- adequate notice of any change
- personal control over scheduling
- a definite plan in place 2. others' potentially important needs.
others potentially important needs.
- an unemotional environment
- an environment based on trust
- issues reduced to their simplest form 3. Describe ways you allow or maintain your needs.
- plenty of time for complex decisions
- a busy schedule
- only an outline to follow 4. Describe ways you accept or support your most important needs.
- plenty of different calls on attention
- an outlet for subjective issues
- a way to measure personal performance Confidence Most Like Me | Least Like Me

Fig. 46

[Back] Develop a Fulfilling Direction

INSTRUCTIONS: Click 🔍 to enter each description for 1 through 4. IMPORTANT: When entering descriptions, write explanations that refer to the three attitudes listed.

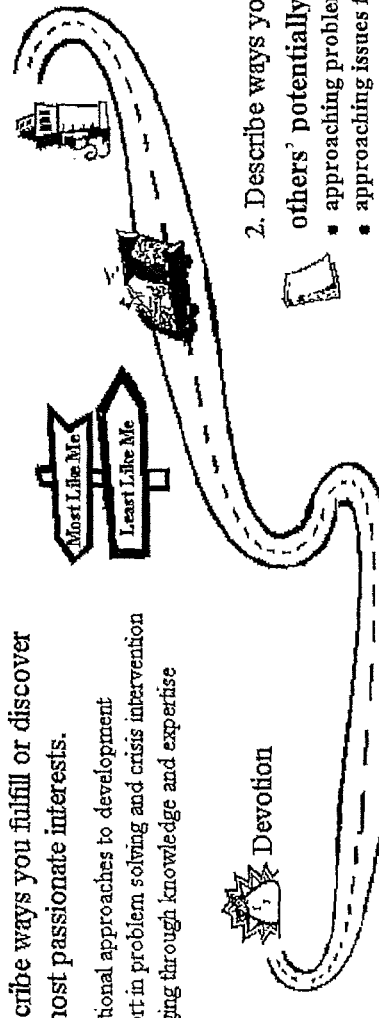

1. Describe ways you acknowledge or consider others' potential interests.
   - a minimum of directive involvement
   - hard work – rewarding self-motivation
   - completing any details 2. Describe ways you fulfill or discover others' potentially passionate interests.
   - approaching problems factually and logically
   - approaching issues from a holistic point of view
   - exercising strong managerial authority 3. Describe ways you acknowledge or consider your interests.
   - imagination and intuitiveness
   - a commitment to major responsibilities
   - positive relationships and mutual trust 4. Describe ways you fulfill or discover your most passionate interests.
   - educational approaches to development
   - comfort in problem solving and crisis intervention
   - managing through knowledge and expertise

Fig. 47

[Back] Value a Unique Connection

INSTRUCTIONS: Click 🗒 to enter each description for 1 through 4. IMPORTANT: When entering descriptions, write explanations that refer to the three attitudes listed.

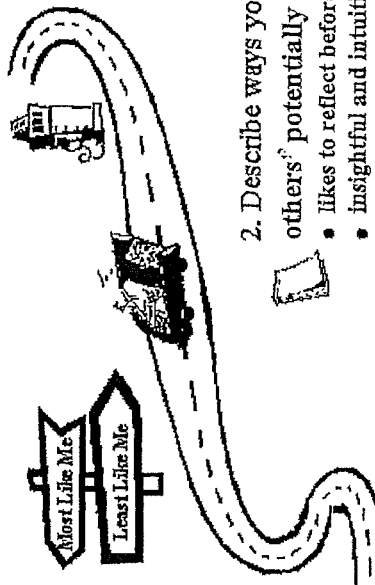

1. Describe ways you appreciate or observe others' potential strengths.
   - concentrates attention well
   - oriented toward individual advantage
   - able to work well alone 2. Describe ways you respect or admire others' potentially consistent strengths.
   - likes to reflect before acting
   - insightful and intuitive
   - low-key in the exercise of authority 3. Describe ways you appreciate or observe your strengths.
   - takes direct action to get things done
   - direct and straightforward
   - directive and commanding 4. Describe ways you respect or admire your most consistent strengths.
   - friendly and easy to know
   - likes a variety of simultaneous tasks
   - oriented toward general benefit

METHOD AND APPARATUS FOR
PERSONAL AWARENESS AND GROWTH

RELATED APPLICATIONS

The present patent application is a continuation-in-part patent application Ser. No. 15/429,606, filed Feb. 10, 2017 (now U.S. Pat. No. 10,055,802, issuing Aug. 21, 2018), which is a continuation of U.S. patent application Ser. No. 13/896,553, filed on May 17, 2013 (now U.S. Pat. No. 9,589,475, issued Mar. 7, 2017), which is a continuation of U.S. patent application Ser. No. 13/538,431, filed on Jun. 29, 2012 (now U.S. Pat. No. 8,449,300, issued May 28, 2013), which is a continuation of U.S. patent application Ser. No. 12/987,555, filed Jan. 10, 2011 (now U.S. Pat. No. 8,226,418, issued Jul. 24, 2012), which in turn is a continuation of U.S. patent application Ser. No. 10/896,438, filed Jul. 21, 2004 (now U.S. Pat. No. 7,874,841, issued Jan. 25, 2011), which in turn is a continuation-in-part of U.S. patent application Ser. No. 10/367,074 filed Feb. 13, 2003, which in turn is a continuation-in-part of U.S. patent application Ser. No. 10/215,954 filed Aug. 8, 2002, which claims the benefit of U.S. Provisional Patent Application Ser. No. 60/310,886 filed Aug. 8, 2001. The entire disclosure of the prior applications are incorporated by reference herein and is considered to be part of the disclosure of the present application.

FIELD OF THE INVENTION

The present application relates generally to a computational system and method for facilitating personal growth and/or insights. More particularly, the present invention provides a method and system for interacting with a user using linguistic presentations that are customized to both a personal profile of the user as well as the user's understanding of particular words and/or phrases for gaining such personal growth and/or insights. In at least one embodiment, the invention computationally combines: (a) semantic linkages between words and/or phrases with (b) a novel syntactic analysis to produce textual output for a designated discussion topic, wherein the textual output is generated using a user requested view point on the topic.

BACKGROUND OF THE INVENTION

Every living thing that exists has energy that integrally supports the life process in all its aspects—the material operations of the physical body, the functions of the emotions and mind, and even the spiritual life. Every individual has a different energy pattern and growth potential that fluctuates through each day and throughout the individual's lifetime. To be able to take advantage of or to recognize the fluctuations in one's energy levels could greatly increase the individual's productivity and well-being, both at work and at home, and would enhance the individual's growth. The prior art discusses different ways of assessing an individual's energy and potential for growth; however, such assessments are not necessarily an exact science. Indeed, the intension of the prior art is to identify a method that quantifies the energy pattern and/or growth potential of an individual. The prior art recommends that an "energy healer" (denoted as "facilitator" herein) or one skilled in the art of addressing an individual's energy to diagnose or address an individual's energy functions and potential dysfunctions and to use the combination of the healer's and individual's own experiences to direct the individual's energy into the individual's 'functional' or 'preferred' energy field. Energy healing encompasses a large array of slightly different therapies including but not limited to: Psychology, Healing Touch, Reflexology, Biofield Therapeutics, Therapeutic Touch, Reiki, and Chi Gung Therapy. However, none of these therapies provide a quantitative approach in both assessing an individual's energy pattern and providing direction or focus to an individual's preferred energy pattern. Such a quantitative approach is needed and the present invention supplies a needed approach.

Terms and Definitions (in Alphabetical Order)

(Note: terms bolded and italicized in this section are also defined in this Terms and Definitions section)

Attitudinal Trait Description

A description that represents a user's likely (denoted as "most like" herein) or unlikely (denoted as "least like" herein) behavior or attitude (e.g., behaves as if he/she needs, or prefers—plenty of time for complex decisions). Refer to Appendix A, and FIG. 31.

Autobiography

The autobiography stores the user's written journal entries based on questions (denoted as "autobiography statements" herein) that elicit a response from the user wherein the questions are generated based on, pre-defined sets of values (denoted as "fundamental categories" herein), coping descriptors (denoted as "motivational coping techniques" herein), and the user's "most like' or "least like" pre-determined set of behaviors or attitudes (denoted as a "set of attitudinal trait descriptions" herein). Refer to FIGS. 43 through 47, and 29, Awareness Level The awareness level represents the vertical axis in the Relationship Anatomy Model in FIG. 30*a* through FIG. 30*f*.

Autobiography Statement

An autobiography statement is a generated question directed to the user wherein the autobiography statement elicits a response from the user that guides the user in developing their personal autobiography.

Confidence Level Indicator

The confidence level indicator (e.g., "high" or "low") is selected by the user for various initial statements and questions that are presented in preparation for a user interaction on a discussion topic, wherein this indicator determines the level of difficulty that a user is likely to encounter in attempting to respond to the inquiries generated back to the user by the present invention. Refer to FIG. 48.

Coping Evolution Requirements

Refer to the Detailed Description Of The Coping Evolution Requirements section.

Discussion Generator

The discussion generator gathers input from the facilitator/user and generates output in the form of inquires back to the user which can include the user's "most like" or "least like" set of behaviors or attitudes (denoted as "attitudinal trait descriptions" herein) Refer to FIGS. 50 through 53.

Discussion Topic

A discussion topic is defined by the user wherein the discussion topic is the subject in which the user would like to investigate. For example, such a discussion topic might be "my relationship with my wife, Karen". Refer to FIG. 48.

Discussion Topic Evaluation
A discussion topic evaluation evaluates or measures how well a user perceives the discussion topic (e.g., my relationship with my wife Karen) in which the user wishes to investigate. Refer to FIG. 48.

Electronic Journal
The electronic journal is where the user may enter journal entries based on inquiries generated back to the user. Refer to FIGS. 50 through 53.

Evaluation Procedure
The evaluation procedure refers to the user profile or motivational instrument facilitated by an expert in the field and given to a user of this system wherein the evaluation procedure is treated as input to the present invention. Refer to Appendix A.

Fundamental Category
A fundamental category is an essential quality or virtue which represents one of multiple "ideal" ways to relate to a person, thing, or situation (In one embodiment, fundamental categories are defined as "confidence", "patience", "devotion", and "honor" wherein such fundamentals are intended to represent an optimum relationship). The fundamental categories are nouns that are primarily defined by the facilitator (e.g., a person that assists a user in interacting with the present invention) in the FUNDAMENTAL CATEGORY CONSTRUCTOR 14 in FIG. 3. Refer to FIGS. 30b through 30f and the definition of The Relationship Anatomy Model in this section.

Good Ranking Range
The user evaluates a situation, relationship, or issue (i.e., discussion topic) by ranking true/untrue statements from 1 to 10 and a good ranking range is a rank of 6 through 10. Refer to FIG. 48.

Implied Rank
The implied rank is a rank calculated by this system based on the original rank entered by the user for a discussion topic.

Inquiry
An inquiry is generated back to a user based on a user's discussion topic evaluation wherein the user reads the inquiry to help investigate ways to approach a given discussion topic. Refer to FIGS. 50 through 53.

Linguistic Constructs Table
The Linguistic Constructs Table stores the data used to build inquires which are generated back to the user for investigation of the user's discussion topic and/or autobiography. Refer to FIG. 29 and the Detailed Description Of The Linguistic Constructs Table.

Motivational Attribute
A motivational attribute (e.g., "need") is an essential source or driver which serves to develop or evolve (more generally, determine) the aspects in a user's perception of a user-defined discussion topic.

Motivational Coping Technique
A motivational coping technique (e.g., "allow") is a verb (e.g., this verb must also have a capability to be used as a transitive verb) representing a motive which is intended to develop or evolve a user's perception of a user-defined discussion topic.

Poor Ranking Range
The user evaluates a situation, relationship, or issue (i.e., discussion topic) by ranking true/untrue statements from 1 to 10 and a poor ranking range is a rank of 1 through 5. Refer to FIG. 48.

Primary Motivational Coping Technique
A primary motivational coping technique (e.g., "allow") is a representation of the primary motive for a generated inquiry, wherein the inquiry is intended to elicit a user response toward a (user) designated discussion topic, and wherein the primary motive is selected from a predetermined collection of textual representations, each textual representation describing a potential motivation that could be applicable to the user.

Quadrant Cache
A quadrant cache is part of the Relationship Anatomy Model design. A quadrant cache represents a plurality of interchangeable variables and either a "low" or "high" awareness level or either "most-like" the user or "least-like" the user behaviors or attitudes. Refer to FIGS. 30a through 30f.

Rank
A rank is a score that the user enters when evaluating a discussion topic. The rank entered is between 1 (e.g., mostly untrue) and 10 (e.g., mostly true). The rank entered either doesn't satisfy (e.g., a low rank) or satisfies (e.g., a high rank) the user's perception of the discussion topic. Refer to FIG. 48.

Relationship Anatomy Model
The relationship anatomy model is a data model that, at least in one embodiment, enables a user to relate their perception of a user-defined situation, relationship, event, etc. (e.g., discussion topic) to the data model's predefined data organization, wherein this data organization includes related or "linked" data items, each data item identifying/describing an attribute or characteristic of the user's motivations and/or personal traits. Moreover, this data organization may be used by the user to investigate his/her perceptions regarding various discussion topics. In particular, each such data item can be from one (and only one) of the following components or classifications of the user's motivations and/or personal traits: fundamental categories, user states of mind, user motivational attributes, user motivational coping techniques, and the user's attitudinal trait descriptions. Accordingly, the relationship anatomy model's components or classification are used to generate meaningful inquiry's or questions to the user through a response algorithm. The response algorithm builds and generates inquiries back to the user based on the user's perception of the discussion topic, wherein these inquiries are built directly from the linkages of the data items of the user's specific relationship anatomy model. In addition, the Linguistic Constructs Table is designed based on the data organization of the relationship anatomy model. Refer to FIG. 30a through FIG. 30f, the Linguistic Constructs Table Detailed Description, and The Detailed Description Of The Coping Evolution Requirements for further description.

Response Algorithm
The response algorithm calculates the user's perception of a discussion topic in relation to the Relationship Anatomy Model. The intention of the response algorithm is to reflect how a user perceives a discussion topic.

Response Type
The response type represents how a user requests to receive an inquiry generated back to them based on a discussion topic evaluation. For one embodiment, a user may request an "empower" response type which produces an inquiry that represents the user's "strongest" perception of a discussion topic. Or alternatively, the user may request an "improve" response type which produces an inquiry that represents the user's "weakest" perception of a discussion topic. Refer to FIG. 48 and steps 68 through 72 of the Detailed Description Of The Invention.

Set of Attitudinal Trait Descriptions

A set of attitudinal trait descriptions wherein these descriptions either represent how a user "most likely" behaves or "least likely" behaves according to the behavioral or motivational procedure (i.e., evaluation procedure).

State of Mind

There are two ideal types of states of mind presupposed in at least some embodiments of the present invention. A "passive" state of mind represents a user's relaxed disposition (e.g., suggesting less effort). An "active" state of mind represents a user's active disposition (e.g., suggesting more effort). These states of mind are designed into the relationship anatomy model and provide a means of relating (in some cases with less effort (e.g., passively) and in some cases with more effort (e.g., actively)) the user's perception to a discussion topic. Refer to FIG. 30*f*.

State of Mind Description

A state of mind description is made of one-word descriptors which represents a user's "passive" and "active" state of mind. For example, a "passive" state of mind description may be defined as: creativity, clarity, and satisfaction and an "active" state of mind may be defined as: freedom, vitality, connecting. These descriptions are used in the inquiries generated back to the user and they are defined with the facilitator or someone experienced in defining such descriptions.

Sub-Rank

Sub-ranks are scores calculated by the response algorithm based on a rank entered by the user when evaluating a discussion topic. A sub-rank represents a user's set of behaviors or attitudes (i.e., set of attitudinal trait descriptions).

True/Untrue Statement

One or more true/untrue statements are presented to a user that requires the user to enter specific criteria (e.g., rank, confidence level indicator of high or low, and a response type of empower or improve) for each statement when evaluating a discussion topic. Refer to FIG. 48.

SUMMARY OF THE INVENTION (Note: words shown in bold text below are defined in the Terms and Definitions section above; only the first instance of each term is in bold format)

Overall, it is important to note that the present invention provides a computational structure for creating applications wherein the structure provides a programmatic and syntactical computational framework for being able to describe or define specific applications that generate meaningful or purposeful discussions or thought processes for users to manage or learn preferred outcomes in which the application is designed or intended. For example, the computational structure of the present invention is like a "Microsoft Excel" program whereas each such application is like a "spreadsheet" created from the "Microsoft Excel" program to manage, e.g., a specific financial outcome. As a reader of the present invention, you will notice that present invention describes: (1) the computational structure along with (2) at least one application using the computational structure. In particular, the application described herein aids users in gaining greater insight or awareness for understanding: (a) their motivations, and/or (b) their likely (denoted as "most like" herein) or unlikely (denoted as "least like" herein) behavior responses toward a specific user-defined situation (denoted as "discussion topic" herein).

In one embodiment the present invention may be embodied as a discussion generator for assisting a person (i.e., a user) in becoming more aware or gaining greater understanding of his/her perceptions on various "discussion topics", wherein a discussion topic may be a particular situation regarding, but not limited to, career, family, personal growth, fun/recreation, relationship, etc.

More specifically, the present invention provides a syntactic representation (i.e., the combination of both data and programmatic algorithms) of a user's motivations and/or 'most like" or "least like" behavior responses so that the syntactic representation can be used to generate customized inquiries to be provided to the user. Additionally, the syntactic representation is intended to model how a user prefers to: (a) use language to think, and (b) describe how a user prefers to perceive his/her world/environment. Thus, by combining both the data defined for a specific application with the programmatic algorithms of the present invention, a programmatic system that expresses ideas, questions and statements in language (i.e., words, terms and phrases) that is more meaningful to the user, and thereby provides the user with greater insight into how the user experiences and/or prefers to perceive his/her environment.

In one embodiment, the present invention may be considered an intelligent process for providing users with the computational structure to aid them in describing and/or assessing personalized content (e.g., exploring a particular topic) representative of preferred: (1) sets of values (denoted as "fundamental categories" herein), (2) coping descriptors (i.e., descriptions of coping behavior, also denoted as "motivational coping techniques" herein), and (3) personalized attitudes or behaviors (denoted as "attitudinal trait descriptions" herein). For example, for a set of values including a fundamental category denoted: "generosity", a corresponding coping descriptor that is meaningful to the user (although not necessarily practiced by the user) might be the verb phrase: "feeding the poor", and a set of corresponding attitudinal trait descriptions applicable to the user might be: "prefers to be with people", and "prefers to be in control of situations". In particular, the resulting described personalized content provides data for generating inquiries back to the user that are intended to help the user learn how to better understand, perceive and/or recognize his/her attitudes and/or perceptions as they relate to a user-defined discussion topic. Accordingly, the user can investigate, reflect upon, and/or gain greater insight into his/her perceptions related to the discussion topic and the user's specific attitudinal trait descriptions related thereto.

The discussion generator of the present invention may extract specific user attitudinal trait descriptions from an evaluation procedure that evaluates the user's perceptions in relation to a predetermined set of attitudinal traits. Such attitudinal traits (and more particularly, the attitudinal trait descriptions derived therefrom) are then passed to the discussion generator wherein inquiries are generated to and/or interactions are initiated with the user so that the user gains a greater awareness of a given discussion topic. In one embodiment of the invention, a personal evaluation test corresponding to the Birkman Method (developed and distributed by Birkman International, Inc., 3040 Post Oak Blvd., Suite 1425, Houston, Tex. 77056 USA) is used as (one of) the evaluation procedure(s). Such evaluation procedures are also known as "motivational instruments" and are commonly thought of as providing a description or profile of a user's personality. However, a more precise description is that such evaluation procedures determine the relative awareness and/or relative utilization of a predetermined set of attitudinal traits as compared to others that have also been similarly evaluated. In particular, the output from such an evaluation procedure may assist the discussion generator of the present invention (and the user as well) in classifying the user's "most like" (e.g., "like" behaviors or attitudes) and "least like" (e.g., "unlike" behaviors or attitudes) sets of attitudinal traits so that corresponding sets of attitudinal trait descriptions can be used in generating inquiries (e.g., statements and/or questions for the user's consideration or contemplation). Accordingly, such attitudinal trait descriptions and the inquiries generated therefrom support the user in understanding, perceiving, and/or recognizing his/her behaviors or attitudes related to a discussion topic. Note that such an evaluation procedure may be included in an embodiment of the invention or may be substantially separate therefrom.

Furthermore, in generating such inquiries, the invention uses (i) a pre-determined set of fundamental categories (e.g., in one embodiment: "confidence", "patience", "devotion", "honor") that represent "ideal" ways a user may relate to themselves or interact with their environment, and (ii) corresponding motivational coping techniques (e.g., in one embodiment for the fundamental category "confidence": "allow", "accept", "maintain", "support") that helps a user develop or evolve an awareness of each of the fundamental categories as they relate to a discussion topic. Note that such fundamental categories may be predefined by a user along with a "facilitator" who utilizes the present invention to aid the user in discovering ways to learn and/or cope with their "most like" and "least like" sets of attitudinal trait descriptions (e.g., behaviors or attitudes) during a process of associating and/or learning ways to incorporate personally important characteristics of such fundamental categories (e.g., "confidence") into the user's awareness. In particular, it is an aspect of the present invention that a facilitator may utilize this invention to aid the user in discovering ways to cope (e.g., "allow") with their "most like" and "least like" sets of attitudinal trait descriptions (e.g., needing plenty of time for complex decisions) in the context of a discussion topic defined by the user.

Moreover, it is yet another aspect of the present invention that the predetermined fundamental categories, the motivational coping techniques, and the sets of attitudinal trait descriptions are designed in such a manner that a user may input evaluations of a discussion topic into the invention, and the discussion generator of the present invention will use such evaluation for communicating back to the user through carefully designed inquiries which are the result of computational analysis of the evaluations as they relate to such fundamental categories, motivational coping techniques and sets of attitudinal trait descriptions so that the user can then consider (and preferably answer or address) subsequent statements or questions generated by the invention, and thereby gain a greater understanding of his/her motivations related to the discussion topic.

An additional aspect of the present invention is directed to a computational system (method and apparatus) for generating such discussion-topic directed inquiries and/or discussion-topic related interactions according to a predetermined set of one or more fundamental categories as defined by the facilitator and/or the user. In a typical embodiment of the invention, each such fundamental category represents a healthy quality (e.g., "confidence") of how the user may wish to perceive issues, situations and/or relationships. In addition, the facilitator and the user are able to define a set of motivational coping techniques for each fundamental category designed accordingly through what is referred to herein as Coping Evolution Requirements (refer to the Detailed Description Of The Coping Evolution Requirements) as it relates to the Relationship Anatomy Model that is particularly disclosed in FIGS. 30a through 30f. The motivational coping techniques are identified or represented as verbs in the present invention, wherein such verbs are specifically selected with the intention of developing or evolving an awareness by the user of the fundamental category for which the verbs are representative. As described above, a qualified facilitator or one skilled in the art may be required to predefine every fundamental category and the corresponding motivational coping techniques. Also as described above, to help further assist in gathering information for each such fundamental category, a user evaluation procedure is generally administered by a trained expert or institution that is well skilled in the art of human cognitive perception (e.g., personality profiles or motivational instruments). The result from such an evaluation procedure may be a "user profile" of the user's personality, behavior styles, attitudes, person-to-person interaction techniques, etc. (e.g., attitudinal trait descriptions). These attitudinal trait descriptions are classified into motivational attributes as defined by such a motivational instrument. Each such motivational attribute (e.g., "needs", "stress reactions", "interests", strengths) is also classified by the evaluation procedure within a fundamental category (e.g., "confidence", "patience", "devotion", "honor"). The relationships between fundamental categories, motivational attributes, motivational coping techniques, and sets of attitudinal trait descriptions will become more apparent from the description hereinbelow.

In one embodiment, such a user profile or motivational instrument can be substantially provided using the results from one or more of the Birkman collection of personal assessment tests available from Birkman International, Inc., 3040 Post Oak Blvd., Suite 1425, Houston, Tex. 77056 USA. More generally, such a user profile can be substantially provided using the results of other user profile's which use a binary scale to measure a plurality of different behaviors, attitudes, preferences, etc. (e.g., "attitudinal trait descriptions") within one or more attributes (e.g., "motivational attributes"). Other personality profiles or motivational instruments that may be used with (or as part of) the present invention, include: (1) Myers Briggs a personality test owned by Consulting Psychologists Inc, (2) DISC a personality test owned by Inscape Publishing, Inc, etc. The "Other Embodiment Descriptions" section hereinbelow provides additional alternative personality profiles or motivational instruments. Moreover, the result from such personality profiles or motivational instruments may be also dependent upon coaching sessions wherein the user is assisted in taking and/or interpreting the results from such a test(s) (e.g., one or more of the Birkman tests) by a trained personality assessment expert (i.e., facilitator). Note that the result from the evaluation procedure is typically indicative of the user's propensity to be consistent with, e.g., a description of an "idealized" user having particular predetermined or learned perceptions and/or behaviors (sometimes referred to as "styles" by those skilled in the art). Such a description of an idealized user may describe users at one extreme of a metric (e.g., having a "high" assessment for a particular grouping of behaviors traits), or describe users at an opposite extreme of such a metric (e.g., having a "low" assessment for the particular grouping of behaviors traits). In other words, such personality profiles or motivational instruments generally utilize extreme behaviors or attitudes to describe which are "most like" and "least like" the user. There are three major sections described in remainder of this summary section hereinbelow:

- A. Section A describes the mechanics of the invention as it relates to a user's motivation(s) (e.g., attitudinal trait descriptions) relative to a discussion topic, and the fundamental categories which relate to such motivation(s).
- B. Section B describes the mechanics of the invention as it relates to how a user interacts with this system in everyday situations, relationships, or aspects of general life (e.g., discussion topics).
- C. Section C describes the mechanics of the invention as it relates to documenting and reporting the user's experiences as it relates to the user's discussion topics and autobiography.

A. Section A describes the mechanics of the invention as it relates to a user's motivation (e.g., attitudinal trait descriptions) and the fundamental categories which relate to their motivations. In order to appreciate these mechanics of the present invention, the structural components of the Relationship Anatomy Model embodiment shown in FIG. 30a through FIG. 30f are briefly described immediately below in 1 through 6:

1. One aspect of the Relationship Anatomy Model stores instances of pre-defined relating qualities in the form of particular relating concepts (denoted as "fundamental categories" herein). The facilitator and the user of the system define such fundamental categories through the MINDSET DEVELOPER 4 component in FIG. 3. Also, once the fundamental categories are classified and defined, they are stored in a table called the Linguistic Constructs Table in FIG. 29 wherein the fundamental categories are established and entered in the Linguistic Constructs Table through the LINGUISTICS ORGANIZER 17 component in FIG. 4. As an example of such a fundamental category, there may be a fundamental category indicative of the user's "confidence". In addition, such a fundamental category (e.g., confidence) has a one-to-one relationship with a motivational attribute (e.g., needs) as primarily defined through the MOTIVATION MANAGER 3 component in FIG. 2 as described in more detail in subsection (2) immediately below. That is, such a "confidence" fundamental category may be useful for assessing the degree to which a user tends (or defaults) to assess a preferred outcome (e.g., satisfying a "need" instance) to a wide range of discussion topics. Thus, such a "confidence" fundamental category may be useful for determining, given the uncertainty of future circumstances, the propensity of the user to generally ascribe a greater weight to a preferred outcome than to a non-preferred outcome based on the recognition or awareness of the user's "most like" or "least like" set of needs. Additionally, such a need motivational attribute (as described in more detail in subsection (2) immediately below) provides attitudinal trait descriptions along with a pre-defined motivational coping technique(s) to support a user's "confidence" development or evolution in aspects of a particular discussion topic (e.g., the user's tendency to ascribe a preferred outcome to a future situation or relationship) in relation to a user's "most like" or "least like" specific needs. Thus, the term "confidence" (e.g., a fundamental category) in the present discussion may have the following description:

1.1. Confidence: to have trust or faith in something or someone. More particularly, whether (or to what degree) the user's perception of the conditions, generated substantially by the discussion topic (or substantially derived therefrom), are or will ultimately be consistent with the user's expectations (e.g., needs) of the conditions. Thus in using the present invention, a user performs an evaluation (denoted as "discussion topic evaluation" herein) according to this "confidence" fundamental category for assessing, e.g., the user's general level of confidence for or relating to aspects of a particular discussion topic. For instance, a discussion topic evaluation may be performed to determine the user's condition as it relates to the user's "confidence" for the particular discussion topic. Depending on the results of this evaluation, the discussion generator generates inquiries back to the user which is dependent upon a similarity and/or dissimilarity with attitudinal trait descriptions (e.g., attitudes or behaviors that represent the user's "most like" or "least like" needs) as well as prescribes a pre-defined way to cope (e.g., motivational coping technique) with developing or evolving the condition of the fundamental category "confidence". Note that in one or more embodiments of the invention, additional fundamental categories may be identified by the words: patience, devotion, and honor, wherein such additional categories may be described as follows:

1.2. Patience: bearing or enduring emotional pain, difficulty, provocation, or annoyance with calmness. More particularly, whether (or to what degree) the user's perception of undesirable conditions created by the discussion topic (or substantially derived therefrom), are generally (e.g., substantially consistently) accepted without substantial increase in the user's "most like" or "least like" stress reactions (e.g., as described in subsection (2) immediately below, stress reactions are defined as a motivational attribute for the fundamental category Patience).

1.3. Devotion: ardent, often selfless affection and dedication, as to a person or principle; love. More particularly, whether (or to what degree) the user perceives that he/she is actively interested in the discussion topic (or conditions arising that are related thereto) so that the user explores and/or sets goals that are related to the discussion topic as it relates to the user's "most like" or "least like" interests (e.g., as described in subsection (2) immediately below, interests are defined as a motivational attribute for the fundamental category Devotion).

1.4. Honor high respect, as that shown for special merit; esteem. More particularly, whether (or to what degree) the user perceives that he/she is incorporating their usual strengths within the discussion topic (or conditions arising that are related thereto) as they relate to the user's "most like" or "least like" usual strengths (e.g., as described in subsection (2) immediately below, usual strengths are defined as a motivational attribute for the fundamental category Honor).

Of course, additional and/or alternative fundamental categories may be used with the present invention as one skilled in the art will understand once the scope of the invention is fully appreciated. For example, such additional and/or alternative fundamental categories may be categories that represent learning new skills such as learning to grow a garden. Such fundamental categories for learning to grow a garden may be defined by a facilitator and a user of the present invention as preparedness, accumulation, designation, and maintenance (e.g., there may be more or fewer fundamental categories define). Or another example may be learning the most efficient and effective means to re-engineer an existing structure. Such fundamental categories that are representative of the most efficient and effective means to re-engineer an existing structure may be defined by a facilitator and a user of the present invention as salvage-ability, recyclable, fabrication, and environment. As one skilled in the will understand, there are an unlimited number of applications that may be used for this invention.

2. Another aspect of the Relationship Anatomy Model is that for each such fundamental category (e.g., "confidence") described above and defined through the MINDSET DEVELOPER 4 in FIG. 3, the present invention may associate one or more motivational attributes (e.g., "needs") for each fundamental category. The motivational attributes described in 2.1 through 2.5 below are defined within the MOTIVATION ATTRIBUTE CONSTRUCTOR 10 in FIG. 2, and are provided by the motivational instrument. However, such motivational attributes may be modified by the facilitator and the user, and are associated with at least one (and preferably each of a plurality) fundamental category as defined by the facilitator through the FUNDAMENTAL CATEGORY CONSTRUCTOR 14 in FIG. 3. Also, the motivational attributes are classified and stored in a table called the Linguistic Constructs Table in FIG. 29 wherein the motivational attributes are processed and organized through the LINGUISTICS ORGANIZER 17 component in FIG. 4.

A "motivational attribute" facilitates and is essential for the development or evolution of its corresponding fundamental category within a user. In particular, such motivational attributes classify user's "most like" or "least like" attitudinal trait descriptions as described later in this summary which provide additional guidance in establishing, in guiding the development or evolution of, and/or using motivational coping techniques that are intended to facilitate generation inquiries related to the fundamental category regarding the user's perception of a discussion topic. Examples of such motivational attributes for fundamental categories as described above are as follows.

2.1. For the above mentioned fundamental category of "confidence", the corresponding motivational attribute is denoted as "needs", wherein "needs" may be described as follows (for a given discussion topic):

The user's perceptions of what is considered as a necessary (or required) environment and/or necessary outcome for the discussion topic (or derived substantially therefrom) so that the user perceives, or may choose to experience a greater motivation, either: (a) to initiate or to not abandon the discussion topic, or (b) to terminate activities related to the discussion topic.

Note, as an aside, the rationale for identifying "needs" as a motivational attribute for the fundamental category of "confidence" is that it is believed that a user's confidence, as related to a discussion topic, may be operably assessed by determining the degree to which the user's needs (related to the discussion topic) are perceived by the user as being accommodated or satisfied.

2.2. In one embodiment of the invention further described below, the above mentioned fundamental category of "patience" has an associated motivational attribute denoted "stress reactions", wherein "stress reactions" may be described as follows (for a given discussion topic):

The user's stress reactions related to the discussion topic (and/or outcomes therefrom) resulting from undesirable or unexpected conditions or circumstances created by the discussion topic (or substantially derived therefrom).

Note, as an aside, the rationale for identifying "stress reactions" as a motivational attribute for the fundamental category of "patience" is that it is believed that a user's patience, as related to a discussion topic, may be assessed by determining the degree to which the user's needs, not stress reactions, related to the discussion topic are perceived by the user as being accommodated or satisfied. In other words, when a user's needs (as related to a discussion topic) are being accommodated or satisfied then it is believed that a user's stress reactions are minimized or at least reduced within the discussion topic.

2.3. In one embodiment of the invention further described below, the above mentioned fundamental category of "devotion" has an associated motivational attribute denoted "interests" (denoted by the Birkman Method as "Organizational Strengths" which is not to be confused with the motivational attribute "strengths" as described in 2.4 below), wherein "interests" may be described as follows (for a given discussion topic):

The user's interests related to the discussion topic may be described as "active" or "inactive" within the discussion topic (and/or conditions arising that are related thereto). In particular, the present invention allows the user to explore ways to elicit, change or accept his/her interests (i.e., active or inactive) in the content of the discussion topic (or conditions arising that are related thereto).

Note, as an aside, the rationale for identifying "interests" as a motivational attribute for the fundamental category of "devotion" is that it is believed a user's devotion, as related to the discussion topic, may be assessed by determining the degree to which the user utilizes their interests as related to the discussion topic.

2.4. In one embodiment of the invention further described below, the above mentioned fundamental category of "honor" has an associated motivational attribute denoted "strengths" (denoted by the Birkman Method as "Usual" behavior), wherein "strengths" may be described as follows (for a given discussion topic):

The user's perceived strengths to the discussion topic (and/or outcomes therefrom) resulting in incorporating the user's usual strengths on conditions or circumstances created by the discussion topic (or substantially derived therefrom).

Note, as an aside, the rationale for identifying "strengths" as a motivational attribute for the fundamental category of "honor" is that it is believed a user's honor, as related to the discussion topic, may be assessed by determining the degree to which the user utilizes their strengths as related to the discussion topic. Also, it is believed that when a user's needs described in 2.1 above are being accommodated and satisfied it is more likely that a user's strengths are stimulated.

3. It is yet another aspect of this invention to gather a collection of descriptions of "attitudinal traits" (denoted as "attitudinal trait descriptions" herein) that represent what are believed to be descriptive of at least one idealized user, wherein such attitudinal trait descriptions are indicative of the idealized user's usual, default and/or preferred attitudes (and/or resulting behaviors) related to the motivational attributes described above for the corresponding fundamental categories also described above. Note that attitudinal trait descriptions for each motivational attribute may be substantially derived from an evaluation procedure, e.g., in conjunction with an expert in human cognitive perception as discussed above (however, it is worth noting that assistance with such evaluation procedures may also be substantially in written form or automated, e.g., via software, and may be provided via a network such as the Internet). Thus, for the motivational attribute "needs", there may be a collection of attitudinal trait descriptions that is consistent (e.g., statistically correspond) with a user's "user profile" that when these attitudinal traits are supported (e.g., provided, and/or satisfied), the user is generally deemed to have a healthy outlook toward a given discussion topic or life in general. Alternatively or optionally, when these attitudinal trait descriptions are not supported (e.g., not provided and/or not satisfied), the user is generally deemed to have an unhealthy mental state-of-mind or outlook of a given discussion topic or life in general. For the motivational attribute "needs" and its corresponding fundamental category "confidence", such "need" attitudinal trait descriptions may be, e.g.: needing plenty of time to make decisions, needing a busy schedule, or needing a definite plan in place to accomplish a task. In addition, if an idealized user is aware of such needs, then the user is more likely to discover ways to accommodate these needs within a discussion topic. Moreover, it is believed that the user's confidence will develop or evolve over time within a discussion topic in correspondence to increased awareness of such needs and discovering ways to accommodate these needs. Also, it is believed that the needs which are not like the user (i.e., needs "least like" the user) may also provide the user with valuable insight. In other words, when the user shows a "lack of motivation" to a particular need, it may be that the user has either a preference for, or dislike of others having a strong propensity for having such a need. Accordingly, by allowing the user to investigate his/her perceptions regarding such "lack of motivation", the user may gain useful personal insights. In particular, by presenting to the user presentations (e.g., questions, statements, etc.) such that various needs or attitudinal trait descriptions (which are different from those of the user), such different attitudinal trait descriptions can be explored by the user. Thus, the present invention may be used to help the user discover an increased awareness of not only his/her own needs or attitudinal trait descriptions as they relate to the user's discussion topic(s), but also very different needs or attitudinal trait descriptions of others. In addition, the present invention may also help the user to become aware of another's behaviors and/or attitudes (e.g., attitudinal trait descriptions) and attempt to give the user a perception of how another person may relate to their own environments within a given discussion topic. In at least one embodiment of the present invention and described in more detail in subsection four immediately below, a computational system (see Appendix A) classifies a collection of the user's "most extreme" attitudinal trait descriptions which are "most-like" and "least-like" the user. In other words, in one embodiment of the present invention, not all the user's attitudinal trait descriptions from the user profile or evaluation procedure are utilized, e.g., only those attitudinal trait descriptions are utilized which the computational system of this invention find as extreme for a given user as compared to other attitudinal trait descriptions.

4. It is another aspect of the Relationship Anatomy Model to classify such user's attitudinal trait descriptions described in subsection three immediately above. The design of the Relationship Anatomy Model in FIG. 30a shows at least four "quadrant caches" that represent a classification of the user's "most like" or "least like" attitudinal trait sets (e.g., set of attitudinal trait descriptions) for each motivational attribute and its corresponding fundamental category (e.g., "needs" and "confidence"). More particularly, such quadrants include a plurality of mutually exclusive classifications for the attitudinal trait descriptions, each such classification denoted herein as "set of attitudinal trait descriptions". Note that for describing the present invention, the arrangement or geometry disclosed in FIG. 30a through FIG. 30f is relied upon to simplify the description herein. However, such simplification should not be interpreted as a limitation of the invention. Indeed, there could be more or fewer than four quadrants in the Relationship Anatomy Model. For example, a user may only want to design one quadrant cache for every motivational attribute and fundamental category wherein the user desires to only focus on one classification of their attitudinal trait descriptions. In addition, a user may want to design a subset of quadrant caches for each of the four existing quadrant caches wherein each subset of quadrant caches classifies a "deeper" sense or description of the attitudinal trait description sets. In other words, there are an unlimited number of ways to define the "variables" within the structure of the Relationship Anatomy Model wherein variables represent words, terms, and phrases that may change depending on the user's preferences when defining such variables with the facilitator. The following description explains the classification of the user's sets of attitudinal trait descriptions within the Relationship Anatomy Model design in FIG. 30 through FIG. 30f. As stated above, these figures are provided to simplify the description herein. Also, it may be important to note that the Relationship Anatomy Model design is incorporated within the Linguistic Constructs Table in FIG. 29, and it may help to understand the Linguistic Constructs Table Detailed Description section before proceeding. Accordingly, the reader may wish to review the subsection of the Detailed Description hereinbelow entitled "Detailed Description Of The Linguistic Constructs Table". In FIG. 30a, the quadrant caches are represented two-dimensionally by two axes, wherein the "y" or vertical axis represents a range of user awareness regarding the attitudinal trait descriptions, and in particular, as such attitudinal trait descriptions relate to a discussion topic that a user is exploring via the present invention. Thus, this awareness range is from a user "high" awareness to a user "low" awareness. Alternatively the "x" or horizontal axis represents a range of user perceptions of the attitudinal trait descriptions, wherein the range extends from those attitudinal traits most (or more) like the user (herein denoted "most like" for simplicity) to those attitudinal trait descriptions least (or less) like the user (herein denoted "least like" for simplicity). The user of the system classifies the sets of attitudinal trait descriptions via the USER PROFILE 9 component in FIG. 2 through the MOTIVATION EQUALIZER 11 component in FIG. 2 and the MOTIVATION AMPLIFIER 12 component in FIG. 2 (refer to the Brief Descriptions Of The Components section of this application for more information regarding these components). In particular, for the given motivational attribute (also denoted as "ATT" herein) and its corresponding fundamental category (also denoted as "CAT" herein) and its associated attitudinal trait descriptions (denoted as "X" below), at least the following quadrant caches are applicable:

Quadrant 1 Cache: A quadrant whereby the user has a relatively "low" awareness of an instance of the attitudinal trait description(s) X in the context of the discussion topic, and the attitudinal traits represent instances that are "most like" the user.

Quadrant 2 Cache: A quadrant whereby the user generally has "high" awareness of an instance of the attitudinal trait description(s) X in the context of the discussion topic, and the attitudinal trait(s) represent instances that are "most like" the user.

Quadrant 3 Cache: A quadrant whereby the user generally has "low" awareness of an instance of the attitudinal trait description(s) X in the context of the discussion topic, and the attitudinal trait(s) represent instances that are "least like" the user.

Quadrant 4 Cache: A quadrant whereby the user generally has "high" awareness of an instance of the attitudinal trait description(s) X in the context of the discussion topic, and the attitudinal trait(s) represent instances that are "least like" the user.

Also, referring to FIG. 31 a different view of the Relationship Anatomy Model is illustrated that shows the results of classifications or sets of attitudinal trait descriptions. Each set of attitudinal trait descriptions is classified by a triplet for each quadrant cache (e.g., A.1.1 is an example of such a triplet), wherein the first coordinate of the triplet identifies the fundamental category (e.g., A, B, C, or D), the second coordinate of the triplet identifies the column (e.g., column 1 or column 2), and the third coordinate of the triplet identifies the quadrant cache (e.g., 1, 2, 3, or 4). For example, within quadrant 1 cache (e.g., sets of attitudinal trait descriptions wherein the user has identified them as "most like" himself and having a "lower" awareness thereof) the set is identified as A.1.1. The first coordinate of the triplet, "A", represents the fundamental category (e.g., "confidence"), the second coordinate of the triplet, "1", represents the column number (e.g., "column 1" which indicates that these attitudinal trait are most like the user), and the third coordinate of the triplet, "1", represents the quadrant cache (e.g., "quadrant 1 cache"). Note that each set of attitudinal trait descriptions are "locked" to a specific quadrant cache and within a specific fundamental category and motivational attribute. However, as described in section 6.5 hereinbelow, when describing the operation of motivational coping techniques, depending on the results of a user discussion topic evaluation, a motivational coping technique (e.g. "allow") may represent a set of attitudinal trait descriptions in either column 1 (e.g., A.1.1) or column 2 (e.g., A.2.3). Therefore, the motivational coping technique may represent one set of attitudinal trait descriptions for one discussion topic while representing another for a different discussion topic. This logic will become more apparent as one appreciates the scope of this invention.

5. It is another aspect of the Relationship Anatomy Model in FIGS. 30b through 30f that there are at least two types of "states of mind" for each fundamental category and its corresponding motivational attribute. These two types are "passive" (e.g., suggesting less effort) and "active" (e.g., suggesting more effort) states of mind. In one embodiment of the present invention, the user assigns descriptions for each of these "states of mind". These descriptions are derived from the STATE OF MIND CONSTRUCTOR 8 component in FIG. 2 and are utilized by the DISCUSSION GENERATOR 5 component in FIG. 4 of the present invention as part of the inquires generated (as discussed in more detail hereinbelow). The 'states of mind" descriptions are obtained through conducting dialogue exercises or interactions with the user. In most cases, these exercises should be performed with a trained professional or expert. For example, one exercise that a user may be requested to perform requests a user to meditate on a script or presentation that relaxes the user and results in a "passive" state of mind description. Based on the user's experience in this exercise, the user provides a list of one-word descriptions that represent his/her "passive" experience (e.g., words such as: creativity, clarity, and satisfaction). In addition, the user may perform another exercise that results in the user entering a state of mind where the user re-visits a highly motivated and/or positive experience; i.e., the user enters an "active" state of mind. Based on the user's experience in this exercise, the user provides a list of one-word descriptions that represent his/her "active" experience (e.g., words such as: freedom, vitality and connecting). Generally, in one embodiment of the present invention, a list or set of three or more one-word descriptions are provided for each such state of mind. However, phrases and/or pictures may also be identified by the user as being indicative of a particular state of mind. Moreover, additional/alternative states of mind may be incorporated into an embodiment of the invention. For example, active and passive states of mind may be subdivided into the following. For the active state of mind, two substrates: active for avoidance, and active for pursuing. For the passive state of mind: passive from fear, passive from indifference, and passive from pleasure.

For the purpose of leading the reader into subsection six immediately below regarding motivational coping techniques and how these techniques operate within the Relationship Anatomy Model, it is assumed that for a given fundamental category within a particular discussion topic, the "passive" state of mind motivational coping techniques will either represent the user's "most like" attitudinal trait descriptions (i.e., quadrant cache 1 and quadrant cache 2 denoted as "Column 1" herein) or the user's "least like" attitudinal trait descriptions (i.e., quadrant cache 3 and quadrant cache 4 denoted as "Column 2" herein) but never both at one time. Conversely, the "active" state of mind motivational coping techniques will either represent the user's "most like" attitudinal trait descriptions (i.e., quadrant cache 1 and quadrant cache 2 denoted as "Column 1") or the user's "least like" attitudinal trait descriptions (i.e., quadrant cache 3 and quadrant cache 4 denoted as "Column 2") but never both at one time. In other words, an "active" state of mind will represent either Column 1 or Column 2, but an "active" state of mind will never overlap portions of the description in both columns at the same time for a given fundamental category within a particular discussion topic. That is, when the "active" state of mind represents Column 1 then the "passive" state of mind will represent Column 2.

Conversely, when the "passive" state of mind represents Column 1 then the "active" state of mind will represent Column 2. A further description of how the "passive" and "active" states of mind are processed in the Relationship Anatomy Model becomes more apparent in subsection six immediately below when motivational coping techniques are assigned to each state of mind type (e.g., "passive" and "active") for each fundamental category. In addition, the use of this logic is explained in more detail in the Detailed Description Of The Invention section of this application.

6. It is yet another aspect of the Relationship Anatomy Model represented in FIGS. 30a through 30f that within the MOTIVATIONAL COPING TECHNIQUES CONSTRUCTOR 15 in FIG. 3, one or more "motivational coping techniques" are defined by the facilitation process. Thus, in addition to a motivational coping technique being a verb or verb phrase specifically tailored to communicate the characteristics of a fundamental category to the user, each such motivational coping technique may represent a "passive" state of mind (e.g., suggesting less effort), or an "active" state of mind (e.g., suggesting more effort) when attempting to address (or not address) the attitudinal trait descriptions of the given motivational attribute and its corresponding fundamental category within the context of a particular discussion topic. For example, a user may practice (or desire to practice) a motivational coping technique such as "support" in a context related to supporting the user's spouse. Accordingly, by interacting with present invention, wherein the discussion topic is, e.g., the user's relationship with his/her spouse, the user may discover ways to "support" (e.g., an "active" state of mind motivational coping technique for the fundamental category "confidence"; see FIG. 30b) his/her spouses needs which is assumed to thereby improve the personal quality of "confidence" or trust in the relationship with his/her spouse. Referring to the fundamental category of "confidence", there may be four such motivational coping techniques (two "passive" state of mind coping techniques and two "active" state of mind coping techniques) for addressing the user's "need" attitudinal trait descriptions (i.e., "need" is the motivational attribute for the fundamental category "confidence"). Although the remainder of this section describes how a facilitator may define certain motivational coping techniques through the use of the MOTIVATIONAL COPING TECHNIQUE CONSTRUCTOR 15 component in FIG. 3, the facilitator is encouraged to work with the user to help define these verbs and/or verb phrases. For example, for the motivational coping techniques for the fundamental category "confidence" may be described as follows:

6.1. In FIG. 30b, a "passive" state of mind motivational coping technique is defined as "allow", wherein this motivational coping technique may be given the following meaning: The user may develop confidence in a particular topic of discussion by "allowing" a "most like" (alternatively, "least like") personal user need. Thus, where the discussion topic is, e.g., the user's relationship with his/her spouse, the "allow" motivational coping technique may be used by the present invention to generate and display the following inquiry:

"Which of your needs below would you (i.e., the user) allow regarding the relationship with your spouse? Explain."

"Plenty of time for complex decisions"

To which the user might respond:

I need my spouse to allow me time to think about complex situations. In other words, if I respond too quickly I have a tendency to change my mind. And I remember from past situations that when I change my mind, my spouse becomes frustrated with me.

NOTE: only a portion of the immediately above inquiry and attitudinal trait descriptions used in generating this inquiry are shown for the purpose of explaining how this inquiry can be generated by the invention. Notice that the location of the "allow" motivational coping technique in quadrant 1 cache of FIG. 30f. You will find the attitudinal trait description, "Plenty of time for complex decisions", displayed in quadrant 1 cache under the label A.1.1 (a detailed explanation of this label is explained in number 4 above) in FIG. 31 (a different representation of the Relationship Anatomy Model showing the results of classifications of attitudinal trait descriptions for each fundamental category). Also, as discussed in number 4 above, note that attitudinal trait descriptions are "locked" to a specific quadrant cache. However, as discussed in number 6.5 below, since the motivational coping techniques are assigned to states of mind (e.g., "passive" and "active"), they may switch from column 1 to column 2, representing different sets of attitudinal trait descriptions within for different quadrant caches, or visa versa depending on the results of a user's discussion topic evaluation. This logic applies the same for 6.2 through 6.4 and further explanation is provided throughout this application.

6.2. In FIG. 30b, a "passive" state of mind motivational coping technique defined as "accept" is shown, wherein this motivational coping technique may be given the following meaning: The user may develop confidence in a particular topic of discussion by "accepting" a "most like" or "least like" the user need instance. Thus, where the discussion topic is, e.g., the user's relationship with his/her spouse, the "accept" motivational coping technique may be used by the present invention to generate and display the following inquiry:

"Which of your most important needs below would you (i.e., the user) accept regarding the relationship with your spouse? Explain."

Plenty of different calls on attention

To which the user might respond:

I feel comfortable having a lot going on around me. My spouse may benefit in our relationship if he/she understood that I don't mind working with activity going on around me. In other words, I don't have to have complete silence for long periods of time while working.

6.3. In FIG. 30b, an "active" state of mind motivational coping technique defined as "maintain", wherein this motivational coping technique may be given the following meaning: The user may develop confidence in a particular topic of discussion by "maintaining" a "most like" or "least like" the user need instance. Thus, where the discussion topic is, e.g., the user's relationship with his/her spouse, the "maintain" motivational coping technique may be used by the present invention to generate and display the following inquiry:

"How can you maintain others potential needs below regarding the relationship with your spouse? Explain."

Personal control over scheduling

To which the user might respond:

In some cases, my spouse may benefit if I maintain some of my own schedule. However, it may benefit my relationship with my spouse if I show more effort in supporting his/her need to have personal control over scheduling.

6.4. In FIG. 30b, an "active" state of mind motivational coping technique defined as "support", wherein this motivational coping technique may be given the following meaning: The user may develop confidence in a particular topic of discussion by "supporting" a "most like" or "least like" the user need instance. Thus, where the discussion topic is, e.g., the user's relationship with his/her spouse, the "support" motivational coping technique may be used by the present invention to generate and display the following inquiry:

"How can you support others potentially important needs below regarding the relationship with your spouse? Explain."

An unemotional environment

To which the user might respond:

I believe it may help the relationship with my spouse if I can control my emotions in certain situations. Personally, I don't have a "need" for an unemotional environment, however, others who have this need (and my spouse may be one of these people) might appreciate less emotion in certain situations.

6.5. Note that in FIG. 30b, each such coping technique (i.e., verb and/or verb phrase) can be classified by a triplet for each quadrant cache, wherein the first coordinate of the triplet identifies the fundamental category, the second coordinate of the triplet identifies whether the user associates the motivational coping technique with an active or a passive state of mind, and the third coordinate of the triplet identifies whether the user has a high or low awareness of his/her use of the coping technique. Thus, assuming: (i) for the first coordinate of the triplet, "A" represents the fundamental category (e.g., "confidence"), (ii) for the second coordinate of the triplet, "P" represents a passive state of mind, and "A" represents an active state of mind, and (iii) for the third coordinate of the triplet, "L" represents a low awareness level and "H" represents a high awareness level, in one embodiment of the invention, the above identified motivational coping techniques for the fundamental category of "confidence" can be classified as follows: (1) for the allow coping technique: A.P.L. (2) for the accept coping technique: A.P.H, (3) for the maintain coping technique: A.A.L, and (4) for the support coping technique: A.A.H. Also, referring to FIG. 30b and described in number 5 above, for the given motivational attribute and its corresponding fundamental category, motivational coping techniques can be "linked" according to a common value for the second coordinate of the triplet. For example, assuming the "allow" motivational coping technique (in one embodiment of the invention) is classified as (A, P, L), and the "accept" motivational coping technique is classified as (A, P, H), then these two coping techniques are said to be "linked", and these two coping techniques describe the coping techniques for the user and the fundamental category of "confidence" when in a "passive" state of mind (representing the second coordinate of the triplet). In other words, these motivational coping techniques will always represent the fundamental category "Confidence" and the "Passive" state of mind. However, depending on how a user ranks a discussion topic in the discussion topic evaluation within DISCUSSION GENERATROR 5 component in FIG. 4, this set of motivational coping techniques may represent either Column 1 (e.g., Quadrant Caches 1 & 2) attitudinal trait description sets or Column 2 (e.g., Quadrant Caches 3 & 4) attitudinal trait description sets, but never both at one time. The following describes the motivational coping techniques in FIG. 30b for the motivational attribute "needs" and its corresponding fundamental category "confidence":

(A.P.L) Allow (defined as: to let do or happen; permit): A motivational coping technique whereby the user has a relatively low awareness (in comparison to most users) of a particular instance of a "need" in the context of the discussion topic, and the user is "passive" (e.g., suggesting less effort) toward this need instance (i.e., the user is generally not initiating activities to address the low awareness/passive instance). Accordingly, the user may "allow" the need instance to go unmet even if the need instance were recognized. Depending on how a user rates the DISCUSSION TOPIC EVALUATION 19 in FIG. 4 for a discussion topic, this motivational coping technique will either represent the attitudinal trait descriptions in quadrant 1 cache (e.g., A.1.1 in FIG. 31) or quadrant 3 cache (e.g., A.2.3 in FIG. 31). This will be demonstrated in the example given in the Detailed Description Of The Invention.

(A.P.H) Accept (defined as: to receive, especially with gladness or approval): A motivational coping technique whereby the user is more aware of a particular instance of a "need" in the context of the discussion topic and the user is also "passive" (e.g., suggesting less effort) toward the instance (i.e., the user is generally not initiating activities to address the more aware/passive instance). Accordingly, the user is more cognizant of the need instance, but may "accept" circumstances or events of the discussion topic where the need instance is unmet. Depending on how a user rates the DISCUSSION TOPIC EVALUATION 19 in FIG. 4 for a discussion topic, this motivational coping technique will either represent the attitudinal trait descriptions in quadrant 2 cache (e.g., A.1.2 in FIG. 31) or quadrant 4 cache (e.g., A.2.4 in FIG. 31). This will be demonstrated in the example given in the Detailed Description Of The Invention.

(A.A.L) Maintain (defined as: to keep up or carry on; continue): A motivational coping technique whereby the user has a relatively low awareness (in comparison to most users) of one or more particular instances of a "need" in the context of the discussion topic and "active" (e.g., suggesting more effort) toward the instance (i.e., the user is generally initiating activities to address the low awareness/active instance). Accordingly, the user is likely to not recognize the particular need instance related to the discussion topic, but is likely to "maintain" such an instance when recognized. Depending on how a user rates the DISCUSSION TOPIC EVALUATION 19 in FIG. 4 for a discussion topic, this motivational coping technique will either represent the attitudinal trait descriptions in quadrant 1 cache (e.g., A.1.1 in FIG. 31) or quadrant 3 cache (e.g., A.2.3 in FIG. 31). This will be demonstrated in the example given in the Detailed Description Of The Invention.

(A.A.H) Support (defined as: to keep from weakening or failing; strengthen): A motivational coping technique whereby the user is more aware of a particular instance of a "need" in the context of the discussion topic and "active" (e.g., suggesting more effort) toward the instance (i.e., the user is generally initiating activities to address the more aware/active instance). Accordingly, the user is likely to recognize the particular need instance related to the discussion topic and is likely to "support" such an instance when recognized. Depending on how a user rates the DISCUSSION TOPIC EVALUATION 19 in FIG. 4 for a discussion topic, this motivational coping technique will either represent the attitudinal trait descriptions in quadrant 2 cache (e.g., A.1.2 in FIG. 31) or quadrant 4 cache (e.g., A.2.4 in FIG. 31). This will be demonstrated in the example given in the Detailed Description Of The Invention Note that for one embodiment of this invention, a user may perform an "allow" motivational coping technique on one set of need attitudinal trait descriptions, perform an "accept" motivational coping technique on another set of need attitudinal trait descriptions, perform a "maintain" motivational coping technique on yet another set of need attitudinal trait descriptions, and/or perform a "support" motivational coping technique on yet another set of need attitudinal trait descriptions. Thus, there may be a first collection of need attitudinal trait descriptions (for the fundamental category "confidence") that is descriptive of a first set of needs wherein the user uses an "allow" motivational coping technique to accommodate or address the need attitudinal traits of this first set. There may be a second collection of attitudinal trait descriptions (for the fundamental category "confidence") that is descriptive of a second set of need attitudinal trait descriptions wherein the user uses an "accept" motivational coping technique to address needs of this second set. There may be a third collection of attitudinal trait descriptions (for the fundamental category "confidence") that is descriptive of a third set of needs wherein the user uses a "maintain" motivational coping technique to address needs of this third set. Finally, there may be a fourth collection of attitudinal trait descriptions (for the fundamental category "confidence") that is descriptive of a fourth set of needs wherein the user uses a "support" motivational coping technique to address needs of this fourth set.

Moreover, note that the motivational coping technique "allow" may be the preferred user motivational coping technique for addressing one set of need attitudinal trait descriptions during one discussion topic evaluation (via interacting with the discussion generator of the present invention) but this motivational coping technique may be the preferred user coping technique for a different set of need attitudinal trait descriptions for another discussion topic evaluation. However, for one discussion topic evaluation, one motivational coping technique will never represent more than two different sets of attitudinal trait descriptions and one motivational coping technique will be assigned either a "passive" or "active" state of mind type, never both. Also note that within the MOTIVATIONAL COPING TECHNIQUE CONSTRUCTOR 15 in FIG. 3, the motivational coping techniques are designed in a way that demonstrate a maturity level within both the "passive" and "active" states of mind. Referring to FIG. 30b for instance, (A.P.L) "Allow" and (A.P.H) "Accept" will always be defined as "passive" (e.g., suggesting less effort) states of mind as described in 6.5 above. (A.P.L) "Allow" represents attitudinal trait descriptions in which the user has a lower awareness and (A.P.H) "Accept" represents attitudinal trait descriptions in which the user has a higher awareness. Therefore, (A.P.L) "Allow" is the first evolution of maturity and (A.P.H) "Accept" is the second evolution of maturity. In other words, before the user "Accepts" a "need" instance, it is believed through experimentation and observation that the user will first "Allow" a "need" instance. Refer to the Detailed Description Of The Coping Evolution Requirements section of this application for more information regarding the defining of "passive" and "active" motivational coping techniques.

The Fundamental Categories, Motivational Attributes, Motivational Coping Techniques, and Attitudinal Trait Descriptions described above in section A are organized and populated in a "passive" construct and an "active" construct in a structure called the Linguistic Constructs Table in FIG. 29 that is processed by the LINGUISTICS ORGANIZER 17 of the DISCUSSION GENERATOR 5 in FIG. 4.

FIG. 29 shows the Linguistic Constructs Table. It is described in detail in the Detailed Description Of The Linguistic Constructs Table and demonstrated extensively in the Detailed Description Of This Invention. However, in general, depending on how a user evaluates a discussion topic (described in section B below), the data designed in the Linguistic Constructs Table are organized in two ways to accommodate a "passive" and "active" state of mind. The first way is where the "passive" motivational coping techniques are designed to represent column 1 in FIG. 30f and the "active" coping techniques are designed to represent column 2 in FIG. 30f. The second way is where the "passive" coping techniques are designed to represent column 2 in FIG. 30f and the "active" coping techniques are designed to represent column 1 in FIG. 30f. In other words, the motivational coping techniques are pre-designed in the Linguistic Constructs Table to switch columns depending on a user's discussion topic evaluation. Therefore, as a result of evaluating a discussion topic, the Linguistic Constructs Table must organize "passive" (e.g., suggesting less effort) and "active" (e.g., suggesting more effort) motivational coping techniques in such a way wherein they represent sets of attitudinal trait descriptions (refer to FIG. 31) as a way of coping with them "passively" and "actively". In other words, depending on a user's discussion topic evaluation, one set of attitudinal trait descriptions may be generated in an inquiry by either a "passive" motivational coping technique or an "active" motivational coping technique.

The content of the Linguistic Constructs Table is developed by the facilitator (the facilitator is also encouraged to work with the user of this system to aid in designing and/or confirming the content) of this system through the MOTIVATION MANAGER 3 component in FIG. 2 and the MINDSET DEVELOPER 4 component in FIG. 3 and it is used as the primary source for generating inquiries through the DISCUSSION GENERATOR 5 component in FIG. 4. The following description in section B below describes the operation of the DISCUSSION GENERATOR 5 component in FIG. 4 as it relates to the content in the Linguistic Constructs Table.

Section B describes the mechanics of the invention as it relates to how a user interacts with this system in everyday situations, relationships, or aspects of general life (e.g., discussion topics). Accordingly, it is an aspect of the DISCUSSION GENERATOR 5 component in FIG. 4 of the present invention to generate inquiries, within a context personalized both to the user's attitudinal trait descriptions (e.g., behaviors or attitudes) and to the user specified discussion topic within the DISCUSSION TOPIC EVALUATION 19 in FIG. 4, so that the user can investigate, reflect upon, and/or gain greater insight into his/her perceptions of the discussion topic while relating to the attitudinal trait descriptions via the pre-defined motivational coping techniques for each pre-defined fundamental category. In other words, the discussion generator generates, for each of one or more predetermined fundamental categories, inquiries directed to assisting the user to cope with and/or gain greater insight into his/her a "most like" or "least like" attitudinal trait descriptions of the fundamental category as it relates to the discussion topic, wherein these inquiries are phrased in a manner that is believed to cause the user, when reflecting on the inquiries, to examine the discussion topic from a particular (e.g., user motivated) perspective from which the user might not otherwise readily be able to recognize. Put more simply, asking the right inquiries can help users discover some personal answers to an issue or situation (e.g., a discussion topic).

It is another aspect of this invention to define a user specified discussion topic, evaluate the discussion topic, and generate inquiries back to the user for a user's consideration in a manner that is customized to the user. The sequential process of the DISCUSSION GENERATOR 5 in FIG. 4 is described in 1 through 3 below:

1. Before a user evaluates a Discussion Topic in the DISCUSSION TOPIC EVALUATION 19 in FIG. 4, a user must define a discussion topic to evaluate in which a user would like to investigate. Simply, the user defines a discussion topic by completing the phrase, "I want to focus this discussion on my . . . " (refer to FIG. 48). For example, a discussion topic may be "relationship with Karen", "marriage", "family", "health", "work", "relationship with my boss", "fun and recreation", "children", "self", etc. Once a discussion topic is defined (as in FIG. 48, let's say the user defines a discussion Topic as "relationship with Karen"), it is evaluated by the user in the DISCUSSION TOPIC EVALUATION 19 in FIG. 4. For each Fundamental Category (e.g., Confidence, Patience, Devotion, and Honor) one or more true/untrue statements are designed to support each Fundamental Category (refer to FIG. 48). Each of these true/untrue statements require a three step process wherein each true/untrue statement requires a rank of 1 to 10, a confidence level indication, and a response type indication described in 1.1 through 1.3 below (refer to FIG. 48):

1.1. The user ranks each true/untrue statement from 1 to 10 where 1 represents an untrue (e.g., assuming a poor perspective) representation of the true/untrue statement and a 10 represents a true (e.g., assuming a good perspective) representation of the true/untrue statement. For one embodiment of this application, there is one true/untrue statement for each fundamental category. Referring to FIG. 48 for example, a true/untrue statement is created which supports the fundamental category "confidence" (e.g., statement number 1 in portion B of FIG. 48). The true/untrue statement reads (refer to 1.1 in section A above for the definition of confidence): "I have 100% complete trust and faith regarding my . . . relationship with Karen". Each true/untrue statement is designed in the same manner for any discussion topic defined by a user. For example, if a user ranks this true/untrue statement a 1 then he/she is saying that he/she does not have trust and faith regarding their relationship with Karen (i.e., assumes a poor perspective). Conversely, if a user ranks this true/untrue statement a 10 then he/she is saying that he/she does have trust and faith regarding their relationship with Karen (e.g., assumes a good perspective). A rank of 1 through 5 represents a poor ranking range and 6 through 10 represents a good ranking range for each true/untrue statement. The true/untrue statements defined for the remaining fundamental categories in one embodiment of this application are:
(refer to 1.1 in section A above for the definition of each fundamental category)
Patience: "I easily endure hardships with calmness regarding my . . . <discussion topic>".
Devotion: "I am completely devoted and interested regarding my . . . <discussion topic>".
Honor: "I have high respect for everything regarding my . . . <discussion topic>".

1.2. Additionally, the user is required to indicate a confidence level of "high" or "low" for each true/untrue statement (not to be confused with the fundamental category "confidence") which is indicative of the user's confidence in their ranking of a true/untrue statement. For example, if the user feels they are saying that a 7 is the rank of a given true/untrue statement but they are unsure of the accuracy of the rank then they would indicate a "low" confidence level in their answer. Generally, a guess in the ranking of a true/untrue statement would indicate a "low" confidence level. Conversely, if the user feels confident in their ranking of 7 then they would indicate a "high" confidence level. A "low" confidence level indicator, along with an "improve" response type (as discussed in 1.3 below), allows a user to receive an inquiry from the discussion generator which contain sets of attitudinal trait descriptions wherein the user has previously indicated a higher awareness. This assures that a user will receive inquiries wherein the user will have the easiest chance of discovering answers when investigating a given discussion topic.

1.3. Moreover, as shown in FIG. 48, before the user can submit their discussion topic evaluation for the given discussion topic (e.g., relationship with Karen), the user is required to indicate the desired response type of "empower" or "improve" for each true/untrue statement which is indicative of how the user prefers to investigate or receive inquiries regarding the discussion topic being evaluated. For example, as discussed in more detail in number 2 below and described in the Detailed Description Of The Invention, for each true/untrue statement, an "empower" response type will generate an inquiry back to the user that is indicative of the user's strongest perception (e.g., highest sub-ranked quadrant cache as described in 2 below) of the discussion topic being evaluated. Conversely, an "improve" response type will generate an inquiry back to the user that is indicative of the user's weakest perception (e.g., lowest sub-ranked quadrant cache as described in 3 below) of the discussion topic being evaluated.

2. When a discussion topic evaluation is complete, the user is required to submit it which stores the record in a data structure. When it is submitted, an algorithm called the response algorithm uses the rank for a given true/untrue statement as described in 1.1 of section B above and the confidence level indicator for the given true/untrue statement described in 1.2 of section B above to calculate a sub-rank for each of the four quadrant caches for each fundamental category as described in number 4 of section A (e.g., In one embodiment of the present invention, four quadrant caches represent each fundamental category). The result of how the quadrant caches are sub-ranked will reflect how the user perceives the discussion topic being evaluated at the given time for a given fundamental category (e.g., "confidence"). In other words, the rank for every true/untrue statement in the discussion topic evaluation (e.g., fundamental category) is used by the response algorithm to populate a sub-rank in each of the four quadrant caches of its corresponding fundamental category (which also represents the corresponding motivational attribute [e.g., needs] and each quadrant cache set of attitudinal trait descriptions). A detailed example of how the response algorithm populates each quadrant cache for every true/untrue statement (e.g., fundamental category) is described in the Detailed Description Of The Invention.

3. Next, the user may now investigate the discussion topic (e.g., relationship with Karen) which has been evaluated through the DISCUSSION TOPIC EVALUATION 19 component in FIG. 4. When the user requests to discuss a specific discussion topic (refer to FIG. 49), the RESPONSE MANAGER 20 component in FIG. 4 is activated. The RESPONSE MANAGER 20 component analyzes the results of the discussion topic evaluation for every fundamental category (e.g., only the fundamental category of "confidence" is described in this example) and determines the criteria necessary for generating an inquiry back to the user. The RESPONSE MANAGER 20 component determines the location of the "active" state of mind based on the result of the response algorithm, and once the active state of mind is determined, the "passive" state of mind can subsequently be determined. Next, the RESPONSE MANAGER 20 component determines (as the criteria) the primary motivational coping technique (e.g., Accept in this case as shown in FIG. 50) based on the user's request for an "improve" response type (as indicated for true/untrue statement number 1 in FIG. 48). Once the criteria is determined by the RESPONSE MANAGER 20 component in FIG. 4, it (i.e., the criteria) is passed to the LINGUISTICS ORGANIZER 17 component in FIG. 4 to locate the specific record in the Linguistic Constructs Table in FIG. 29 necessary for building the inquiry that is generated back to the user for the given fundamental category (e.g., confidence). Next, the INQUIRY BUILDER 18 component in FIG. 4 uses the data from the Linguistic Constructs Table to assemble the inquiry so that it makes sense to the user when it is presented (e.g., "passive" and "active" inquiries must be assembled differently to make sense to the user). Last, the PRESENTATION CONSTRUCTOR 21 component in FIG. 4 presents the inquiry to the user for the user to investigate. For the example presented in this section (refer to FIG. 50), the inquiry generated for the fundamental category "confidence" for this discussion topic (e.g., relationship with Karen) would read (a more detailed description of how this inquiry is built and presented is discussed in the Detailed Description Of The Invention section):
"Which of others potentially important needs below would you accept in a way that encourages creativity, clarity, and satisfaction toward your relationship with Karen? Explain."
an unemotional environment
an environment based on trust
issues reduced to their simplest form You'll notice the data for the inquiry above came from record #20 in FIG. 29 (e.g., the Linguistic Constructs Table) and the set of attitudinal trait descriptions that is called from the Linguistic Constructs Table (e.g., identified as A.2.4QCache4 under the column labeled "Attitudinal Trait Description ID") is shown in FIG. 31 under the label A.2.4 in the Quadrant 4 Cache.

B. This final section of the Summary Of The Invention describes the mechanics of the invention as it relates to documenting and reporting the user's experiences of the user's discussion topics and the user's autobiography. There are three processes of the DOCUMENTATION MANAGER 6 component in FIG. 5 described in 1 through 3 below:

1. It is an aspect of the present invention to document a user's answers to the inquiries generated by the DISCUSSION GENERATOR 5 component in FIG. 4 based on discussion topics evaluated in the DISCUSSION TOPIC EVALUATION 19 in FIG. 4. For example, for every inquiry generated (as described in number 3 of section B) the user is expected to formulate an answer and enter the answer into an electronic journal which stores the answer in a data structure wherein it is linked to the inquiry generated for a specific discussion topic. For example, referring to FIG. 50, a user would enter a journal entry (e.g., which reads, "I would create a journal entry based on the inquiry given regarding my relationship with Karen) in the electronic journal provided based on the inquiry presented for the given fundamental category (e.g., confidence) within the related discussion topic (e.g., relationship with Karen).

2. It is yet another aspect of the present invention to generate autobiography statements (not to be confused with the true/untrue statements in a discussion topic evaluation described in number 1 of Section B) from the LINGUISTIC ORGANIZER 17 component in FIG. 4 for every set of attitudinal trait descriptions defined in each quadrant cache for every fundamental category to develop a user's autobiography. The component which processes the user's autobiography is the AUTOBIOGRAPHY DEVELOPER 25 component in FIG. 5. NOTE: Each set of attitudinal trait descriptions are derived from the USER PROFILE 9 component in FIG. 2 and classified by the MOTIVATIONAL EQUALIZER 11 component in FIG. 2 and MOTIVATIONAL AMPLIFIER 12 component in FIG. 2. Also NOTE: In one embodiment of the present invention, a motivational coping technique (e.g., allow) may represent one of two sets of attitudinal trait descriptions (refer to FIG. 30b and note that the motivational coping techniques "allow" AND "maintain" may represent a set of attitudinal trait descriptions either in Quadrant 1 Cache or Quadrant 3 Cache [e.g., the lower awareness Quadrant Caches]) depending on how a user evaluates a discussion topic through a discussion topic evaluation. However, autobiography statements generated for the autobiography are not based on a discussion topic evaluation which supplies the discussion generator with criteria to specify a particular motivational coping technique (as described in number 3 of Section B above) to one set of attitudinal trait descriptions stored in a quadrant cache (e.g., either the "passive" or "active" motivational coping technique). Since the AUTOBIOGRAPHY DEVELOPER 25 component is not dependent on a discussion topic evaluation, the AUTOBIOGRAPHY DEVELOPER 25 utilizes both possible motivational coping techniques in each autobiography statement for each set of attitudinal trait descriptions shown in FIG. 31 (e.g., allow and maintain in FIG. 30b motivational coping techniques would represent both sets of attitudinal trait descriptions labeled A.1.1 and A.2.3 in FIG. 31 for the fundamental category "confidence" where as accept and support in FIG. 30b motivational coping techniques would represent both sets of attitudinal trait descriptions labeled A.1.2 and A.2.4 in FIG. 31 for the fundamental category "confidence"). This design is also represented in the Linguistic Constructs Table in FIG. 29. For simplicity, let's focus just on the set of attitudinal trait descriptions for A.1.1 shown in FIG. 31. The AUTOBIOGRAPHY DEVELOPER 25 component in FIG. 5 begins by searching the Linguistic Constructs Table in FIG. 29 under the Attitudinal Trait Description ID label for A.1.1QCache1. In one embodiment of this application, the computational system knows it can find at least two references in the table for A.1.1QCache1 (e.g., since two motivational coping techniques may represent one quadrant cache). Note in FIG. 29 that record #1 represents the motivational coping technique "allow" in the column labeled Motivational Coping Technique and the set of Attitudinal Trait Descriptions in the column labeled Attitudinal Trait Description ID is identified as A.1.1QCache1. Also note that in record #17 represents the motivational coping technique "maintain" in the column labeled Motivational Coping Technique and the set of Attitudinal Trait Descriptions in the column labeled Attitudinal Trait Description ID is identified as A.1.1QCache1. As a result, there are two references to A.1.1QCache1 for both motivational coping techniques allow and maintain. Therefore, in one embodiment of this application, there are two possible motivational coping techniques that may represent each Quadrant Cache. An example of an autobiography statement generated for the user's autobiography for the set of attitudinal trait descriptions under the label A.1.1 for Quadrant 1 Cache in FIG. 31 is presented as follows (the following autobiography statement along with the set of attitudinal trait descriptions is also shown in autobiography statement #3 in FIG. 44):

Describe ways you allow or maintain your needs:
1. plenty of time for complex decisions
2. a busy schedule
3. only an outline to follow Next, the user is expected to formulate an answer and enter the answer into a data structure wherein the answer is linked to the autobiography statement, which is generated for the user's autobiography. As you will see in number 3 below, a report of the user's autobiography may be generated which assembles the user's answers into sections based on each fundamental category (refer to FIG. 28)

3. It is yet a final aspect of the present invention to generate reports of the user's journal entries (e.g., answers related to discussion topics and the user's autobiography) through the REPORT MANAGER 24 in FIG. 5. There are three reports available in one embodiment described in this invention (refer to FIG. 54). The first report allows a user to review journal entries a specific discussion topic called View Discussion Report (refer to FIG. 26). A second report is available wherein the user is allowed to review journal entries of a specific fundamental category in a range (e.g., a date range) of previously evaluated discussion topics called View Category Report (see FIG. 27). A third report called the Autobiography Report (see FIG. 28) allows the user to review their autobiography entries.

Other features and benefits of the present invention will become evident from the accompanying drawing and the Detailed Description of the Invention hereinbelow.

BRIEF DESCRIPTION OF THE DRAWINGS

FIGS. 6A and 6B show a high level flowchart of the invention.

FIGS. 9A and 9B show a flowchart that represents a user selecting a previously evaluated discussion topic defined in FIG. 8 and generating inquiries back to the user which allows the user to reflect upon and investigate such a discussion topic and then entering a journal entry based on the inquiry generated.

FIG. 26 shows the user's View Discussion Report.

FIG. 27 shows the user's View Category Report.

FIG. 28 shows the user's Autobiography Report.

FIG. 29 shows the Linguistic Constructs Table which contains the data derived from the MOTIVATION MANAGER 3 component in FIG. 2 and the MINDSET DEVELOPER 4 component in FIG. 3 and organized into linguistic constructs in order to build inquiries that are generated back to the user.

FIGS. 30a through 30f shows a series (FIG. 30a through FIG. 30f) of figures that represent stages of designing and developing the relationship anatomy model which is used as a structure for developing the Linguistic Constructs Table in FIG. 29.

FIG. 31 shows a different view of the relationship anatomy model wherein each set of attitudinal trait descriptions are classified in each quadrant cache.

FIG. 33 shows a user interface to define a user's state of mind descriptions.

FIG. 34 shows a user interface to enter the scores from specific Birkman Method evaluation reports. Refer to Appendix A.

FIG. 36 shows a user interface wherein the user has identified a second collection of attitudinal trait descriptions from the user's first collection of "need" attitudinal trait descriptions as described in FIG. 35 above wherein the user has identified a higher awareness from the first collection through the MOTIVATION AMPLIFIER 12 component in FIG. 2. This collection is also described in FIG. 7.

FIG. 37 shows a user interface wherein the user's most extreme "stress reaction" attitudinal trait descriptions (e.g., grouped as "most like" and "least like" the user) have been classified as a first collection through the MOTIVATION EQUALIZER 11 component in FIG. 2. This collection is also described in FIG. 7.

FIG. 39 shows a user interface wherein the user's most extreme "interest" attitudinal trait descriptions (e.g., grouped as "most like" and "least like" the user) have been classified as a first collection through the MOTIVATION EQUALIZER 11 component in FIG. 2. This collection is also described in FIG. 7.

FIG. 42 shows a user interface wherein the user has identified a second collection of attitudinal trait descriptions from the user's first collection of "strength" attitudinal trait descriptions as described in FIG. 41 above wherein the user has identified a higher awareness from the first collection through the MOTIVATION AMPLIFIER 12 component in FIG. 2. This collection is also described in FIG. 7.

FIG. 44 shows a user interface wherein the user develops their autobiography for the fundamental category "confidence".

FIG. 46 shows a user interface wherein the user develops their autobiography for the fundamental category "devotion".

FIG. 47 shows a user interface wherein the user develops their autobiography for the fundamental category "honor".

DETAILED DESCRIPTION OF THE INVENTION

Figure 1:
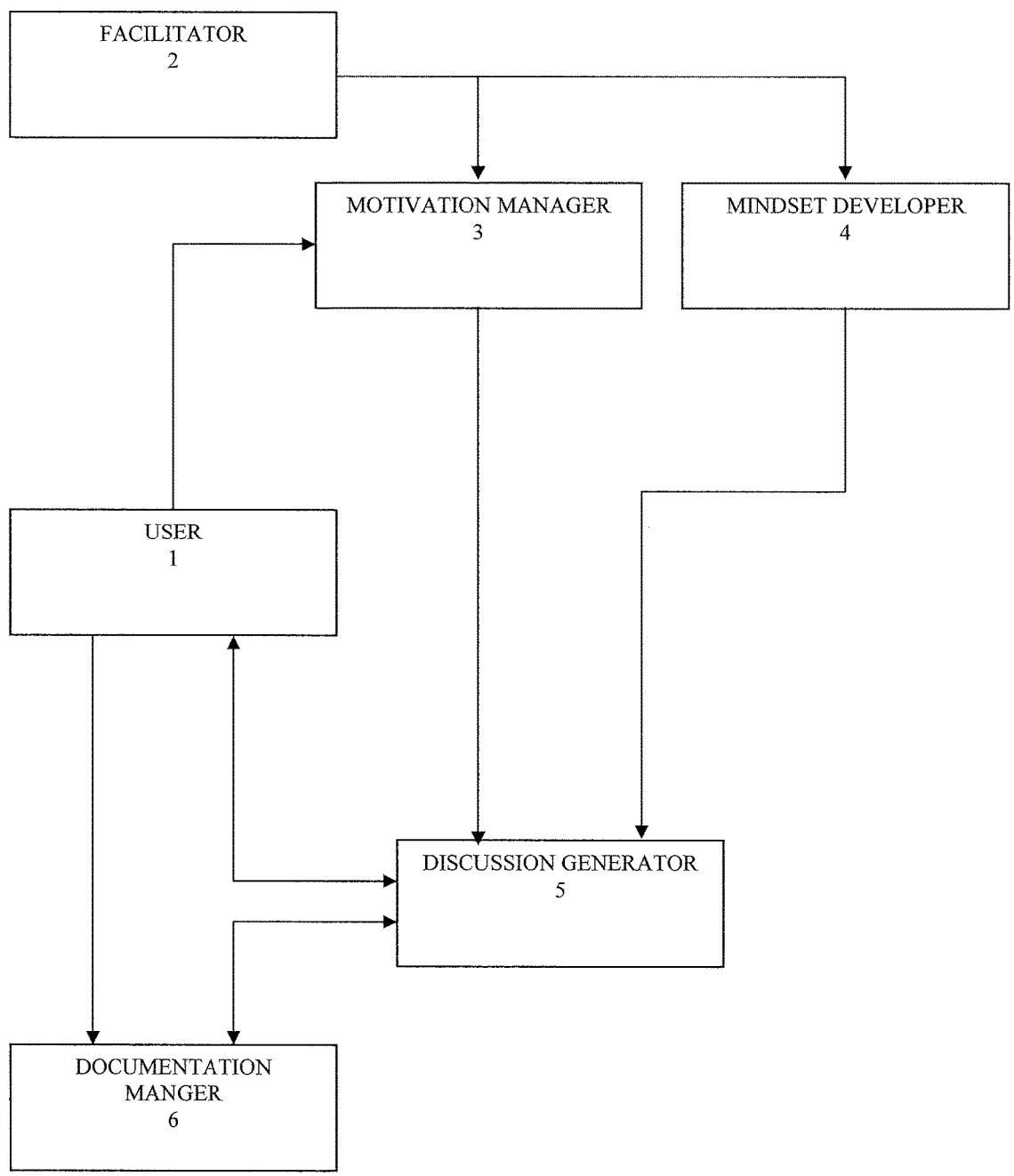
FIG. 1 shows a block diagram of the invention.

Brief Description of the Components in the Block Diagram of the Invention
(Referring to FIG. 1 Through FIG. 5)
User 1

This component represents the person using the system.
Facilitator 2

This component represents an expert skilled in the art of defining concepts for developing relationships in a series of Fundamental Categories (e.g., Confidence, Patience, Devotion, Honor) and corresponding Motivational Coping Techniques which aid in developing or evolving such Fundamental Categories according to the USER PROFILE 9 predefined Motivational Attributes (e.g., needs, stress reactions, interests, strengths).
Motivation Manager 3

This component aids the user of the system in classifying their motivations (e.g., behaviors or attitudes) into sets of Attitudinal Trait Descriptions. Here, the facilitator (e.g., the FACILITATOR 2 component) also may modify the Motivational Attributes (e.g., needs) from the USER PROFILE 9 component which the system uses as a source for developing or evolving the Fundamental Categories (e.g., "Confidence").
Mindset Developer 4

This component defines the Fundamental Categories (e.g., confidence) of the system and defines the Motivational Coping Techniques (e.g., support) which generate the development or evolution of the Fundamental Categories.
Discussion Generator 5

This component allows the user to evaluate a Discussion Topic. It also generates inquires back to the user for the user to investigate based on a specific Discussion Topic Evaluation. The Linguistic Constructs Table in this DISCUSSION GENERATOR 5 component (refer to FIG. 29) contain data which is derived from the MOTIVATION MANAGER 3 and the MINDSET DEVELOPER 4 components.
Documentation Manager 6

This component allows the user to write journal entries (e.g., personal experiences) into a data structure based on inquires generated from the DISCUSSION GENERATOR 5 component and to write entries in their personal autobiography. It also allows the user to produce reports (refer to FIG. 26, FIG. 27 and FIG. 28) in order to review their journal entries and autobiography entries.
Input/Output Interface 7

This component is the communication interface for the MOTIVATION MANAGER 3 which interacts with the USER 1 and the RELATING STRUCTURE CACHE 5 components.
State of Mind Constructor 8

With the aid of the FACILITATOR 2 component, this component defines the "passive" (e.g., suggesting less effort) and "active" (e.g., suggesting more effort) state of mind descriptions of the user. These descriptions (e.g., for a "passive" state of mind are: creativity, clarity, and satisfaction) are used as part of the inquiries which are generated back to the user from the DISCUSSION GENERATOR 5 component.

User Profile 9

This component represents the motivational instrument (e.g., behavior assessment) used in the system (e.g., the Birkman Method). This is an external instrument used subjectively by the user to evaluate their behaviors and attitudes. The results of such an instrument produce descriptions of a user's behaviors or attitudes which are "most like" and "least like" the user within one or more Motivational Attributes (e.g., needs, stress reactions, interests, and strengths).
Motivational Attribute Constructor 10

This component identifies the Motivational Attributes defined from the USER PROFILE 9. A Motivational Attribute (e.g., needs) represents the source for developing or evolving a related Fundamental Category (e.g., confidence).
Motivation Equalizer 11

This component determines a first set of Attitudinal Trait Descriptions which are "most like" and "least like" the user for every Motivational Attribute identified by the MOTIVATIONAL ATTRIBUTE CONSTRUCTOR 10.
Motivation Amplifier 12

This component determines a second sub-set of Attitudinal Trait Descriptions for each first set of Attitudinal Trait Descriptions wherein the user has identified a "higher" awareness of the first set identified from the MOTIVATION EQUALIZER 11.
Input/Output Interface 13

This component is the communication interface for the MINDSET DEVELOPER 4 which interacts with the USER 1 and the DISCUSSION GENERATOR 5 components.
Fundamental Category Constructor 14

With the aid of the FACILITATOR 2 component, this component defines each of the Fundamental Categories (e.g., confidence) as each relate to its corresponding Motivational Attribute (e.g., needs) identified by the MOTIVATIONAL ATTRIBUTE CONSTRUCTOR 10 which is also supported by the FACILITATOR 2 component.
Motivational Coping Technique Constructor 15

This component defines ways in which one would cope in developing or evolving each Fundamental Category (e.g., confidence) for its corresponding Motivational Attribute in relation to each set of Attitudinal Trait Descriptions. Two or more Motivational Coping Techniques are defined for each Fundamental Category. In one embodiment of this application, four Motivational Coping Techniques are defined for each Fundamental Category (e.g., confidence). Of the four, two are defined as "Passive" (e.g., suggesting less effort) Motivational Coping Techniques (e.g., allow & accept are the first and second "passive" motivational coping techniques) and two are defined as "Active" (e.g., suggesting more effort) Motivational Coping Techniques (e.g., maintain & support are the first and second "active" motivational coping techniques). In addition, the Motivational Coping Techniques are designed to support specific Quadrant Caches in the Linguistic Constructs Table in FIG. 29 for any Discussion Topic Evaluation and the user's Autobiography.
Input/Output Interface 16

This component is the communication interface for the DISCUSSION GENERATOR 5 component which interacts with the MOTIVATION MANAGER 3, the MINDSET DEVELOPER 4, the USER 1 and the DOCUMENTATION MANAGER 6 components.
Linguistics Organizer 17

This component builds a table called the Linguistic Constructs Table in FIG. 29. This table consists of the constructs necessary to develop the inquiries that are generated back to the user along with the appropriate set of Attitudinal Trait Descriptions. The data for this table is derived from the MOTIVATION CONSTRUCTOR 2 and the MINDSET DEVELOPER 4 components.

Inquiry Builder 18

This component builds an inquiry that is generated back to the user which is based on the criteria identified by the RESPONSE MANAGER 20 component.

Discussion Topic Evaluation 19

This component aids the user in defining a Discussion Topic (e.g., relationship with Karen) wherein true/untrue statements are presented to the user for the user to evaluate the Discussion Topic for each Fundamental Category (e.g., "Confidence") based on a rank of 1 to 10, a confidence level indicator which indicates the users confidence in their rank, and the Response Type desired for each inquiry generated back to the user. A Response Algorithm calculates the user's perceived value of the Discussion Topic and a record is stored in a data structure which represents the evaluation of such a Discussion Topic.

Response Manager 20

This component analyzes the results of the DISCUSSION TOPIC EVALUATION 19 for a specific Discussion Topic and determines the criteria necessary to construct the inquiry for each Fundamental Category (e.g., "Confidence").

Presentation Constructor 21

This component presents an inquiry generated back to the user for each Fundamental Category (e.g., "Confidence) for a specific Discussion Topic so that the user may reflect upon it in order to determine an appropriate response wherein the user will enter a journal entry in the JOURNAL DEVELOPER 23 component.

Input/Output Interface 22

This component is the communication interface for the DOCUMENTATION MANAGER 6 which interacts with the USER 1 and the DISCUSSION GENERATOR 5 components.

Journal Developer 23

This component is a data structure for the user to write and store entries for each inquiry presented to them generated from the DISCUSSION GENERATOR 5 component.

Report Manager 24

This component allows the user to view and print reports wherein the user may review their journal entries entered in the JOURNAL DEVELOPER 23 component.

Autobiography Developer 25

This component generates autobiography statements (not to be confused with the true/untrue statements presented to the user in the DISCUSSION TOPIC EVALUATION 19 component) for each set of Attitudinal Trait Descriptions derived from the MOTIVATION MANAGER 3 component and provides a data structure for the user to write and store entries which answer each autobiography statement. Each statement which relates to every set of attitudinal trait descriptions includes both the "Passive" and "Active" motivational coping techniques and related linguistic constructs from the Linguistic Constructs Table in FIG. 29 in the LINGUISTICS ORGANIZER 17 component in FIG. 4.

DETAILED DESCRIPTION OF THE METHOD OF THE INVENTION

The following steps are performed:

[1] Obtain the user's responses from the user profile (e.g., the Birkman Method) which are indicative of the user's attitudes or behaviors (denoted as "attitudinal trait descriptions" herein). Refer to the USER PROFILE 9 component in FIG. 2, FIGS. 7A and 7B, and Appendix A.

[2] Obtain the motivational attributes (e.g., needs, stress reactions, interests, and strengths) from the user profile for classifying the user's attitudinal trait descriptions. Refer to the MOTIVATIONAL ATTRIBUTE CONSTRUCTOR 10 component in FIG. 2 and FIGS. 7A and 7B, wherein the user's attitudinal traits are classified as: (a) those attitudinal traits most like the user, (b) those attitudinal traits least like the user, (c) those attitudinal traits for which the user has a greater awareness, (d) those attitudinal traits for which the user has a lesser awareness. Additionally, (FIG. 7B) obtain a description from the user which the user associates with a passive state of mind, and obtain a description from the user which the user associates with an active state of mind.

[3] The facilitator confirms that the motivational attributes obtained from the user profile in step 5 above are nouns and confirms that each motivational attribute is appropriately expressed for the purpose of developing the Linguistic Constructs Table in FIG. 29. Refer to the MOTIVATIONAL ATTRIBUTE CONSTRUCTOR 10 component in FIG. 2 and FIGS. 7A and 7B.

[4] Construct the Linguistic Constructs Table in FIG. 29 according to the motivational attributes obtained in step 2 above and confirmed by the facilitator in step 3 above and according to the design of the Relationship Anatomy Model in FIG. 30a through 30f. Refer to the Linguistic Constructs Table Detailed Description section in this application.

Figure 2:
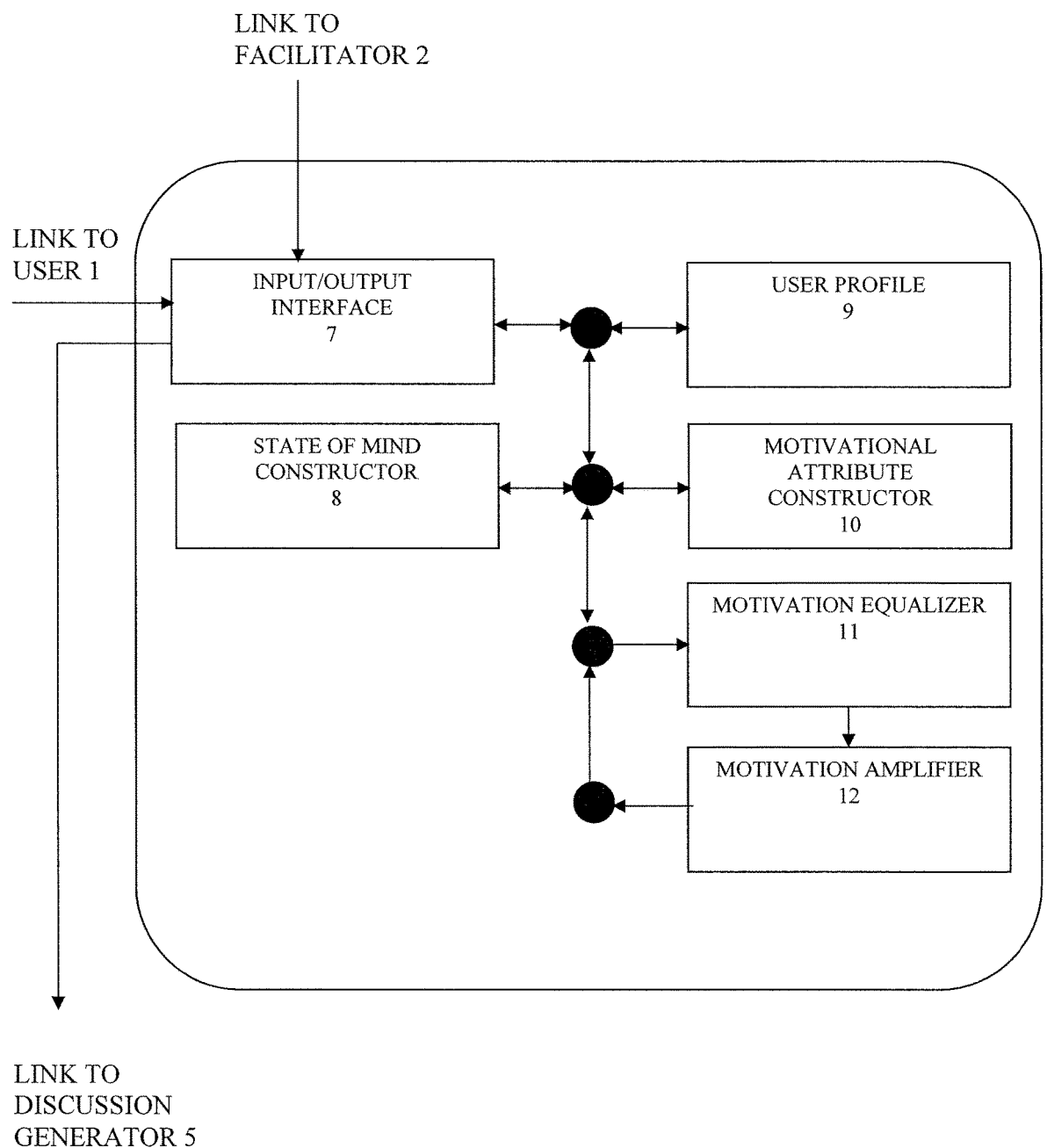
FIG. 2 shows a block diagram of the component called MOTIVATION MANAGER 3. This component classifies the user's attitudinal trait descriptions (e.g., behaviors or attitudes), determines the motivational attributes (e.g., needs) from the user profile (which the facilitator and user may modify), and defines the "passive" (e.g., suggesting less effort) and "active" (e.g., suggesting more effort) descriptions.
Figure 3:
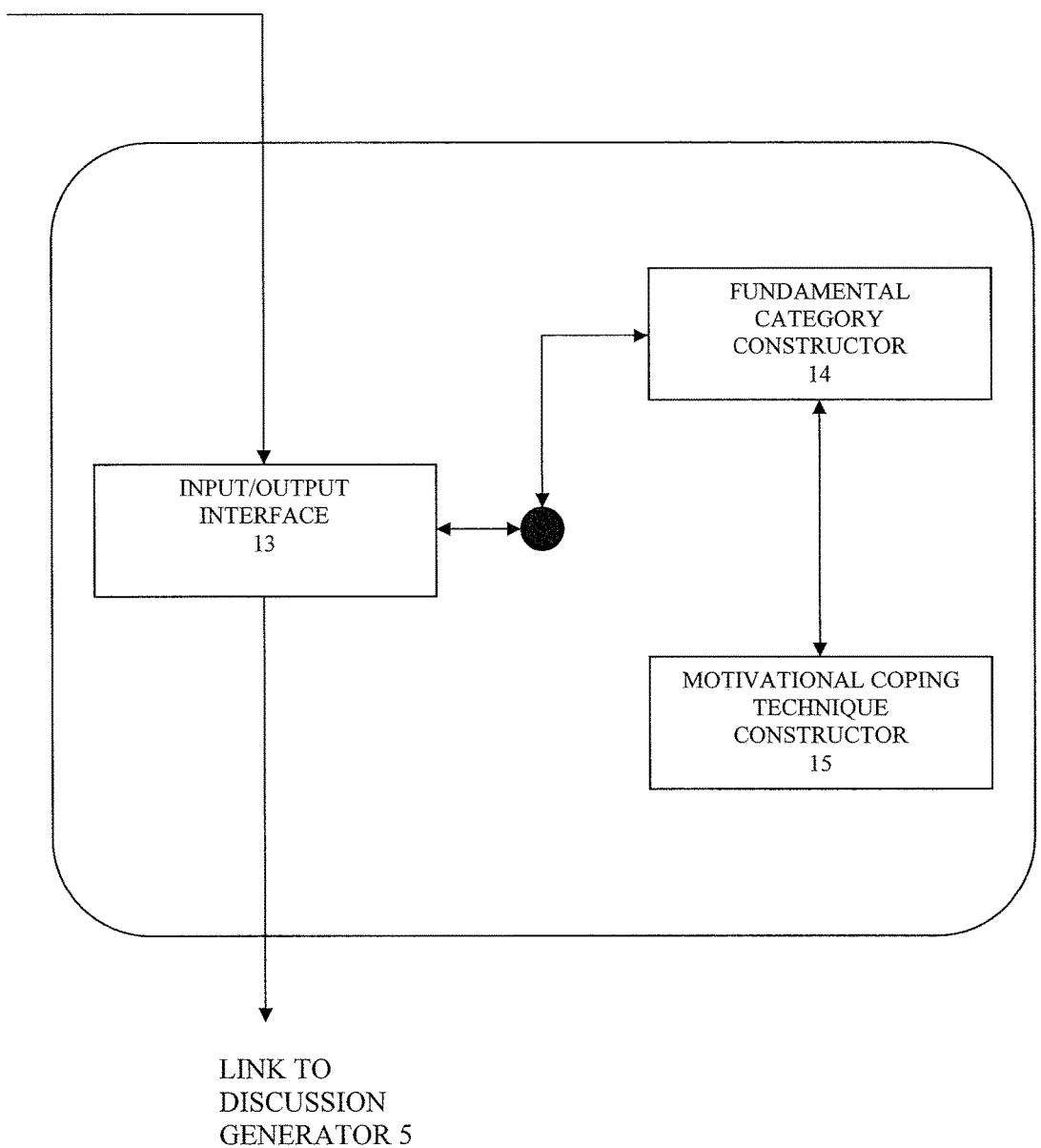
FIG. 3 shows a block diagram of the component called MINDSET DEVELOPER 4. This component utilizes the facilitator to classify the fundamental categories (e.g., confidence) and the fundamental categories corresponding motivational coping techniques (e.g., support).
Figure 7A:
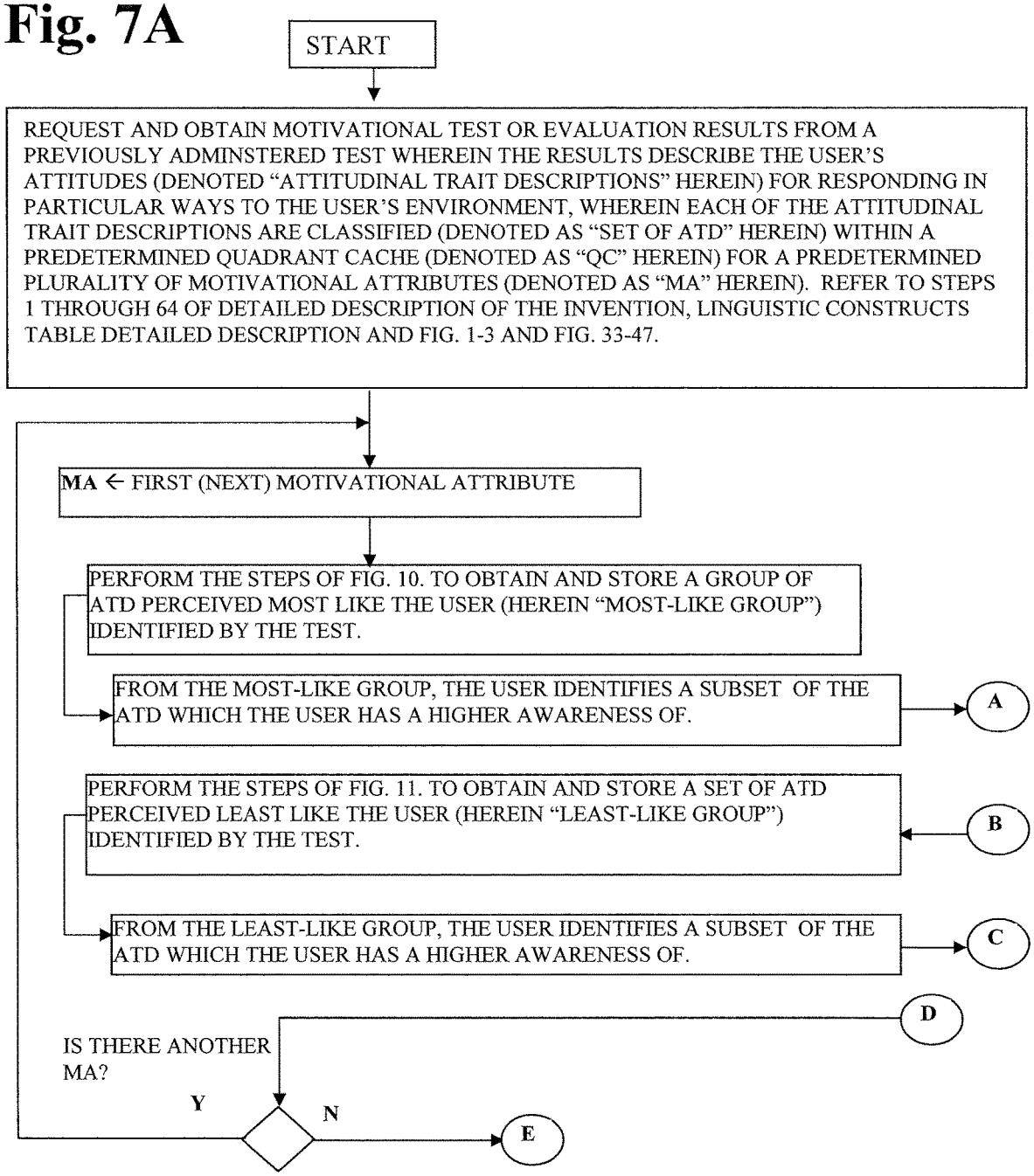
FIGS. 7A through 7E show a flowchart that represents the classification of user's attitudinal trait descriptions extracted from the USER PROFILE 9 in FIG. 2 for each motivational attribute (defined from the user profile) and the process in which autobiography statements (e.g., questions) are generated for the user's autobiography. In addition, this flowchart represents defining descriptions of a user's "passive" and "active" state of mind and shows how the facilitator helps to define the fundamental categories and related motivational coping techniques.
Figure 7B:
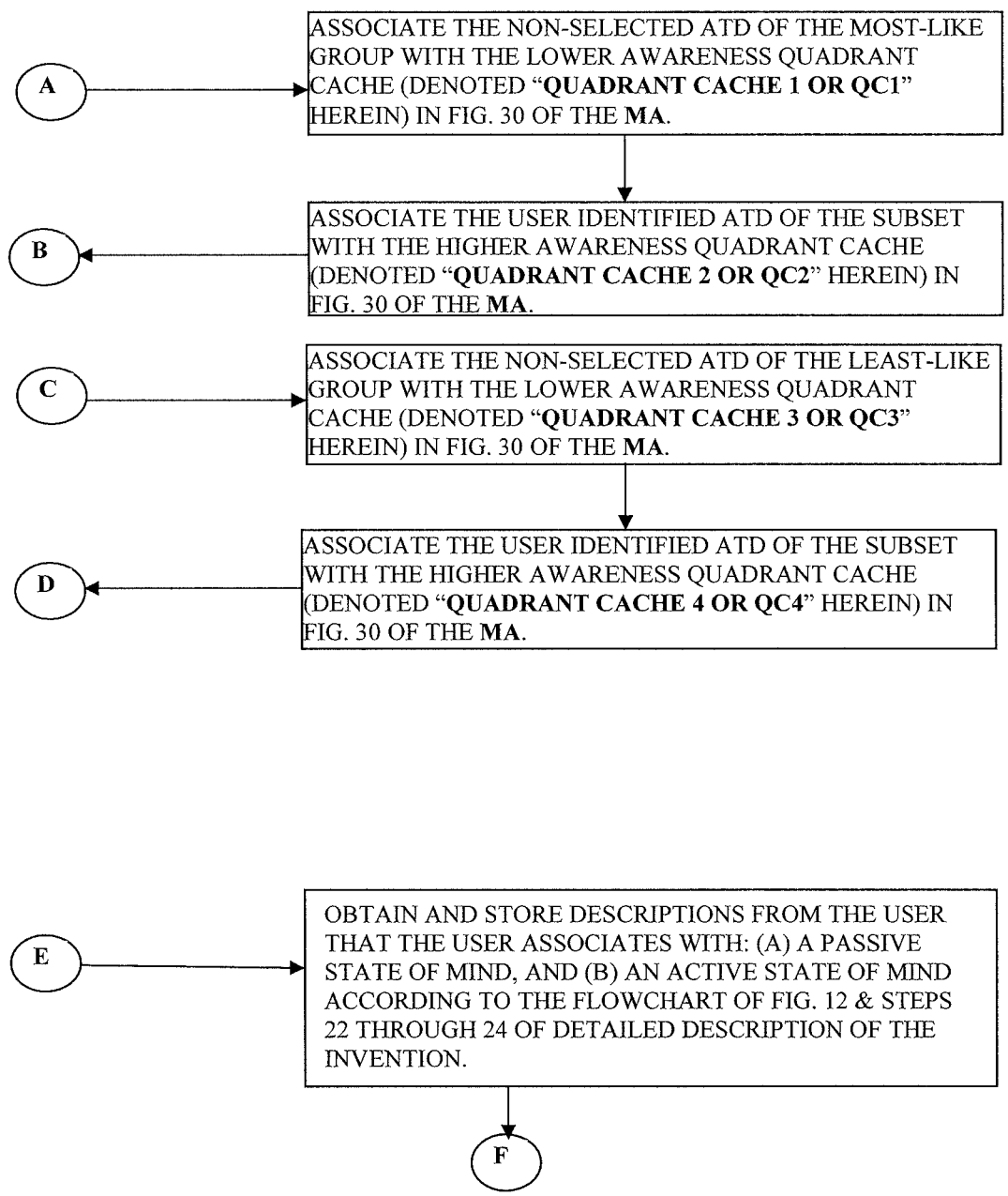
Figure 7C:
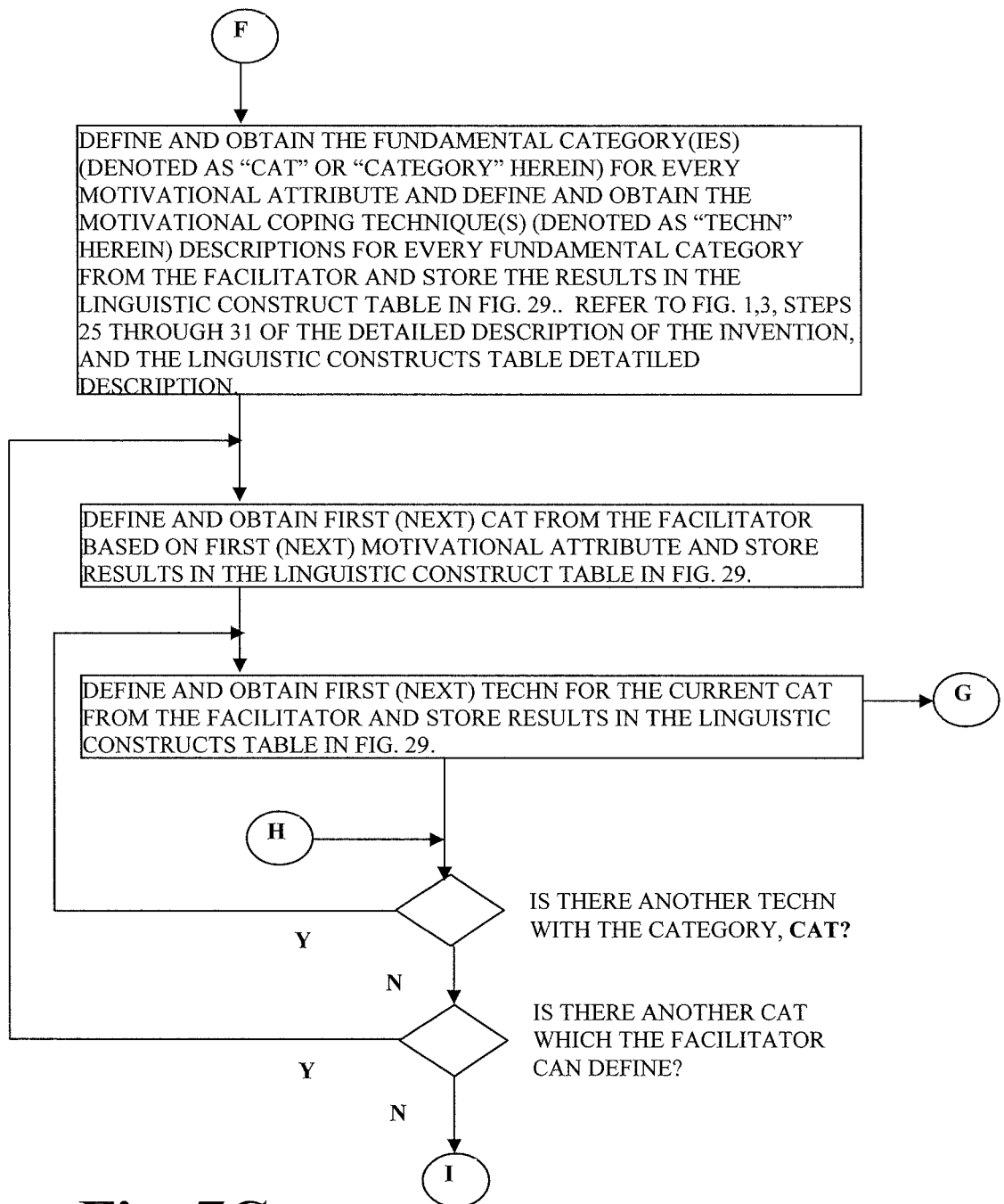
Figure 7D:
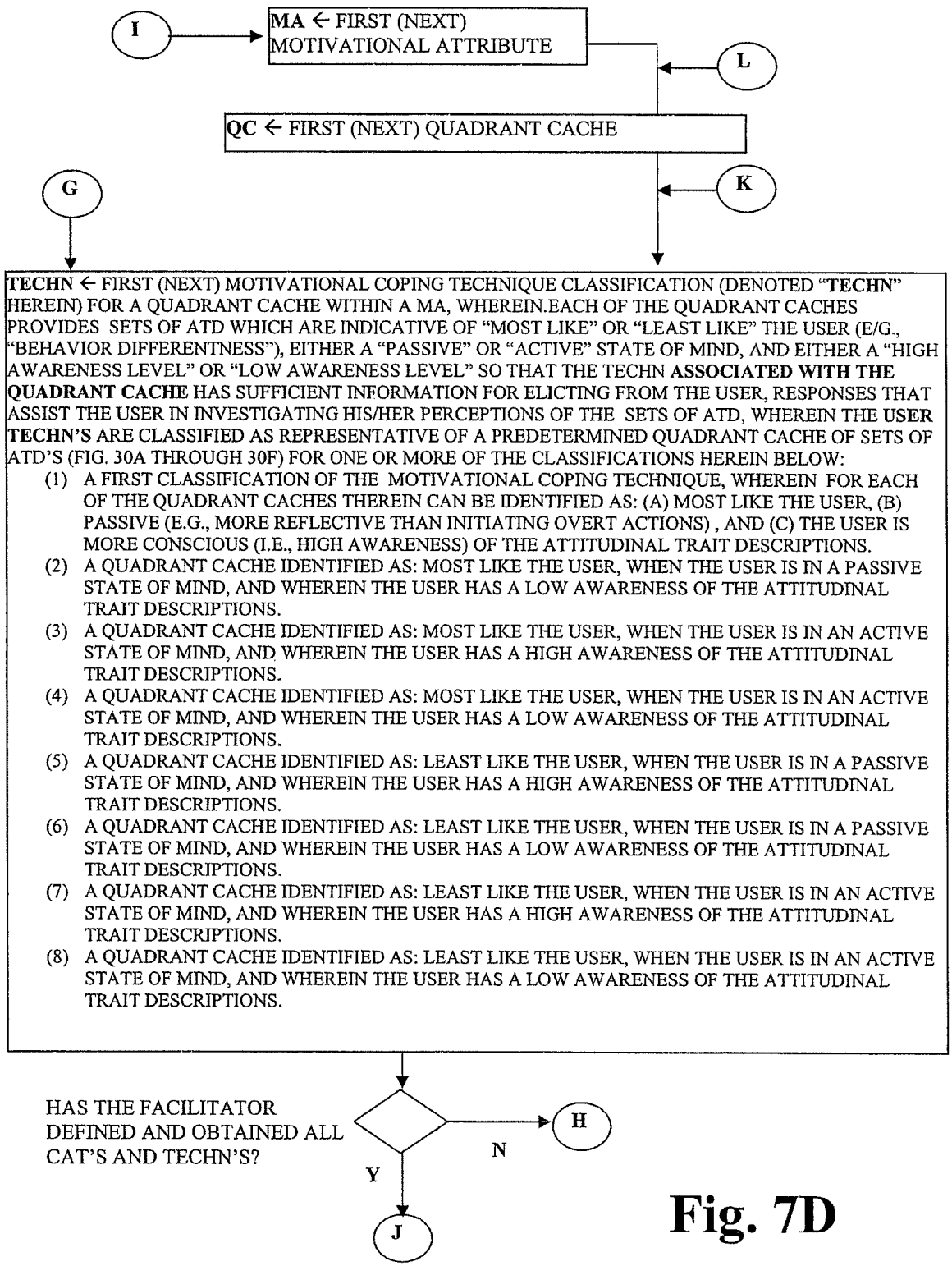
Figure 7E:
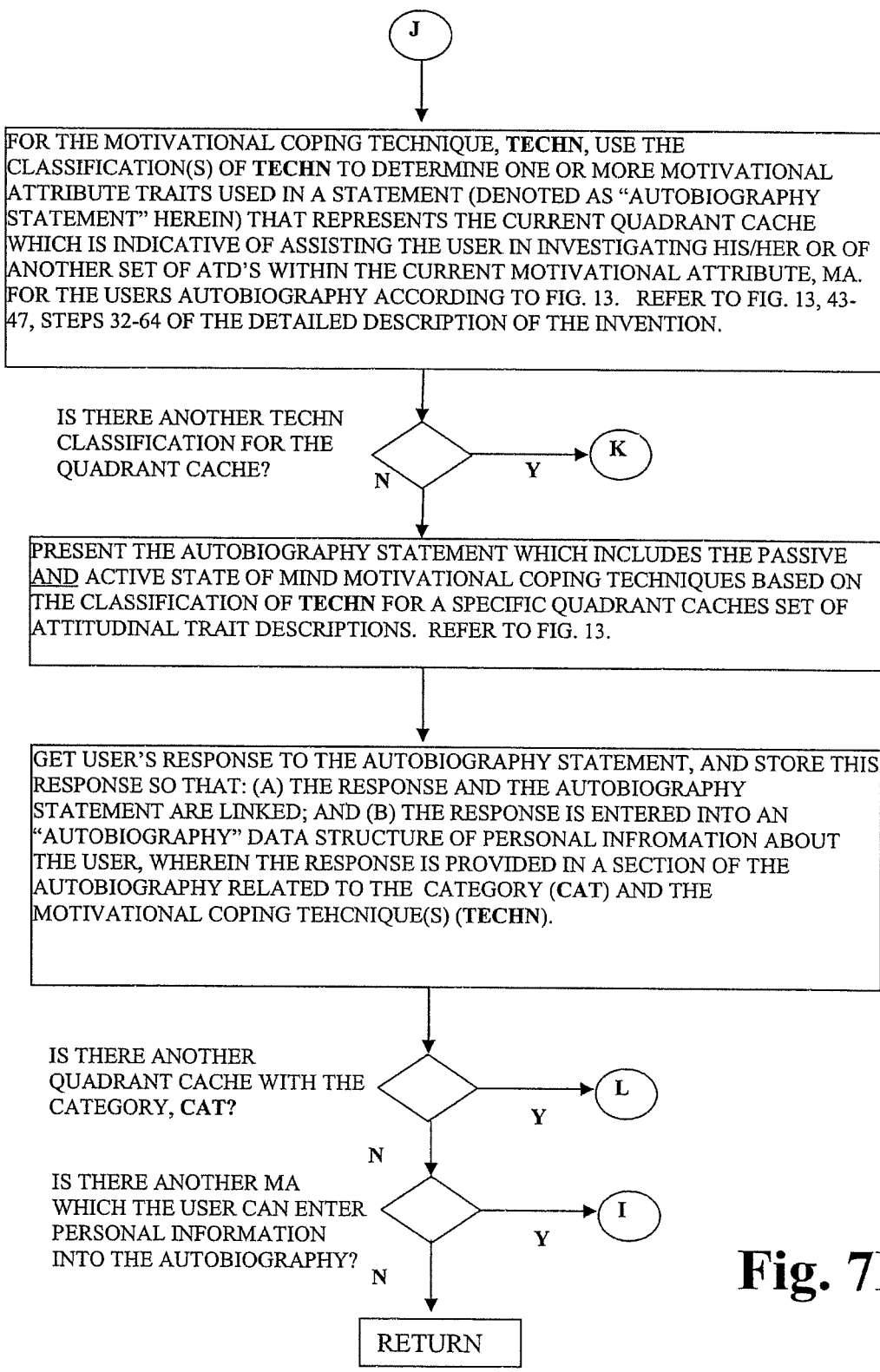

[5] Users scores from the user profile are entered via the INPUT/OUTPUT INTERFACE 7 in FIG. 2 so that specific attitudinal trait descriptions (i.e., attitudes or behaviors) can be determined from the user profile, wherein there is a collection of such specific attitudinal trait descriptions for each motivational attribute as described in step 2 above. Refer to FIGS. 7A and 7B, and 34.

Figure 10:
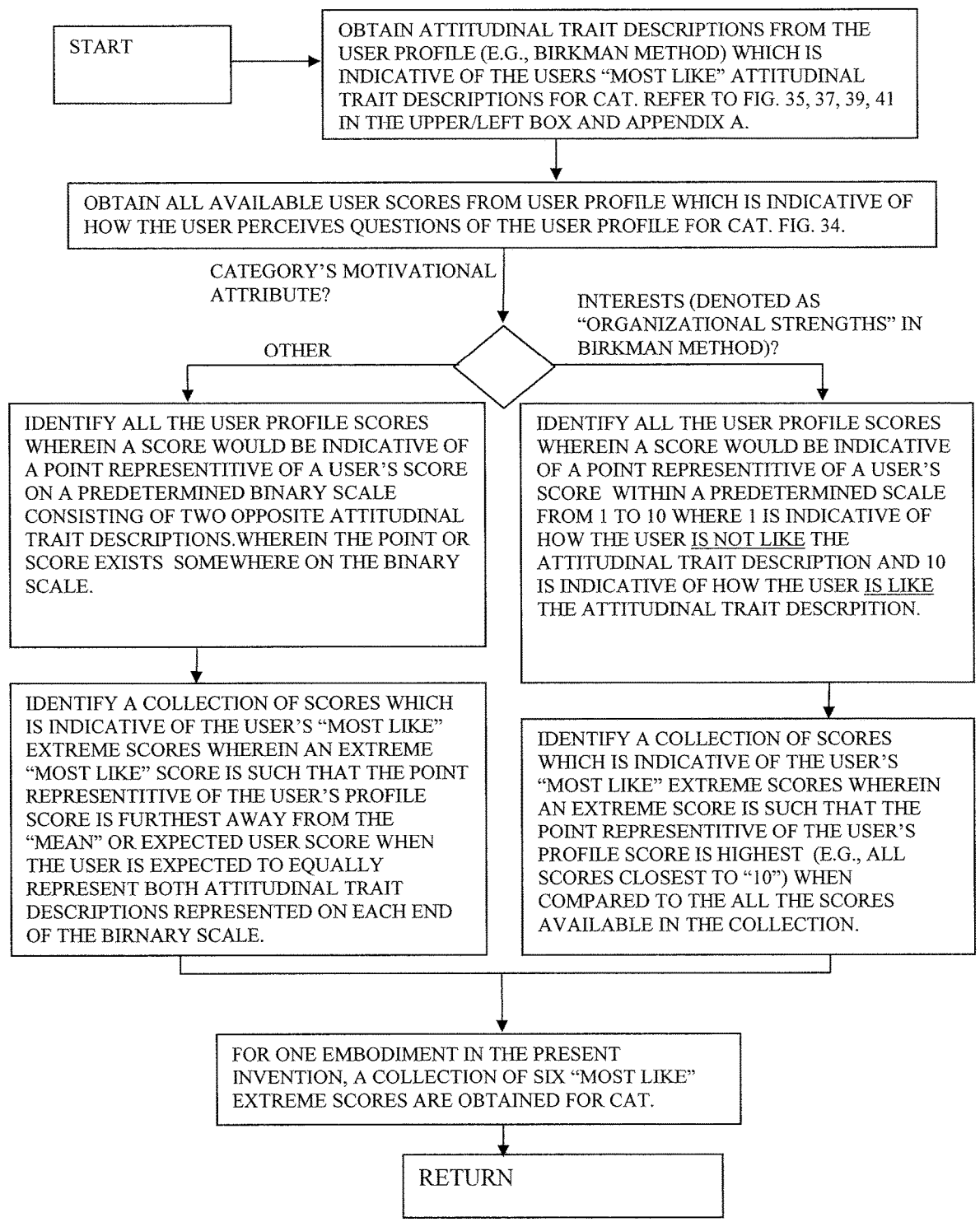
FIG. 10 shows a flowchart that represents a process wherein the user's "most like" attitudinal trait descriptions are classified for each motivational attribute defined from the user profile in FIG. 2 or 7.
Figure 35:
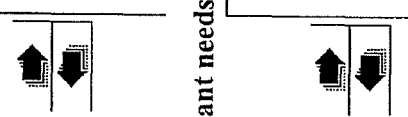
FIG. 35 shows a user interface wherein the user's most extreme "need" attitudinal trait descriptions (e.g., grouped as "most like" and "least like" the user) have been classified as a first collection through the MOTIVATION EQUALIZER 11 component in FIG. 2. This collection is also described in FIG. 7.

[6] A first collection of attitudinal trait descriptions is extracted from the user profile, wherein the first collection consists of six of the user's most like descriptions classified in, e.g., the "need" (motivational attribute) category. Refer to the MOTIVATION EQUALIZER 11 component in FIG. 2, to the upper box (e.g., which represents quadrant cache 1 in FIGS. 30 and 31) in FIG. 35 and refer to FIGS. 7A and 7B, and 10, and Appendix A.

Figure 11:
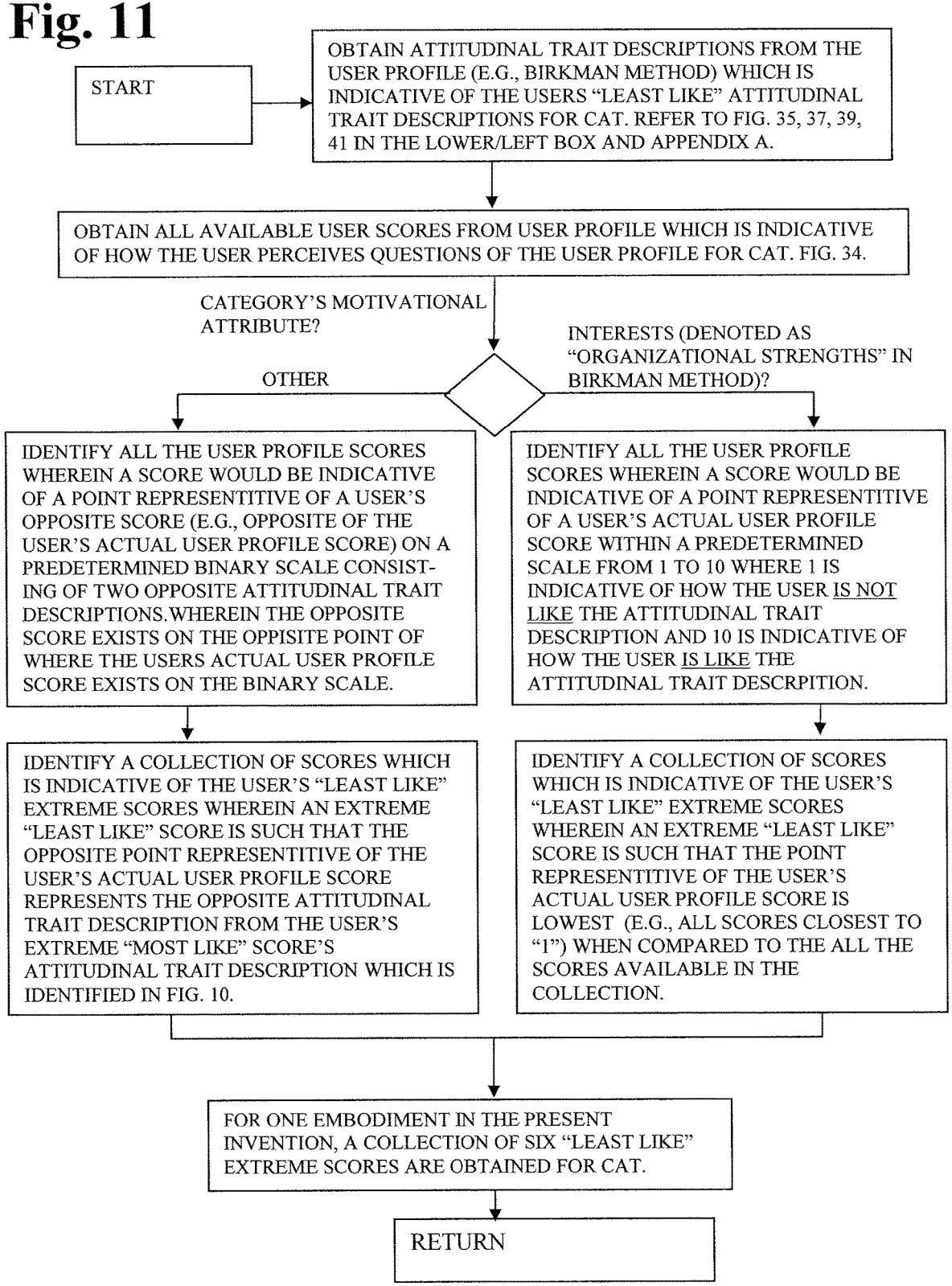
FIG. 11 shows a flowchart that represents a process wherein the user's "least like" attitudinal trait descriptions are classified for each motivational attribute defined from the user profile in FIG. 2 or 7.
Figure 12:
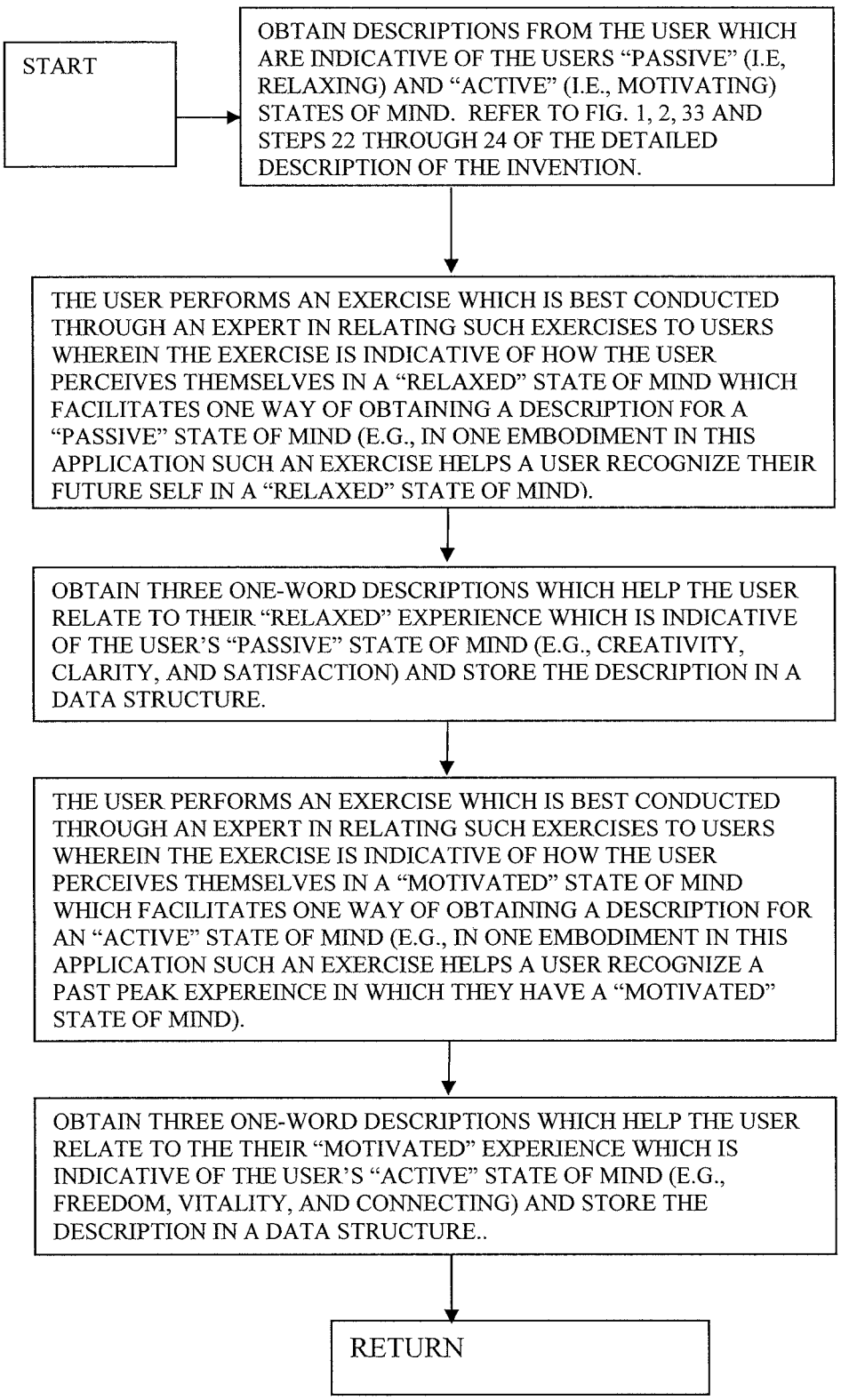
FIG. 12 shows a flowchart that represents a process for defining descriptions of a user's "passive" and "active" state of mind.
Figure 13:
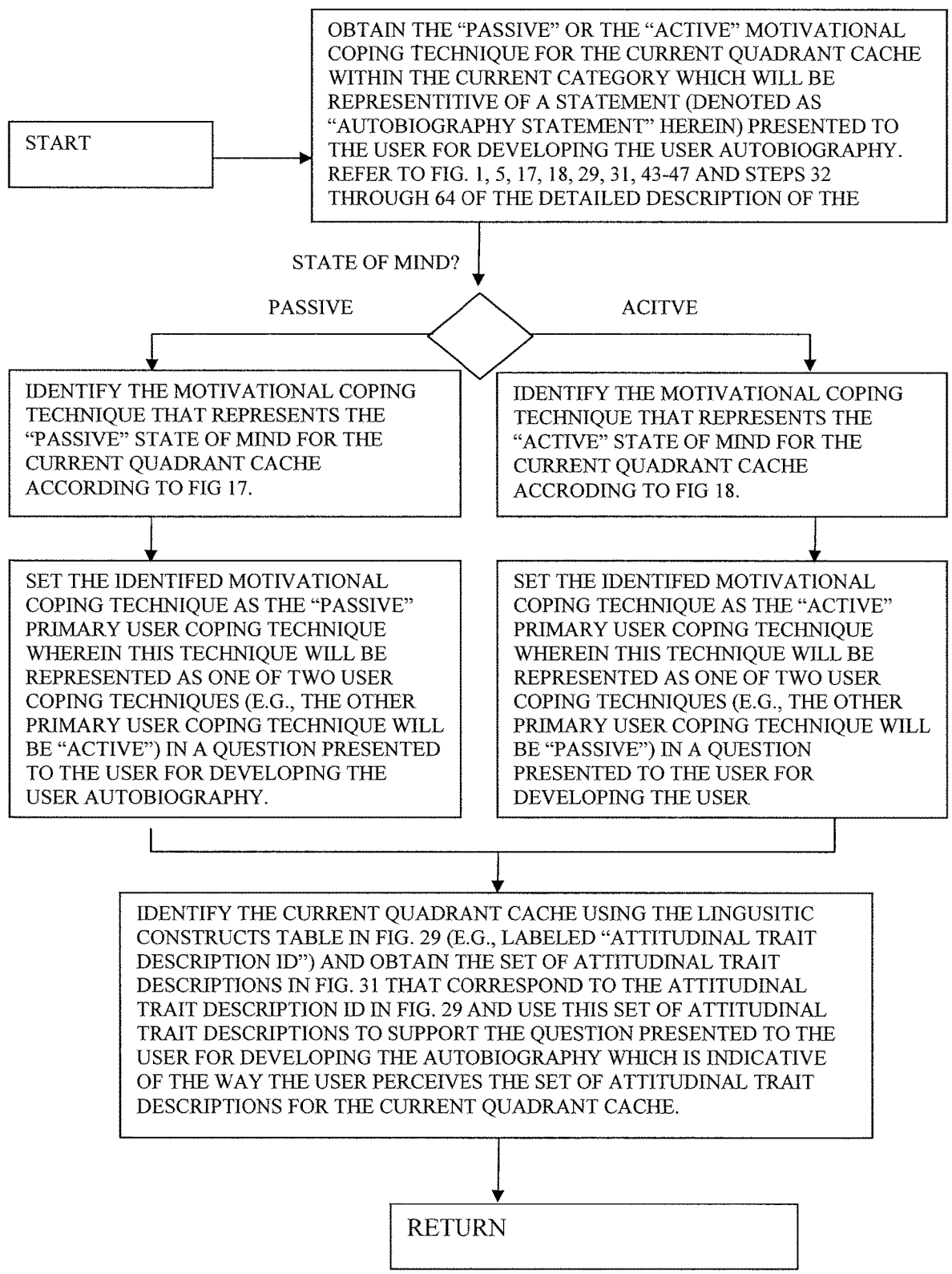
FIG. 13 shows a flowchart that represents a process for developing an autobiography statement which identifies the motivational coping techniques for such an autobiography statement for each quadrant cache for every fundamental category (e.g., confidence) in order to develop the user's autobiography.

[7] A second collection of attitudinal trait descriptions is extracted from the user profile, wherein the second collection consists of six of the user's least like descriptions classified in, e.g., the "need" (motivational attribute) category. Refer to the MOTIVATION EQUALIZER 11 component in FIG. 2, to the lower box (e.g., which represents quadrant cache 3 in FIGS. 30 and 31) in FIG. 35 and refer to FIGS. 7A and 7B, and 11, and Appendix A.

[8] A first collection of attitudinal trait descriptions is extracted from the user profile, wherein the first collection consists of six of the user's most like descriptions classified in, e.g., the "stress reaction" (motivational attribute) category. Refer to the MOTIVATION EQUALIZER 11 component in FIG. 2, to the upper box (e.g., which represents quadrant cache 1 in FIGS. 30 and 31) in FIG. 37 and refer to FIGS. 7A and 7B, and 10, and Appendix A.

[9] A second collection of attitudinal trait descriptions is extracted from the user profile, wherein the second collection consists of six of the user's least like descriptions classified in, e.g., the "stress reaction" (motivational attribute) category. Refer to the MOTIVATION EQUALIZER 11 component in FIG. 2, to the lower box (e.g., which represents quadrant cache 3 in FIGS. 30 and 31) in FIG. 37 and refer to FIGS. 7A and 7B, and 11, and Appendix A.

[10] A first collection of attitudinal trait descriptions is extracted from the user profile, wherein the first collection consists of six of the user's most like descriptions classified in, e.g., the "interest" (motivational attribute) category. Refer to the MOTIVATION EQUALIZER 11 component in FIG. 2, to the upper box (e.g., which represents quadrant cache 1 in FIGS. 30 and 31) in FIG. 39 and refer to FIGS. 7A and 7B, 10, and Appendix A.

[11] A second collection of attitudinal trait descriptions is extracted from the user profile, wherein the second collection consists of six of the user's least like descriptions classified in, e.g., the "interest" (motivational attribute) category. Refer to the MOTIVATION EQUALIZER 11 component in FIG. 2, to the lower box (e.g., which represents quadrant cache 3 in FIGS. 30 and 31) in FIG. 39 and refer to FIGS. 7A and 7B, and 11, and Appendix A.

Figure 41:
FIG. 41 shows a user interface wherein the user's most extreme "strength" attitudinal trait descriptions (e.g., grouped as "most like" and "least like" the user) have been classified as a first collection through the MOTIVATION EQUALIZER 11 component in FIG. 2. This collection is also described in FIG. 7.
Figure 43:
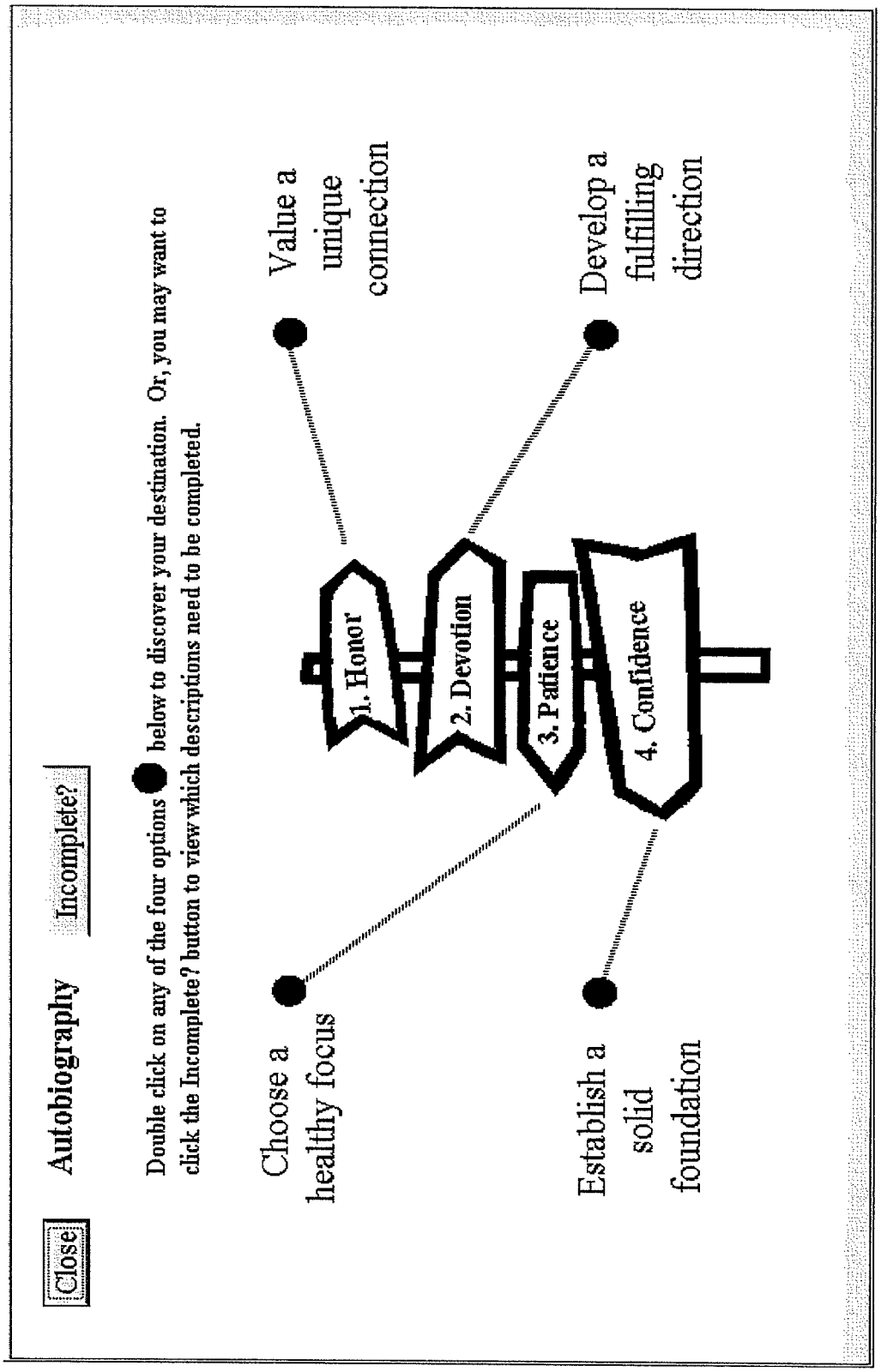
FIG. 43 shows a user interface wherein a site map is provided to direct the user in developing their autobiography.

[12] A first collection of attitudinal trait descriptions is extracted from the user profile, wherein the first collection consists of six of the user's most like descriptions classified in, e.g., the "strength" (motivational attribute) category. Refer to the MOTIVATION EQUALIZER 11 component in FIG. 2, to the upper box (e.g., which represents quadrant cache 1 in FIGS. 30 and 31) in FIG. 41 and refer to FIGS. 7A and 7B, and 10, and Appendix A.

[13] A second collection of attitudinal trait descriptions is extracted from the user profile, wherein the second collection consists of six of the user's least like descriptions classified in, e.g., the "strength" (motivational attribute) category. Refer to the MOTIVATION EQUALIZER 11 component in FIG. 2, to the lower box (e.g., which represents quadrant cache 3 in FIGS. 30 and 31) in FIG. 41 and refer to FIGS. 7A and 7B, and 11, and Appendix A.

[14] A subset of the first collection (denoted in FIG. 31 labeled as "A.1.2" herein) of attitudinal trait descriptions is selected from the attitudinal trait descriptions obtained in step 6 above, wherein those selected here consist of three "most like" the user need (e.g., motivational attribute) descriptions that the user has a higher awareness and the three attitudinal trait descriptions which are not selected are denoted in FIG. 31 labeled as "A.1.1." herein. To perform this step, as shown in FIG. 36, a question is presented to the user wherein the user selects three of the motivations (e.g., attitudinal trait descriptions) and moves them one at a time from the left-hand box to the adjacent right-hand box (e.g., which represents quadrant cache 2 in FIGS. 30 and 31). The question is "Which three motivations are your most important needs?" Refer to the MOTIVATION AMPLIFIER 12 component in FIG. 2 and FIGS. 7A and 7B.

A subset of the second collection (denoted in FIG. 31 labeled as "A.2.4" herein) of attitudinal trait descriptions is selected from the attitudinal trait descriptions obtained in step 7 above, wherein those selected here consist of three "least like" the user need (e.g., motivational attribute) descriptions that the user has a higher awareness and the three attitudinal trait descriptions which are not selected are denoted in FIG. 31 labeled as "A.2.3" herein. To perform this step, as shown in FIG. 36, a question is presented to the user wherein the user selects three of the motivations (e.g., attitudinal trait descriptions) and moves them one at a time from the left-hand box to the adjacent right-hand box (e.g., which represents quadrant cache 4 in FIGS. 30 and 31). The question is "Which three motivations are others potentially important needs?" Refer to the MOTIVATION AMPLIFIER 12 component in FIG. 2 and FIGS. 7A and 7B.

Figure 38:
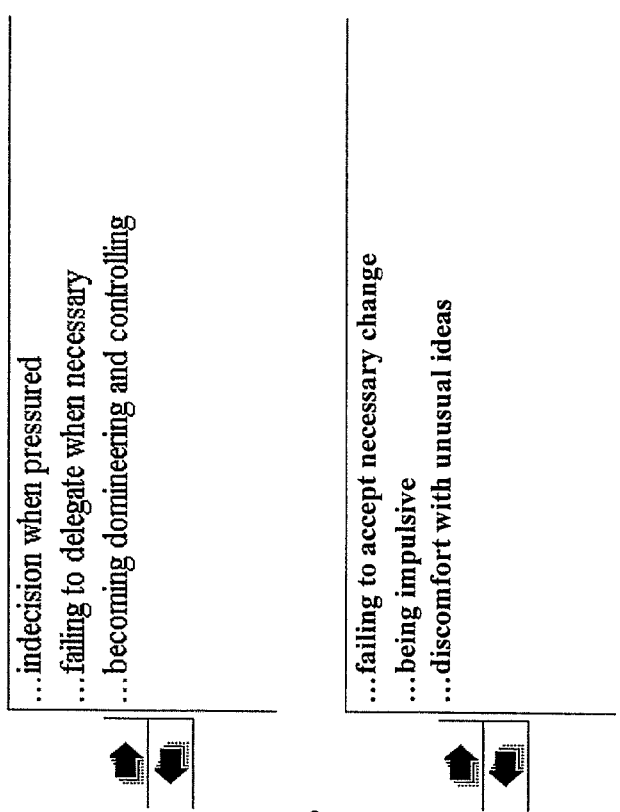
FIG. 38 shows a user interface wherein the user has identified a second collection of attitudinal trait descriptions from the user's first collection of "stress reaction" attitudinal trait descriptions as described in FIG. 37 above wherein the user has identified a higher awareness from the first collection through the MOTIVATION AMPLIFIER 12 component in FIG. 2. This collection is also described in FIG. 7.

A subset of the first collection (denoted in FIG. 31 labeled as "B.1.2" herein) of attitudinal trait descriptions is selected from the attitudinal trait descriptions obtained in step 8 above, wherein those selected here consist of three "most like" the user stress reaction (e.g., motivational attribute) descriptions that the user has a higher awareness and the three attitudinal trait descriptions which are not selected are denoted in FIG. 31 labeled as "B.1.1." herein. To perform this step, as shown in FIG. 38, a question is presented to the user wherein the user selects three of the motivations (e.g., attitudinal trait descriptions) and moves them one at a time from the left-hand box to the adjacent right-hand box (e.g., which represents quadrant cache 2 in FIGS. 30 and 31). The question is "Which three motivations are your most difficult stress reactions?" Refer to the MOTIVATION AMPLIFIER 12 component in FIG. 2 and FIGS. 7A and 7B.

[15] A subset of the second collection (denoted in FIG. 31 labeled as "B.2.4" herein) of attitudinal trait descriptions is selected from the attitudinal trait descriptions obtained in step 9 above, wherein those selected here consist of three "least like" the user stress reaction (e.g., motivational attribute) descriptions that the user has a higher awareness and the three attitudinal trait descriptions which are not selected are denoted in FIG. 31 labeled as "B.2.3." herein. To perform this step, as shown in FIG. 38, a question is presented to the user wherein the user selects three of the motivations (e.g., attitudinal trait descriptions) and moves them one at a time from the left-hand box to the adjacent right-hand box (e.g., which represents quadrant cache 4 in FIGS. 30 and 31). The question is "Which three motivations are others potentially difficult stress reactions?" Refer to the MOTIVATION AMPLIFIER 12 component in FIG. 2 and FIGS. 7A and 7B.

Figure 40:
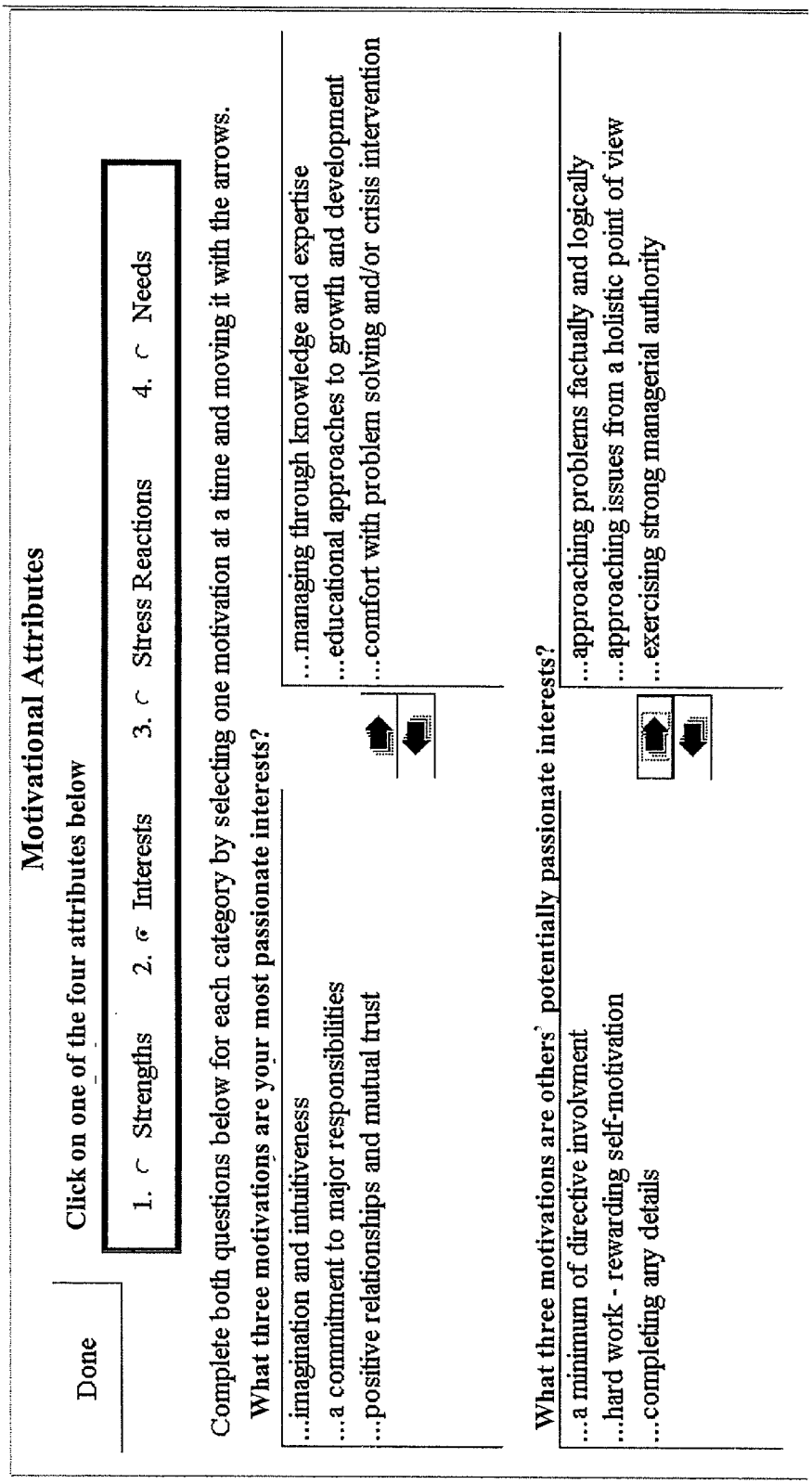
FIG. 40 shows a user interface wherein the user has identified a second collection of attitudinal trait descriptions from the user's first collection of "interest" attitudinal trait descriptions as described in FIG. 39 above wherein the user has identified a higher awareness from the first collection through the MOTIVATION AMPLIFIER 12 component in FIG. 2. This collection is also described in FIG. 7.

[16] A subset of the first collection (denoted in FIG. 31 labeled as "C.1.2" herein) of attitudinal trait descriptions is selected from the attitudinal trait descriptions obtained in step 10 above, wherein those selected here consist of three "most like" the user interest (e.g., motivational attribute) descriptions that the user has a higher awareness and the three attitudinal trait descriptions which are not selected are denoted in FIG. 31 labeled as "C.1.1." herein To perform this step, as shown in FIG. 40, a question is presented to the user wherein the user selects three of the motivations (e.g., attitudinal trait descriptions) and moves them one at a time from the left-hand box to the adjacent right-hand box (e.g., which represents quadrant cache 2 in FIGS. 30 and 31). The question is "Which three motivations are your most passionate interests?" Refer to the MOTIVATION AMPLIFIER 12 component in FIG. 2 and FIG. 7.

[17] A subset of the second collection (denoted in FIG. 31 labeled as "C.2.4" herein) of attitudinal trait descriptions is selected from the attitudinal trait descriptions obtained in step 11 above, wherein those selected here consist of three "least like" the user interest (e.g., motivational attribute) descriptions that the user has a higher awareness and the three attitudinal trait descriptions which are not selected are denoted in FIG. 31 labeled as "C.2.3." herein To perform this step, as shown in FIG. 40, a question is presented to the user wherein the user selects three of the motivations (e.g., attitudinal trait descriptions) and moves them one at a time from the left-hand box to the adjacent right-hand box (e.g., which represents quadrant cache 4 in FIGS. 30 and 31). The question is "Which three motivations are others potentially passionate interests?" Refer to the MOTIVATION AMPLIFIER 12 component in FIG. 2 and FIG. 7.

[18] A subset of the first collection (denoted in FIG. 31 labeled as "D.1.2" herein) of attitudinal trait descriptions is selected from the attitudinal trait descriptions obtained in step 12 above, wherein those selected here consist of three "most like" the user strength (e.g., motivational attribute) descriptions that the user has a higher awareness and the three attitudinal trait descriptions which are not selected are denoted in FIG. 31 labeled as "D.1.1." herein. To perform this step, as shown in FIG. 42, a question is presented to the user wherein the user selects three of the motivations (e.g., attitudinal trait descriptions) and moves them one at a time from the left-hand box to the adjacent right-hand box (e.g., which represents quadrant cache 2 in FIGS. 30 and 31). The question is "Which three motivations are your most consistent strengths?" Refer to the MOTIVATION AMPLIFIER 12 component in FIG. 2 and FIG. 7.

[19] A subset of the second collection (denoted in FIG. 31 labeled as "D.2.4" herein) of attitudinal trait descriptions is selected the attitudinal trait descriptions obtained in from step 13 above, wherein those selected here consist of three "least like" the user strength (e.g., motivational attribute) descriptions that the user has a higher awareness and the three attitudinal trait descriptions which are not selected are denoted in FIG. 31 labeled as "D.2.3." herein To perform this step, as shown in FIG. 42, a question is presented to the user wherein the user selects three of the motivations (e.g., attitudinal trait descriptions) and moves them one at a time to the adjacent right-hand box (e.g., which represents quadrant cache 4 in FIGS. 30 and 31). The question is "Which three motivations are others potentially consistent strengths?" Refer to the MOTIVATION AMPLIFIER 12 component in FIG. 2 and FIG. 7.

[20] Obtain descriptions of the user's "passive" (described in step 23 below) and "active" (described in step 24 below) states of mind which are descriptions that are indicative of the user being in a "relaxed" state of mind for a "passive" state of mind description and "motivated" state of mind for an "active" state of mind description. Refer to the STATE OF MIND CONSTRUCTOR 8 component in FIG. 2, FIG. 7, FIG. 12, and FIG. 33.

[21] To define a "passive" (e.g., suggesting less effort) state of mind description a meditation exercise is conducted wherein the user meditates to a script which helps them visualize their future self in a peaceful setting (usually done by an expert in presenting such exercises). Based on the user's experience, the user enters a description of their experience, a name which represents their future self (something other than their given name), and chooses three one-word descriptions that represent their "passive" or relaxed state of mind (e.g., creativity, clarity, and satisfaction). RULE: The one-word descriptors must follow the rule: "incorporates <one-word descriptor> in your discussion topic". These data items described above are stored in the appropriate data structures. Refer to the STATE OF MIND CONSTRUCTOR 8 component in FIG. 2, FIG. 7, FIG. 12, and FIG. 33.

[22] To define an "active" (e.g., suggesting more effort) state of mind description another exercise is conducted wherein the user initiates a discussion regarding their life peak experience (usually done with an expert in conducting such exercises). Based on the user's experience, the user enters a description of their experience and chooses three one-word descriptions that represent their "active" or motivated state of mind (e.g., freedom, vitality, connecting). RULE: The one-word descriptors must follow the rule: "incorporates <one-word descriptor> in your discussion topic". These data items described above are stored in the appropriate data structures. Refer to the STATE OF MIND CONSTRUCTOR 8 component in FIG. 2, FIG. 7, FIG. 12, and FIG. 33.

[23] The facilitator defines a fundamental category for each motivational attribute (e.g., need, stress reaction, interest, and strength). As defined in one embodiment of the application, the fundamental categories defined are respectively: confidence, patience, devotion, and honor. For example, to define a fundamental category for the motivational attribute "need" the facilitator may find that "confidence" (e.g., fundamental category) is achieved when the motivational attribute "needs" are manageable. And, to define a fundamental category for the motivational attribute "stress reaction" the facilitator may find that "patience" (e.g., fundamental category) is achieved when the motivational attribute "stress reactions" are manageable. And, to define a fundamental category for the motivational attribute "interests" the facilitator may find that "devotion" (e.g., fundamental category) is achieved when the motivational attribute "interests" are manageable. And, to define a fundamental category for the motivational attribute "strength" the facilitator may find that "honor" (e.g., fundamental category) is achieved when the motivational attribute "strengths" are manageable. Refer to the FUNDAMENTAL CATEGORY CONSTRUCTOR 14 component in FIG. 3 and FIG. 7.

[24] Update the linguistic constructs in the Linguistic Constructs Table in FIG. 29 according to the fundamental categories (e.g., confidence, patience, devotion, and honor) defined by the facilitator in step 25 above and according to the design of the Relationship Anatomy Model in FIG. 30a through 30f. Refer to the Linguistic Constructs Table Detailed Description section in this application and FIG. 7.

[25] The facilitator defines a set of motivational coping techniques for every fundamental category. For at least one embodiment of this application, each motivational coping technique is a verb which can also be a transitive verb. For each fundamental category there is at least one motivational coping technique defined for each quadrant cache, and there are at least two motivational coping techniques defined that represent a "passive" (e.g., suggesting less effort) state of mind (refer to column 1 in FIG. 30f) and at least two motivational coping techniques defined that represent an "active" (e.g., suggesting more effort) state of mind (refer to column 2 in FIG. 30f). Note however, that for any given discussion topic evaluation, a "passive" motivational coping technique may represent column 2 (i.e., visa versa) and an "active" motivational coping technique may represent column 1 (i.e., visa versa). Each set (e.g., two) of "passive" and "active" motivational coping techniques are designed according to the coping evolution requirements (refer to The Detailed Description of the Coping Evolution Requirements). In general, the coping evolution represents the awareness level (e.g., vertical axis of the relationship anatomy model in FIG. 30a through 30f) of a motivational coping technique according to a "passive" and "active" state of mind for a fundamental category. For example, for the fundamental category "confidence" the "passive" state of mind motivational coping techniques are defined by the facilitator as "allow" and "accept". The motivational coping technique "allow" is defined for quadrant cache 1 and quadrant cache 3 which represents the "lower" awareness level quadrant cache (refer to FIG. 30b). The motivational coping technique "accept" is defined for quadrant cache 2 and quadrant cache 4 which represents the "higher" awareness level quadrant cache (refer to FIG. 30b). As a result, through experimentation and observation it is believed that a typical user may "allow" an attitudinal trait description instance before "accept(ing)" an attitudinal trait description instance. The facilitator defines the "active" motivational coping techniques as "maintain" (representing quadrant cache 1 and quadrant cache 3) and "support" (representing quadrant cache 2 and quadrant cache 4). Refer to the MOTIVATIONAL COPING TECHNIQUE CONSTRUCTOR 15 component in FIG. 3 and refer to the Linguistic Constructs Table Detailed Description section in this application to understand how motivational coping techniques are defined according to the Relationship Anatomy Model in FIG. 30a through 30f and FIG. 7.

[26] For the fundamental category "patience", the facilitator defines the "passive" motivational coping techniques as "excuse" (representing quadrant cache 1 and quadrant cache 3) and "forgive" (representing quadrant cache 2 and quadrant cache 4). And the "active" motivational coping techniques are defined as "comprehend" (representing quadrant cache 1 and quadrant cache 3) and "understand" (representing quadrant cache 2 and quadrant cache 4). Refer to step [27] above and to the MOTIVATIONAL COPING TECHNIQUE CONSTRUCTOR 15 component in FIG. 3 and refer to the Linguistic Constructs Table Detailed Description section in this application to understand how motivational coping techniques are defined according to the Relationship Anatomy Model in FIG. 30a through 30f and FIG. 7.

[27] For the fundamental category "devotion", the facilitator defines the "passive" motivational coping techniques as "consider" (representing quadrant cache 1 and quadrant cache 3) and "discover" (representing quadrant cache 2 and quadrant cache 4). And the "active" motivational coping techniques are defined as "acknowledge" (representing quadrant cache 1 and quadrant cache 3) and "fulfill" (representing quadrant cache 2 and quadrant cache 4). Refer to step [27] above and to the MOTIVATIONAL COPING TECHNIQUE CONSTRUCTOR 15 component in FIG. 3 and refer to the Linguistic Constructs Table Detailed Description section in this application to understand how motivational coping techniques are defined according to the Relationship Anatomy Model in FIG. 30a through 30f and FIG. 7.

[28] For the fundamental category "honor", the facilitator defines the "passive" motivational coping techniques as "observe" (representing quadrant cache 1 and quadrant cache 3) and "admire" (representing quadrant cache 2 and quadrant cache 4). And the "active" motivational coping techniques are defined as "appreciate" (representing quadrant cache 1 and quadrant cache 3) and "respect" (representing quadrant cache 2 and quadrant cache 4. Refer to step [27] above and to the MOTIVATIONAL COPING TECHNIQUE CONSTRUCTOR 15 component in FIG. 3 and refer to the Linguistic Constructs Table Detailed Description section in this application to understand how motivational coping techniques are defined according to the Relationship Anatomy Model in FIG. 30a through 30f and FIG. 7.

[29] Update the linguistic constructs data in the Linguistic Constructs Table in FIG. 29 according to each set of motivational coping techniques for each fundamental category defined in steps 27 through 30 above according to the design of the Relationship Anatomy Model in FIG. 30a through 30f. Refer to the Linguistic Constructs Table Detailed Description section in this application and FIG. 7.

[30] The user creates an autobiography for every set of attitudinal trait descriptions classified in steps 6 through 21 above (shown in FIG. 31) for every fundamental category (e.g., confidence, patience, devotion, & honor). The user is presented with a series of autobiography statements which are generated from the AUTOBIOGRAPHY DEVELOPER 25 in FIG. 5 in the form of requesting the user to describe their perception of attitudinal trait descriptions "least like" and "most like" themselves based on autobiography statements which include the predefined motivational coping techniques in steps 27 through 30 above and as described in consecutive steps below. Refer to the Linguistic Constructs Table Detailed Description and Refer to FIGS. 7, 13, 17, and 18.

[31] For fundamental category A (e.g., confidence) in FIG. 44 the user is asked "1. Describe ways you allow or maintain others potential needs." The attitudinal trait descriptions labeled A.2.3 in FIG. 31 from quadrant 3 cache (e.g., personal control over scheduling, adequate notice of any change, and a definite plan in place) are displayed below the autobiography statement. Referring to the Linguistic Constructs Table in FIG. 29, you'll find that A.2.3QCache3 is populated twice within the column attitudinal trait description ID for record #3 and record #19. In record #3 you'll notice the motivational coping technique is "maintain" and in record #19 you'll notice the motivational coping technique is "allow". Therefore, the user is given a choice to either describe ways to "allow" or "maintain" the attitudinal trait descriptions which exist in A.2.3 in FIG. 31. This is indicative of the way a collection of attitudinal trait descriptions may be addressed by two different motivational coping techniques for a given autobiography statement. Also, in record #3 and #19 identified in the Linguistic Constructs Table in FIG. 29 you'll notice that the attitudinal trait description is "others potential needs". According to the Linguistic Constructs Detailed Description, this justifies the remaining part of the autobiography statement above. Refer to FIGS. 7, 13, 17, and 18.

[32] The user enters an answer for the autobiography statement 1 in FIG. 44 (the answer input area not shown), and the answer is stored in a data structure (the user enters their answer by clicking the yellow sticky note icon next to autobiography statement 1 in FIG. 44) and used later for printing the user's autobiography shown in FIG. 28. Refer to FIG. 7.

[33] For fundamental category A (e.g., confidence) in FIG. 44 the user is asked "2. Describe ways you accept or support others potentially important needs." The attitudinal trait descriptions labeled A.2.4 in FIG. 31 from quadrant 4 cache (e.g., an unemotional environment, an environment based on trust, and issues reduced to their simplest form) are displayed below the autobiography statement. Referring to the Linguistic Constructs Table in FIG. 29, you'll find that A.2.4QCache4 is populated twice within the column attitudinal trait description ID for record #4 and record #20. In record #4 you'll notice the motivational coping technique is "support" and in record #20 you'll notice the motivational coping technique is "accept". Therefore, the user is given a choice to either describe ways to "accept" or "support" the attitudinal trait descriptions which exist in A.2.4 in FIG. 31. This is indicative of the way a collection of attitudinal trait descriptions may be addressed by two different motivational coping techniques for a given autobiography statement. Also, in record #4 and #20 identified in the Linguistic Constructs Table in FIG. 29 you'll notice that the attitudinal traits description is "others potentially important needs". According to the Linguistic Constructs Detailed Description, this justifies the remaining part of the autobiography statement above. Refer to FIGS. 7, 13, 17, and 18.

[34] The user enters an answer for the autobiography statement 2 in FIG. 44 (the answer input area not shown), and the answer is stored in a data structure (the user enters their answer by clicking the yellow sticky note icon next to autobiography statement 2 in FIG. 44) and used later for printing the user's autobiography shown in FIG. 28. Refer to FIG. 7.

[35] For fundamental category A (e.g., confidence) in FIG. 44 the user is asked "3. Describe ways you allow or maintain your needs." The attitudinal trait descriptions labeled A.1.1 in FIG. 31 from quadrant 1 cache (e.g., plenty of time for complex decisions, a busy schedule, and only an outline to follow) are displayed below the autobiography statement. Referring to the Linguistic Constructs Table in FIG. 29, you'll find that A.1.1QCache1 is populated twice within the column attitudinal trait description ID for record #1 and record #17. In record #1 you'll notice the motivational coping technique is "allow" and in record #17 you'll notice the motivational coping technique is "maintain". Therefore, the user is given a choice to either describe ways to "allow" or "maintain" the attitudinal trait descriptions which exist in A.1.1 in FIG. 31. This is indicative of the way a collection of attitudinal trait descriptions may be addressed by two different motivational coping techniques for a given autobiography statement. Also, in record #1 and #17 identified in the Linguistic Constructs Table in FIG. 29 you'll notice that the attitudinal trait description is "your needs". According to the Linguistic Constructs Detailed Description, this justifies the remaining part of the autobiography statement above. Refer to FIGS. 7, 13, 17, and 18.

[36] The user enters an answer for the autobiography statement 3 in FIG. 44 (the answer input area not shown), and the answer is stored in a data structure (the user enters their answer by clicking the yellow sticky note icon next to autobiography statement 3 in FIG. 44) and used later for printing the user's autobiography shown in FIG. 28. Refer to FIG. 7.

[37] For fundamental category A (e.g., confidence) in FIG. 44 the user is asked "4. Describe ways you accept or support your most important needs." The attitudinal trait descriptions labeled A.1.2 in FIG. 31 from quadrant 2 cache (e.g., plenty of different calls on attention, an outlet for subjective issues, and a way to measure personal performance) are displayed below the autobiography statement. Referring to the Linguistic Constructs Table in FIG. 29, you'll find that A.1.2QCache2 is populated twice within the column attitudinal trait description ID for record #2 and record #18. In record #2 you'll notice the motivational coping technique is "accept" and in record #18 you'll notice the motivational coping technique is "support". Therefore, the user is given a choice to either describe ways to "accept" or "support" the attitudinal trait descriptions which exist in A.1.2 in FIG. 31. This is indicative of the way a collection of attitudinal trait descriptions may be addressed by two different motivational coping techniques for a given autobiography statement. Also, in record #2 and #18 identified in the Linguistic Constructs Table in FIG. 29 you'll notice that the attitudinal traits description is "your most important needs". According to the Linguistic Constructs Detailed Description, this justifies the remaining part of the autobiography statement above. Refer to FIGS. 7, 13, 17, and 18.

[38] The user enters an answer for the autobiography statement 4 in FIG. 44 (the answer input area not shown), and the answer is stored in a data structure (the user enters their answer by clicking the yellow sticky note icon next to autobiography statement 4 in FIG. 44) and used later for printing the user's autobiography shown in FIG. 28. Refer to FIG. 7.

Figure 45:
FIG. 45 shows a user interface wherein the user develops their autobiography for the fundamental category "patience".

[39] For fundamental category B (e.g., patience) in FIG. 45 the user is asked "1. Describe ways you excuse or comprehend others potential stress reactions." The attitudinal trait descriptions labeled B.2.3 in FIG. 31 from quadrant 3 cache (e.g., putting things off, over-insistence on following procedures, and failing to address issues of control) are displayed below the autobiography statement. Referring to the Linguistic Constructs Table in FIG. 29, you'll find that B.2.3QCache3 is populated twice within the column attitudinal trait description ID for record #7 and record #23. In record #7 you'll notice the motivational coping technique is "comprehend" and in record #23 you'll notice the motivational coping technique is "excuse". Therefore, the user is given a choice to either describe ways to "excuse" or "comprehend" the attitudinal trait descriptions which exist in B.2.3 in FIG. 31. This is indicative of the way a collection of attitudinal trait descriptions may be addressed by two different motivational coping techniques for a given autobiography statement. Also, in record #7 and #23 identified in the Linguistic Constructs Table in FIG. 29 you'll notice that the attitudinal trait description is "others potential stress reactions". This According to the Linguistic Constructs Detailed Description, this justifies the remaining part of the autobiography statement above. Refer to FIGS. 7, 13, 17, and 18.

[40] The user enters an answer for the autobiography statement 1 in FIG. 45 (the answer input area not shown), and the answer is stored in a data structure (the user enters their answer by clicking the yellow sticky note icon next to autobiography statement 1 in FIG. 45) and used later for printing the user's autobiography shown in FIG. 28. Refer to FIG. 7.

[41] For fundamental category B (e.g., patience) in FIG. 45 the user is asked "2. Describe ways you forgive or understand others potentially difficult stress reactions." The attitudinal trait descriptions labeled B.2.4 in FIG. 31 from quadrant 4 cache (e.g., failing to accept necessary change, being impulsive, and discomfort with unusual ideas) are displayed below the autobiography statement. Referring to the Linguistic Constructs Table in FIG. 29, you'll find that B.2.4QCache4 is populated twice within the column attitudinal trait description ID for record #8 and record #24. In record #8 you'll notice the motivational coping technique is "understand" and in record #24 you'll notice the motivational coping technique is "forgive". Therefore, the user is given a choice to either describe ways to "forgive" or "understand" the attitudinal trait descriptions which exist in B.2.4 in FIG. 31. This is indicative of the way a collection of attitudinal trait descriptions may be addressed by two different motivational coping techniques for a given autobiography statement. Also, in record #8 and #24 identified in the Linguistic Constructs Table in FIG. 29 you'll notice that the attitudinal trait description is "others potentially difficult stress reactions". According to the Linguistic Constructs Detailed Description, this justifies the remaining part of the autobiography statement above. Refer to FIGS. 7, 13, 17, and 18.

[42] The user enters an answer for the autobiography statement 2 in FIG. 45 (the answer input area not shown), and the answer is stored in a data structure (the user enters their answer by clicking the yellow sticky note icon next to autobiography statement 2 in FIG. 45) and used later for printing the user's autobiography shown in FIG. 28. Refer to FIG. 7.

[43] For fundamental category B (e.g., patience) in FIG. 45 the user is asked "3. Describe ways you excuse or comprehend your stress reactions." The attitudinal trait descriptions labeled B.1.1 in FIG. 31 from quadrant 1 cache (e.g., weakness in follow-through, getting distracted too easily, and being different for its own sake) are displayed below the autobiography statement. Referring to the Linguistic Constructs Table in FIG. 29, you'll find that B.1.1QCache1 is populated twice within the column attitudinal trait description ID for record #5 and record #21. In record #5 you'll notice the motivational coping technique is "excuse" and in record #21 you'll notice the motivational coping technique is "comprehend". Therefore, the user is given a choice to either describe ways to "excuse" or "comprehend" the attitudinal trait descriptions which exist in B.1.1 in FIG. 31. This is indicative of the way a collection of attitudinal trait descriptions may be addressed by two different motivational coping techniques for a given autobiography statement. Also, in record #5 and #21 identified in the Linguistic Constructs Table in FIG. 29 you'll notice that the attitudinal trait description is "your stress reactions". According to the Linguistic Constructs Detailed Description, this justifies the remaining part of the autobiography statement above. Refer to FIGS. 7, 13, 17, and 18.

[44] The user enters an answer for the autobiography statement 3 in FIG. 45 (the answer input area not shown), and the answer is stored in a data structure (the user enters their answer by clicking the yellow sticky note icon next to autobiography statement 3 in FIG. 45) and used later for printing the user's autobiography shown in FIG. 28. Refer to FIG. 7.

[45] For fundamental category B (e.g., patience) in FIG. 45 the user is asked "4. Describe ways you forgive or understand your most difficult stress reactions." The attitudinal trait descriptions labeled B.1.2 in FIG. 31 from quadrant 2 cache (e.g., becoming domineering and controlling, indecision when pressured, and failing to delegate when necessary) are displayed below the autobiography statement. Referring to the Linguistic Constructs Table in FIG. 29, you'll find that B.1.2QCache2 is populated twice within the column attitudinal trait description ID for record #6 and record #22. In record #6 you'll notice the motivational coping technique is "forgive" and in record #22 you'll notice the motivational coping technique is "understand". Therefore, the user is given a choice to either describe ways to "forgive" or "understand" the attitudinal trait descriptions which exist in B.1.2 in FIG. 31. This is indicative of the way a collection of attitudinal trait descriptions may be addressed by two different motivational coping techniques for a given autobiography statement. Also, in record #6 and #22 identified in the Linguistic Constructs Table in FIG. 29 you'll notice that the attitudinal trait description is "your most difficult stress reactions". According to the Linguistic Constructs Detailed Description, this justifies the remaining part of the autobiography statement above. Refer to FIGS. 7, 13, 17, and 18.

[46] The user enters an answer for the autobiography statement 4 in FIG. 45 (the answer input area not shown), and the answer is stored in a data structure (the user enters their answer by clicking the yellow sticky note icon next to autobiography statement 4 in FIG. 45) and used later for printing the user's autobiography shown in FIG. 28. Refer to FIG. 7.

[47] For fundamental category C (e.g., devotion) in FIG. 46 the user is asked "1. Describe ways you acknowledge or consider others potential interests." The attitudinal trait descriptions labeled C.2.3 in FIG. 31 from quadrant 3 cache (e.g., completing any details, a minimum of directive involvement, and hard work-rewarding self motivation) are displayed below the autobiography statement. Referring to the Linguistic Constructs Table in FIG. 29, you'll find that C.2.3QCache3 is populated twice within the column attitudinal trait description ID for record #11 and record #27. In record #11 you'll notice the motivational coping technique is "acknowledge" and in record #27 you'll notice the motivational coping technique is "consider". Therefore, the user is given a choice to either describe ways to "acknowledge" or "consider" the attitudinal trait descriptions which exist in C.2.3 in FIG. 31. This is indicative of the way a collection of attitudinal trait descriptions may be addressed by two different motivational coping techniques for a given autobiography statement. Also, in record #11 and #27 identified in the Linguistic Constructs Table in FIG. 29 you'll notice that the attitudinal trait description is "others potential interests". According to the Linguistic Constructs Detailed Description, this justifies the remaining part of the autobiography statement above. Refer to FIGS. 7, 13, 17, and 18.

[48] The user enters an answer for the autobiography statement 1 in FIG. 46 (the answer input area not shown), and the answer is stored in a data structure (the user enters their answer by clicking the yellow sticky note icon next to autobiography statement 1 in FIG. 46) and used later for printing the user's autobiography shown in FIG. 28. Refer to FIG. 7.

[49] For fundamental category C (e.g., devotion) in FIG. 46 the user is asked "2. Describe ways you fulfill or discover others potentially passionate interests." The attitudinal trait descriptions labeled C.2.4 in FIG. 31 from quadrant 4 cache (e.g., exercising strong managerial authority, approaching issues holistically, and approaching problems factually and logically) are displayed below the autobiography statement. Referring to the Linguistic Constructs Table in FIG. 29, you'll find that C.2.4QCache4 is populated twice within the column attitudinal trait description ID for record #12 and record #28. In record #12 you'll notice the motivational coping technique is "fulfill" and in record #28 you'll notice the motivational coping technique is "discover". Therefore, the user is given a choice to either describe ways to "fulfill" or "discover" the attitudinal trait descriptions which exist in C.2.4 in FIG. 31. This is indicative of the way a collection of attitudinal trait descriptions may be addressed by two different motivational coping techniques for a given autobiography statement. Also, in record #12 and #28 identified in the Linguistic Constructs Table in FIG. 29 you'll notice that the attitudinal trait description is "others potentially passionate interests". According to the Linguistic Constructs Detailed Description, this justifies the remaining part of the autobiography statement above. Refer to FIGS. 7, 13, 17, and 18.

[50] The user enters an answer for the autobiography or statement 2 in FIG. 46 (the answer input area not shown), and the answer is stored in a data structure (the user enters their answer by clicking the yellow sticky note icon next to autobiography statement 2 in FIG. 46) and used later for printing the user's autobiography shown in FIG. 28. Refer to FIG. 7.

[51] For fundamental category C (e.g., devotion) in FIG. 46 the user is asked "3. Describe ways you acknowledge or consider your interests." The attitudinal trait descriptions labeled C.1.1 in FIG. 31 from quadrant 1 cache (e.g., positive relationships and mutual trust, a commitment to major responsibilities, and imagination and intuitiveness) are displayed below the autobiography statement. Referring to the Linguistic Constructs Table in FIG. 291, you'll find that C.1.1QCache1 is populated twice within the column attitudinal trait description ID for record #9 and record #25. In record #9 you'll notice the motivational coping technique is "consider" and in record #25 you'll notice the motivational coping technique is "acknowledge". Therefore, the user is given a choice to either describe ways to "consider" or "acknowledge" the attitudinal trait descriptions which exist in C.1.1 in FIG. 31. This is indicative of the way a collection of attitudinal trait descriptions may be addressed by two different motivational coping techniques for a given autobiography statement. Also, in record #9 and #25 identified in the Linguistic Constructs Table in FIG. 29 you'll notice that the attitudinal trait description is "your interests". According to the Linguistic Constructs Detailed Description, this justifies the remaining part of the autobiography statement above. Refer to FIGS. 7, 13, 17, and 18.

[52] The user enters an answer for the autobiography statement 3 in FIG. 46 (the answer input area not shown), and the answer is stored in a data structure (the user enters their answer by clicking the yellow sticky note icon next to autobiography statement 3 in FIG. 46) and used later for printing the user's autobiography shown in FIG. 28. Refer to FIG. 7.

[53] For fundamental category C (e.g., devotion) in FIG. 46 the user is asked "4. Describe ways you fulfill or discover your most passionate interests." The attitudinal trait descriptions labeled C.1.2 in FIG. 31 from quadrant 2 cache (e.g., educational approaches to development, comfort in problem solving and crisis intervention, and managing through knowledge and expertise) are displayed below the autobiography statement. Referring to the Linguistic Constructs Table in FIG. 29, you'll find that C.1.2QCache2 is populated twice within the column attitudinal trait description ID for record #10 and record #26. In record #10 you'll notice the motivational coping technique is "discover" and in record #22 you'll notice the motivational coping technique is "fulfill". Therefore, the user is given a choice to either describe ways to "fulfill" or "discover" the attitudinal trait descriptions which exist in C.1.2 in FIG. 31. This is indicative of the way a collection of attitudinal trait descriptions may be addressed by two different motivational coping techniques for a given autobiography statement. Also, in record #10 and #26 identified in the Linguistic Constructs Table in FIG. 29 you'll notice that the attitudinal trait description is "your most passionate interests". According to the Linguistic Constructs Detailed Description, this justifies the remaining part of the autobiography statement above. Refer to FIGS. 7, 13, 17, and 18.

[54] The user enters an answer for the autobiography statement 4 in FIG. 46 (the answer input area not shown), and the answer is stored in a data structure (the user enters their answer by clicking the yellow sticky note icon next to autobiography statement 4 in FIG. 46) and used later for printing the user's autobiography shown in FIG. 28. Refer to FIG. 7.

[55] For fundamental category D (e.g., honor) in FIG. 47 the user is asked "1. Describe ways you appreciate or observe others potential strengths." The attitudinal trait descriptions labeled D.2.3 in FIG. 31 from quadrant 3 cache (e.g., concentrates attention well, oriented toward individual advantage, and able to work well alone) are displayed below the autobiography statement. Referring to the Linguistic Constructs Table in FIG. 29, you'll find that D.2.3QCache3 is populated twice within the column attitudinal trait description ID for record #15 and record #31. In record #15 you'll notice the motivational coping technique is "appreciate" and in record #31 you'll notice the motivational coping technique is "observe". Therefore, the user is given a choice to either describe ways to "appreciate" or "observe" the attitudinal trait descriptions which exist in D.2.3 in FIG. 31. This is indicative of the way a collection of attitudinal trait descriptions may be addressed by two different motivational coping techniques for a given autobiography statement. Also, in record #15 and #31 identified in the Linguistic Constructs Table in FIG. 29 you'll notice that the attitudinal trait description is "others potential strengths". According to the Linguistic Constructs Detailed Description, this justifies the remaining part of the autobiography statement above. Refer to FIGS. 7, 13, 17, and 18.

[56] The user enters an answer for the autobiography statement 1 in FIG. 47 (the answer input area not shown), and the answer is stored in a data structure (the user enters their answer by clicking the yellow sticky note icon next to autobiography statement 1 in FIG. 47) and used later for printing the user's autobiography shown in FIG. 28. Refer to FIG. 7.

[57] For fundamental category D (e.g., honor) in FIG. 47 the user is asked "2. Describe ways you respect or admire others potentially consistent strengths." The attitudinal trait descriptions labeled D.2.4 in FIG. 31 from quadrant 4 cache (e.g., insightful and intuitive, likes to reflect before acting, and low-key in exercise of authority) are displayed below the autobiography statement. Referring to the Linguistic Constructs Table in FIG. 29, you'll find that D.2.4QCache4 is populated twice within the column attitudinal trait description ID for record #16 and record #32. In record #16 you'll notice the motivational coping technique is "respect" and in record #32 you'll notice the motivational coping technique is "admire". Therefore, the user is given a choice to either describe ways to "respect" or "admire" the attitudinal trait descriptions which exist in D.2.4 in FIG. 31. This is indicative of the way a collection of attitudinal trait descriptions may be addressed by two different motivational coping techniques for a given autobiography statement. Also, in record #16 and #32 identified in the Linguistic Constructs Table in FIG. 29 you'll notice that the attitudinal trait description is "others potentially consistent strengths". According to the Linguistic Constructs Detailed Description, this justifies the remaining part of the autobiography statement above. Refer to FIGS. 7, 13, 17, and 18.

[58] The user enters an answer for the autobiography statement 2 in FIG. 47 (the answer input area not shown), and the answer is stored in a data structure (the user enters their answer by clicking the yellow sticky note icon next to autobiography statement 2 in FIG. 47) and used later for printing the user's autobiography shown in FIG. 28. Refer to FIG. 7.

[59] For fundamental category D (e.g., honor) in FIG. 47 the user is asked "3. Describe ways you appreciate or observe your strengths." The attitudinal trait descriptions labeled D.1.1 in FIG. 31 from quadrant 1 cache (e.g., takes direct action to get things done, direct and straightforward, and directive and commanding) are displayed below the autobiography statement. Referring to the Linguistic Constructs Table in FIG. 29, you'll find that D.1.1QCache1 is populated twice within the column attitudinal trait description ID for record #13 and record #29. In record #13 you'll notice the motivational coping technique is "observe" and in record #29 you'll notice the motivational coping technique is "appreciate". Therefore, the user is given a choice to either describe ways to "appreciate" or "observe" the attitudinal trait descriptions which exist in D.1.1 in FIG. 31. This is indicative of the way a collection of attitudinal trait descriptions may be addressed by two different motivational coping techniques for a given autobiography statement. Also, in record #13 and #29 identified in the Linguistic Constructs Table in FIG. 29 you'll notice that the attitudinal trait description is "your strengths". According to the Linguistic Constructs Detailed Description, this justifies the remaining part of the autobiography statement above. Refer to FIGS. 7, 13, 17, and 18.

[60] The user enters an answer for the autobiography statement 3 in FIG. 47 (the answer input area not shown), and the answer is stored in a data structure (the user enters their answer by clicking the yellow sticky note icon next to autobiography statement 3 in FIG. 47) and used later for printing the user's autobiography shown in FIG. 28. Refer to FIG. 7.

[61] For fundamental category D (e.g., honor) in FIG. 47 the user is asked "4. Describe ways you respect or admire your most consistent strengths." The attitudinal trait descriptions labeled D.1.2 in FIG. 31 from quadrant 2 cache (e.g., likes a variety of simultaneous tasks, oriented toward general benefit, and friendly and easy to know) are displayed below the autobiography statement. Referring to the Linguistic Constructs Table in FIG. 29, you'll find that D.1.2QCache2 is populated twice within the column attitudinal trait description ID for record #14 and record #30. In record #14 you'll notice the motivational coping technique is "admire" and in record #30 you'll notice the motivational coping technique is "respect". Therefore, the user is given a choice to either describe ways to "respect" or "admire" the attitudinal trait descriptions which exist in D.1.2 in FIG. 31. This is indicative of the way a collection of attitudinal trait descriptions may be addressed by two different motivational coping techniques for a given autobiography statement. Also, in record #14 and #30 identified in the Linguistic Constructs Table in FIG. 29 you'll notice that the attitudinal trait description is "your most consistent strengths". According to the Linguistic Constructs Detailed Description, this justifies the remaining part of the autobiography statement above. Refer to FIGS. 7, 13, 17, and 18.

[62] The user enters an answer for the autobiography statement 4 in FIG. 47 (the answer input area not shown), and the answer is stored in a data structure (the user enters their answer by clicking the yellow sticky note icon next to autobiography statement 4 in FIG. 47) and used later for printing the user's autobiography shown in FIG. 28. Refer to FIG. 7.

Figure 54:
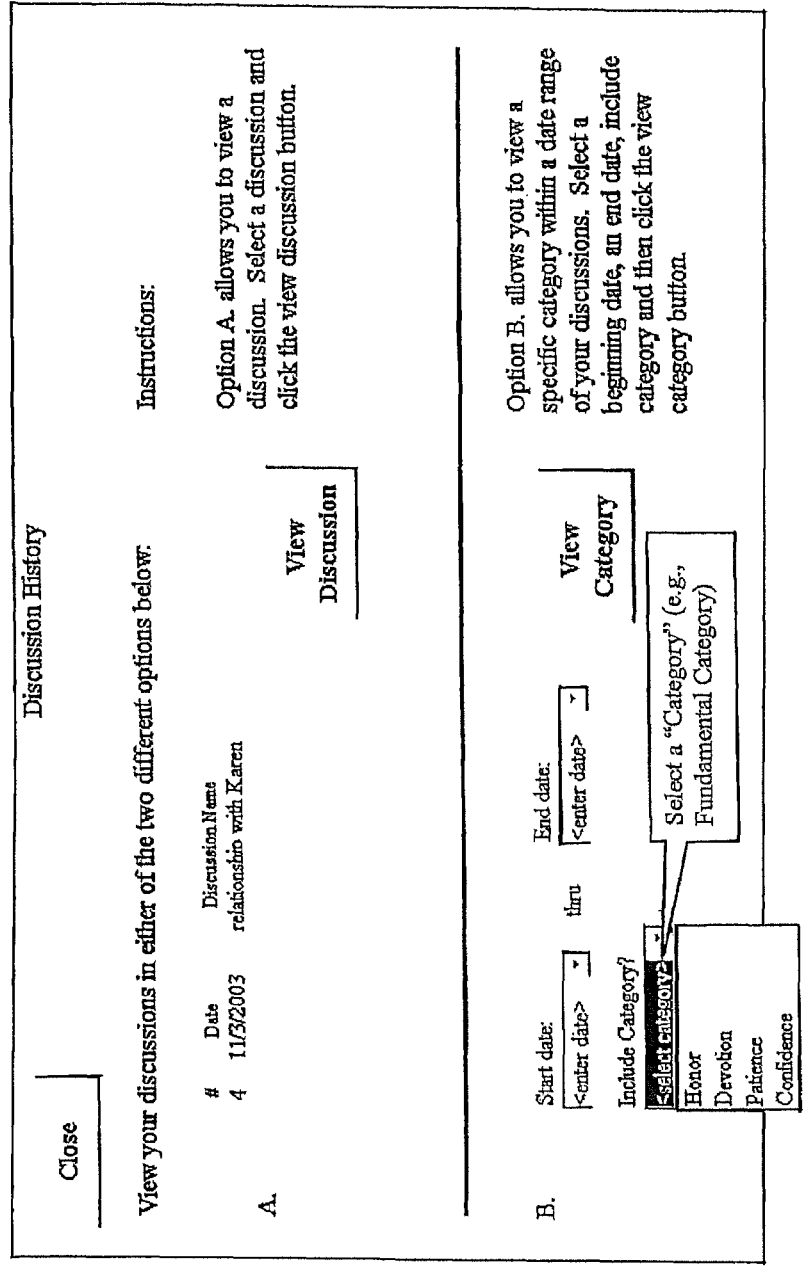
FIG. 54 shows a user interface wherein the user may select two types of reports for viewing their journal entries based on their discussion topics.

[63] The user may print their autobiography. The autobiography contains all the user's answers to each of the four collections of attitudinal trait descriptions for every fundamental category (e.g., confidence, patience, devotion, and honor). The fundamental categories represent each or section of the user's autobiography report. Refer to FIG. 28 and FIG. 54.

Figure 4:
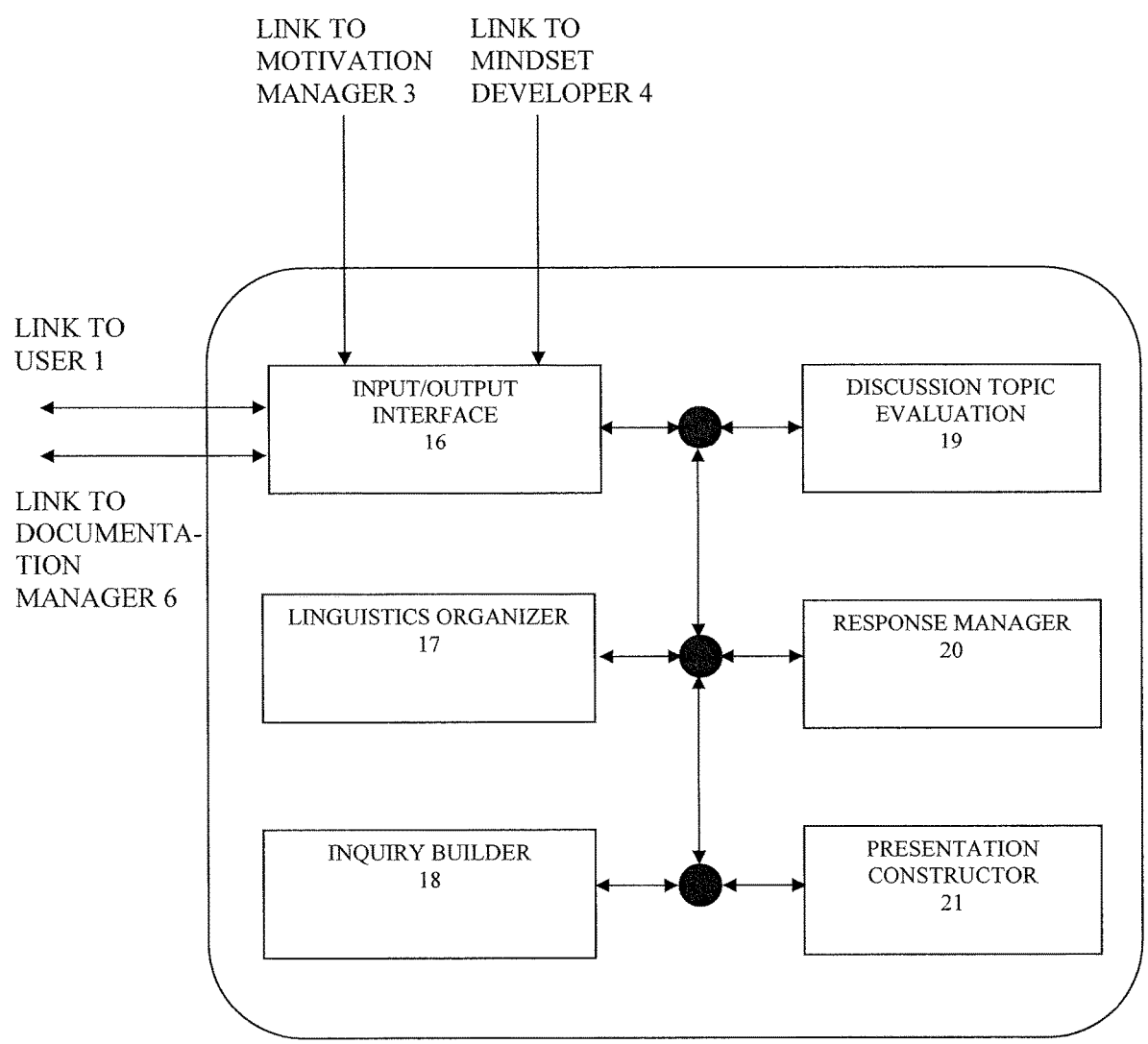
FIG. 4 shows a block diagram of the component called DISCUSSION GENERATOR 5. This component aids a user in evaluating a discussion topic and generates inquiries back to the user wherein the user is able to reflect and investigate a user's desired discussion topic.
Figure 5:
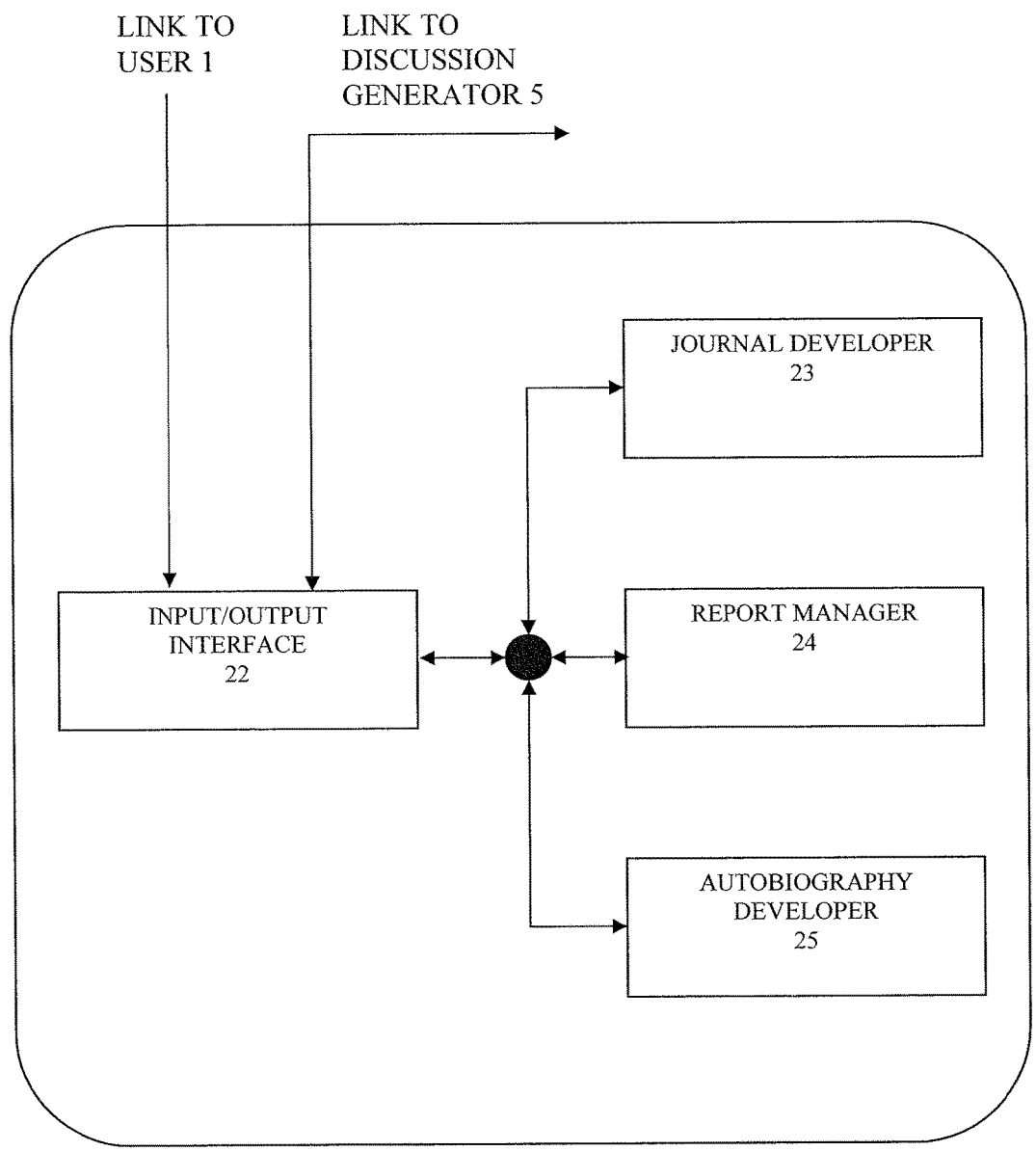
FIG. 5 shows a block diagram of the component called DOCUMENTATION MANAGER 6. This component aids the user in developing a personalized autobiography, entering journal entries based on discussion topic evaluations, viewing reports to review their journal entries and entries related to their autobiography.
Figure 6B:
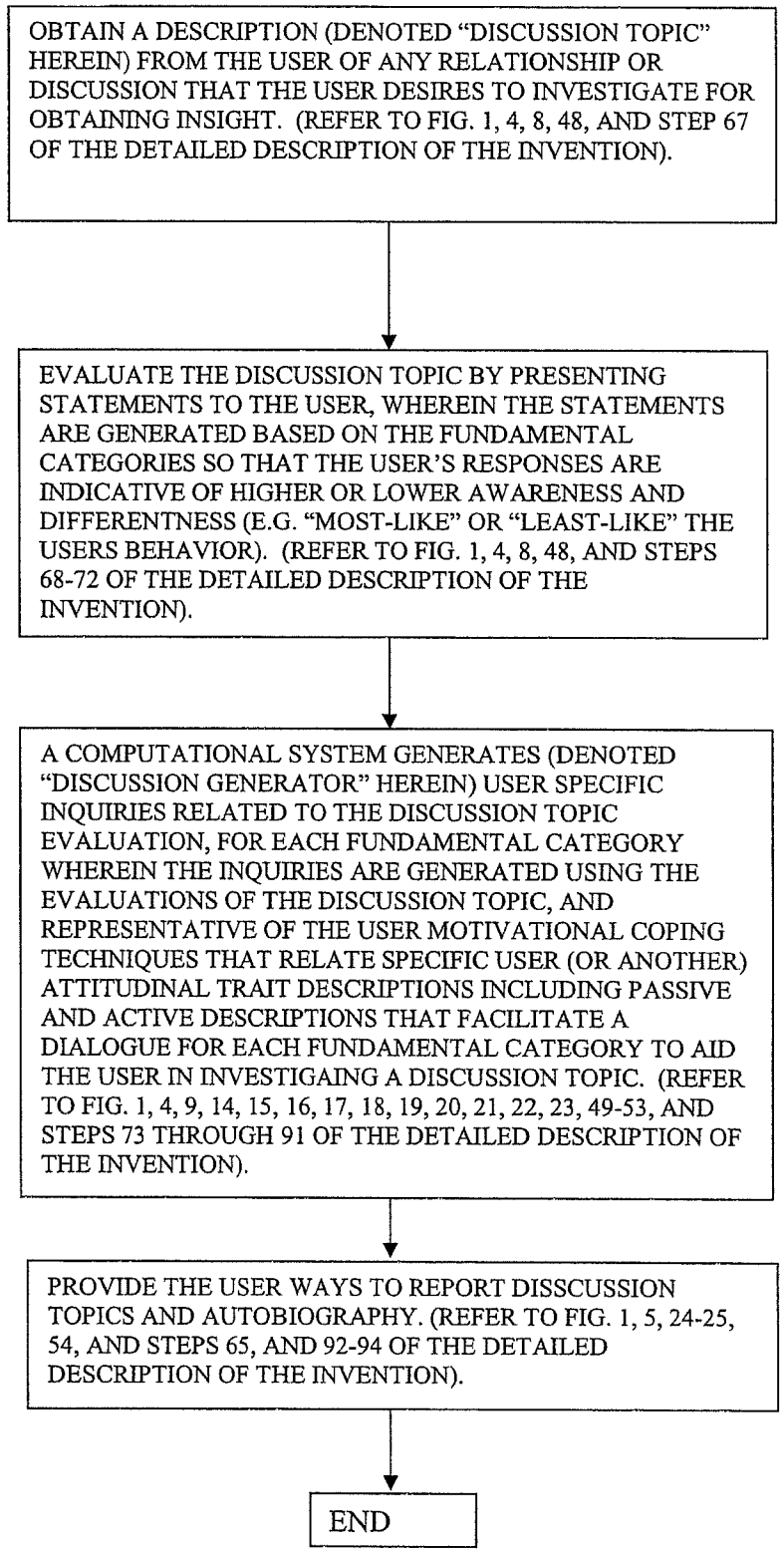

[64] The next series of steps focus on the DISCUSSION GENERATOR 5 component in FIG. 4 wherein the user defines and evaluates a discussion topic and then is presented with inquiries based on the evaluation of the discussion topic wherein the user may then reflect upon or investigate the discussion topic and enter journal entries as a result of their reflection and investigation.

Figure 8:
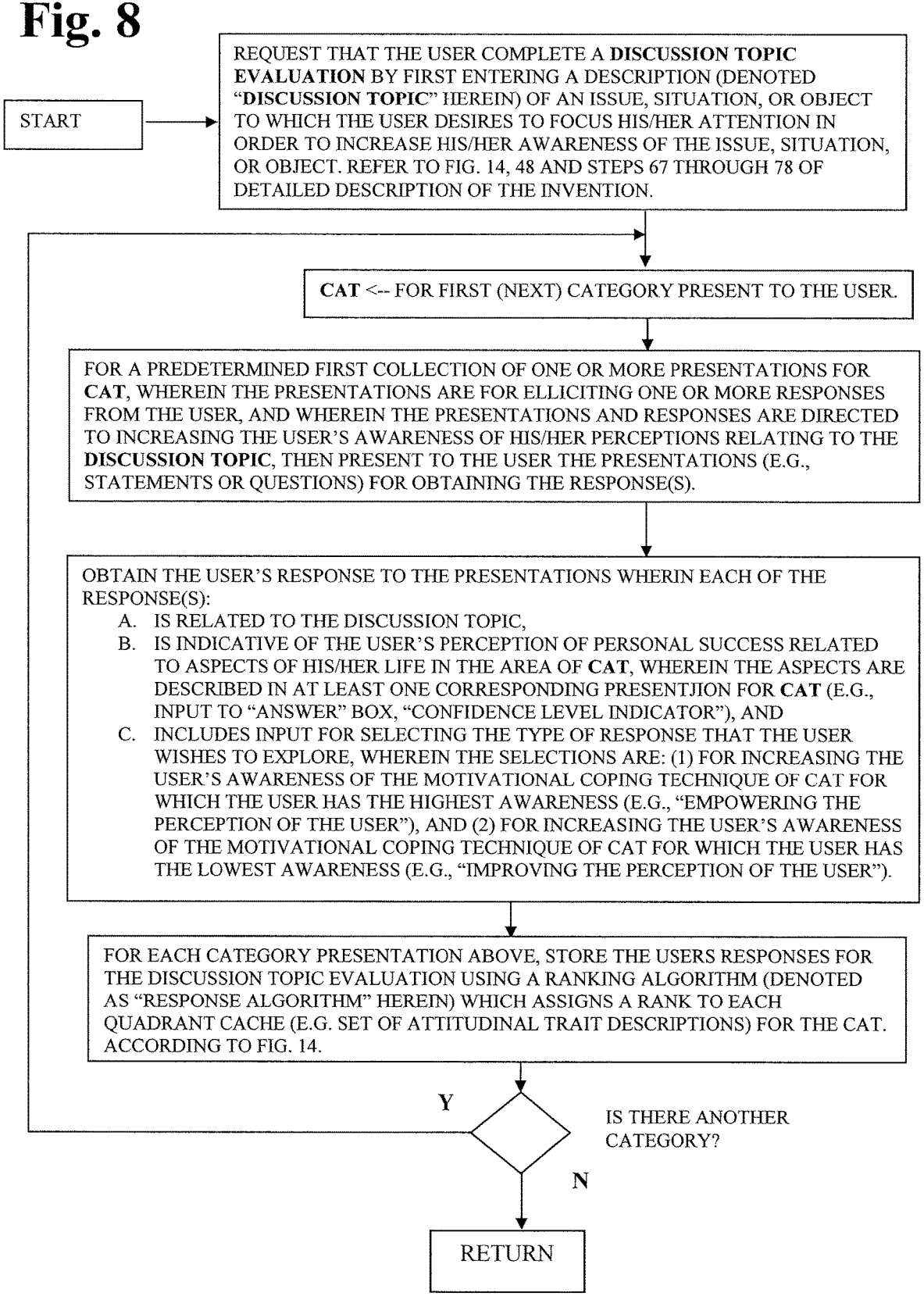
FIG. 8 shows a flowchart that represents a user in defining a discussion topic and evaluating such a discussion topic based on true/untrue statements that correspond to each fundamental category (e.g., confidence) which require a rank of 1 to 10, a confidence level indicator of "high" or "low", and a response type of "empower" or "improve".
Figure 9A:
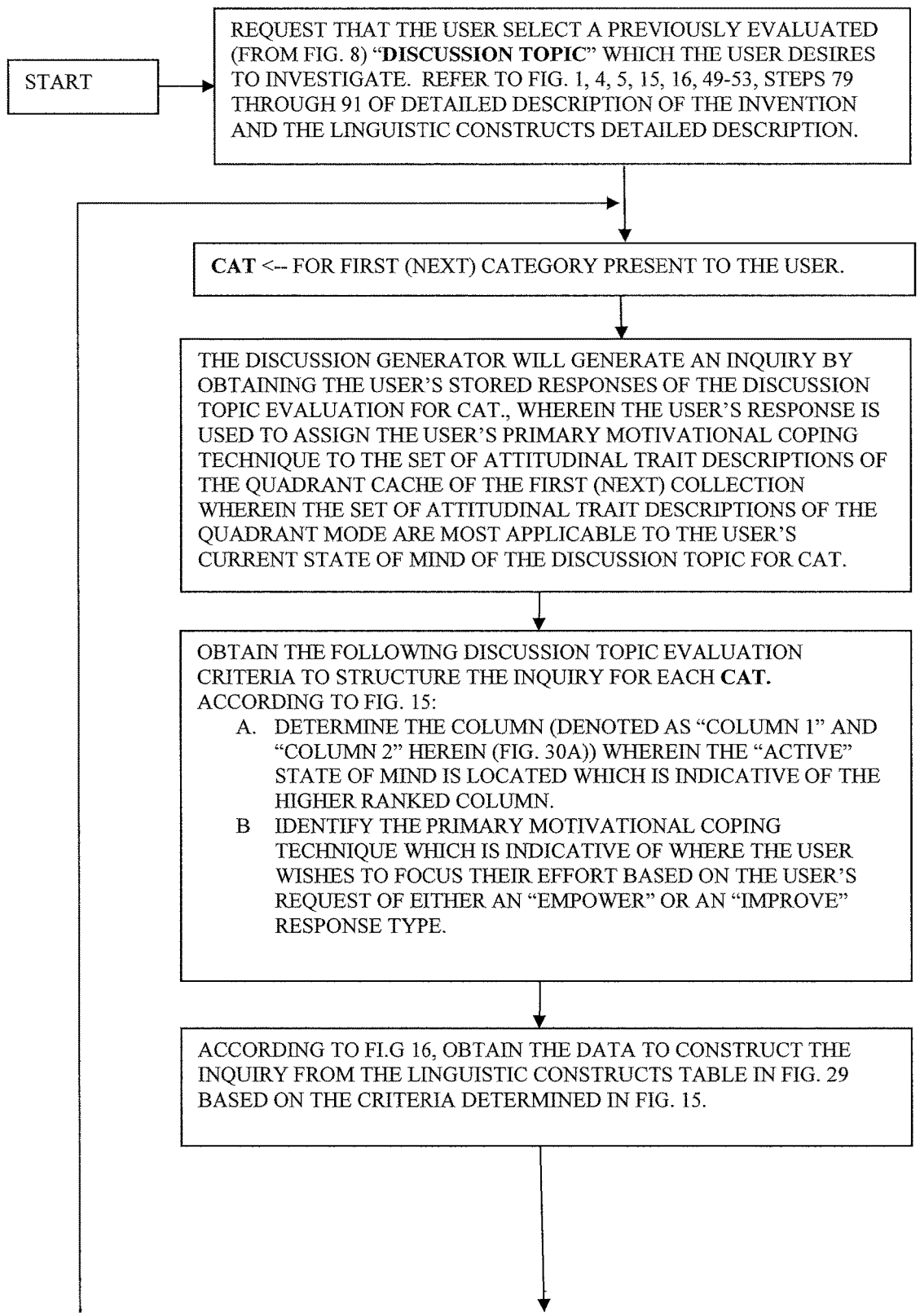
Figure 48:
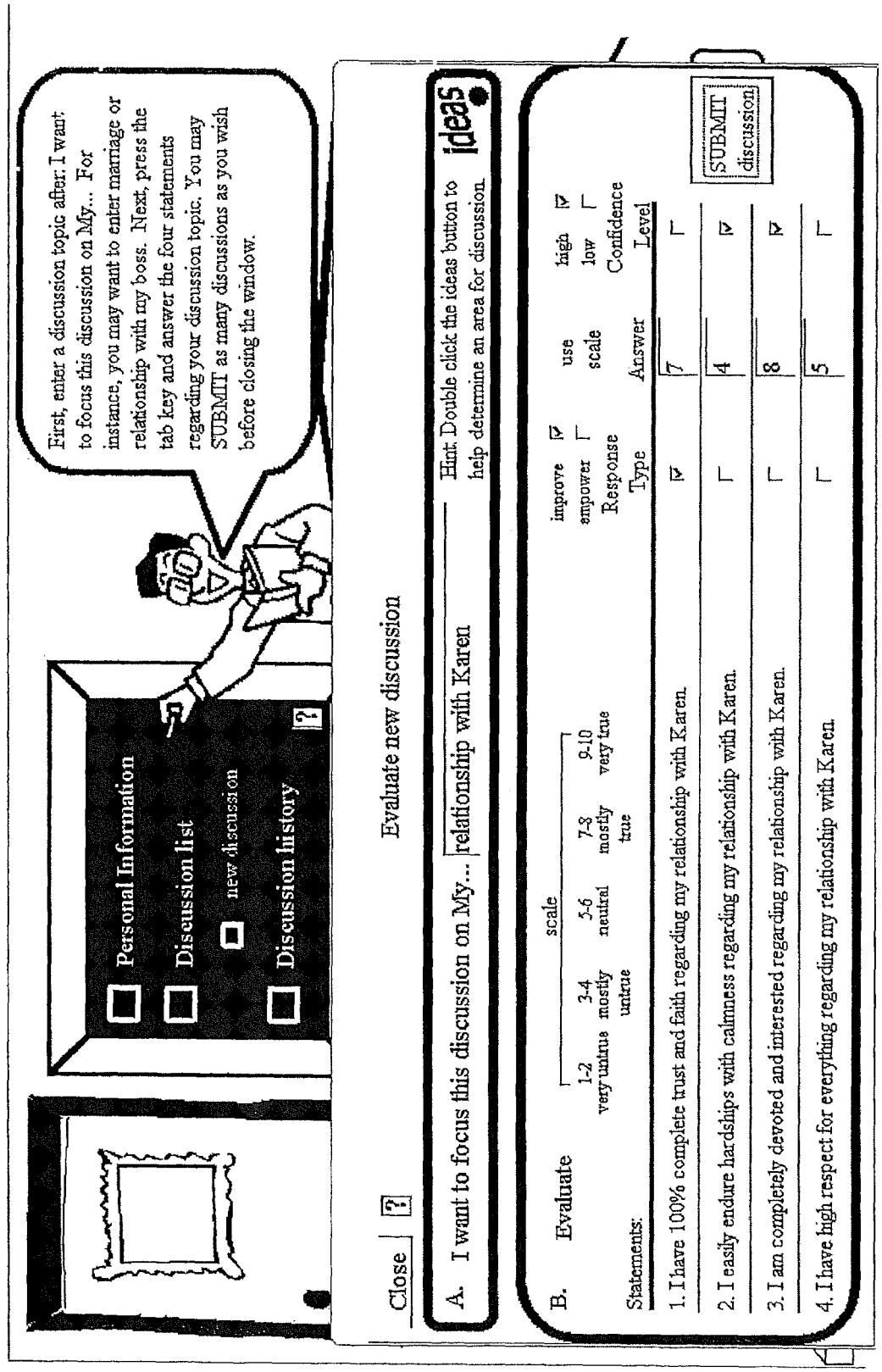
FIG. 48 shows a user interface that aids the user in defining a discussion topic and evaluating such a discussion topic based on answering true/untrue statements with a rank of 1 to 10, a confidence level indicator of "high" or "low", and a response type of "empower" or "improve".

[65] The user defines a discussion topic of their liking in which the phrase "I want to discuss my . . . " aids the user in defining a discussion topic. For example, a discussion topic may be health, work, family, children, relationship with Karen, relationship with my boss, etc. For the purpose of demonstrating an example for one embodiment in this application, the user will choose "relationship with Karen". Refer to FIG. 48 and FIG. 8.

[66] Next, the user will rank four true/untrue statements from 1 to 10 where 1 is mostly untrue and 10 is mostly true. Each true/untrue statement is indicative of a fundamental category (e.g., confidence) for each of the corresponding motivational attributes (e.g., need). Also, each true/untrue statement requires that the user select a confidence level indicator which demonstrates whether they have a "low" confidence level or lack of assurance in their score or a "high" confidence level or assurance in their score. A "low" confidence level in their score would indicate more of a guess. In addition, each true/untrue statement requires the user to indicate a desired response type of "empower" or "improve". An "empower" response type will (e.g., described later in detail) generate an inquiry back to the user that is indicative of the user's strongest perception of the discussion topic and an "improve" response type will generate an inquiry back to the user that is indicative of the user's weakest perception of the discussion topic. Refer to FIG. 48 and FIG. 8.

[67] Fundamental category A (denoted as "confidence" herein) structures its true/untrue statement (the portion of the true/untrue statement in [ ] is constant for every discussion topic evaluation) as: "[I have 100% complete faith and trust regarding my] 'relationship with Karen'". The user answers the true/untrue statement as 7 (e.g., good ranking range). Also, the user decides to indicate a "low" confidence level in their rank and an "improve" response type. Refer to FIG. 48 and FIG. 8.

[68] Fundamental category B (denoted as "patience" herein) structures its true/untrue statement (the portion of the true/untrue statement in [ ] is constant for every discussion topic evaluation) as: "[I easily endure hardships with calmness regarding my] 'relationship with Karen'". The user answers the true/untrue statement as 4 (i.e., poor ranking range). Also, the user decides to indicate a "high" confidence level in their answer and an "empower" response type. Refer to FIG. 48 and FIG. 8.

[69] Fundamental category C (denoted as "devotion" herein) structures its true/untrue statement (the portion of the true/untrue statement in [ ] is constant for every discussion topic evaluation) as: "[I am completely devoted and interested regarding my] 'relationship with Karen'". The user answers the true/untrue statement as 8 (i.e., good ranking range). Also, the user decides to indicate a "high" confidence level in their answer and an "empower" response type. Refer to FIG. 48 and FIG. 8.

[70] Fundamental category D (denoted as "honor" herein) structures its true/untrue statement (the portion of the true/untrue statement in [ ] is constant for every discussion topic evaluation) as: "[I have high respect for everything regarding my] 'relationship with Karen'". The user answers the true/untrue statement as 5 (i.e., poor ranking range). Also, the user decides to indicate a "low" confidence level in their answer and an "empower" response type. Refer to FIG. 48 and FIG. 8.

Figure 14:
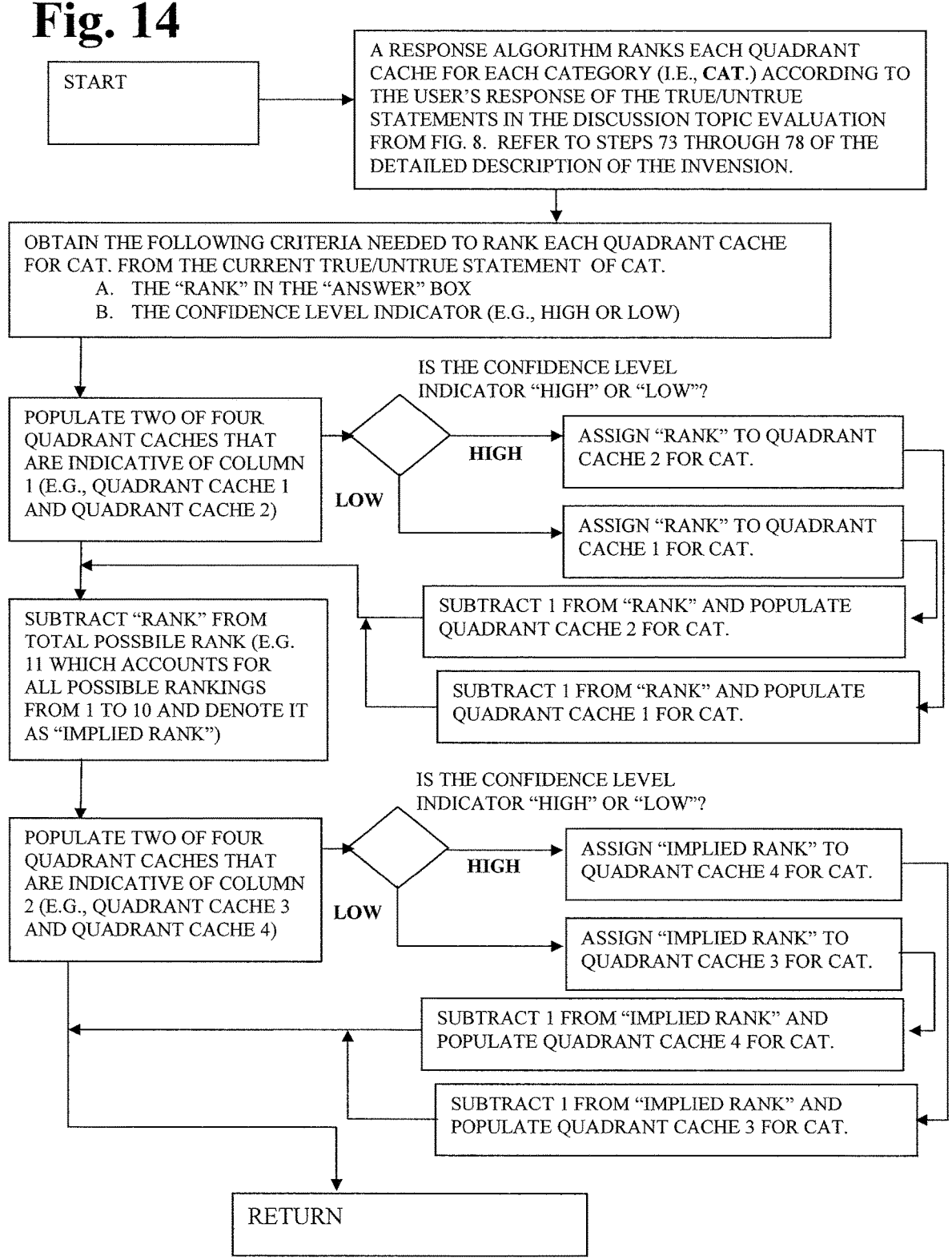
FIG. 14 shows a flowchart that represents the response algorithm which ranks each quadrant cache for each fundamental category (e.g., confidence) when a user submits a discussion topic evaluation (e.g., this algorithm measure a users perception as it relates to each fundamental category for a discussion topic).
Figure 15:
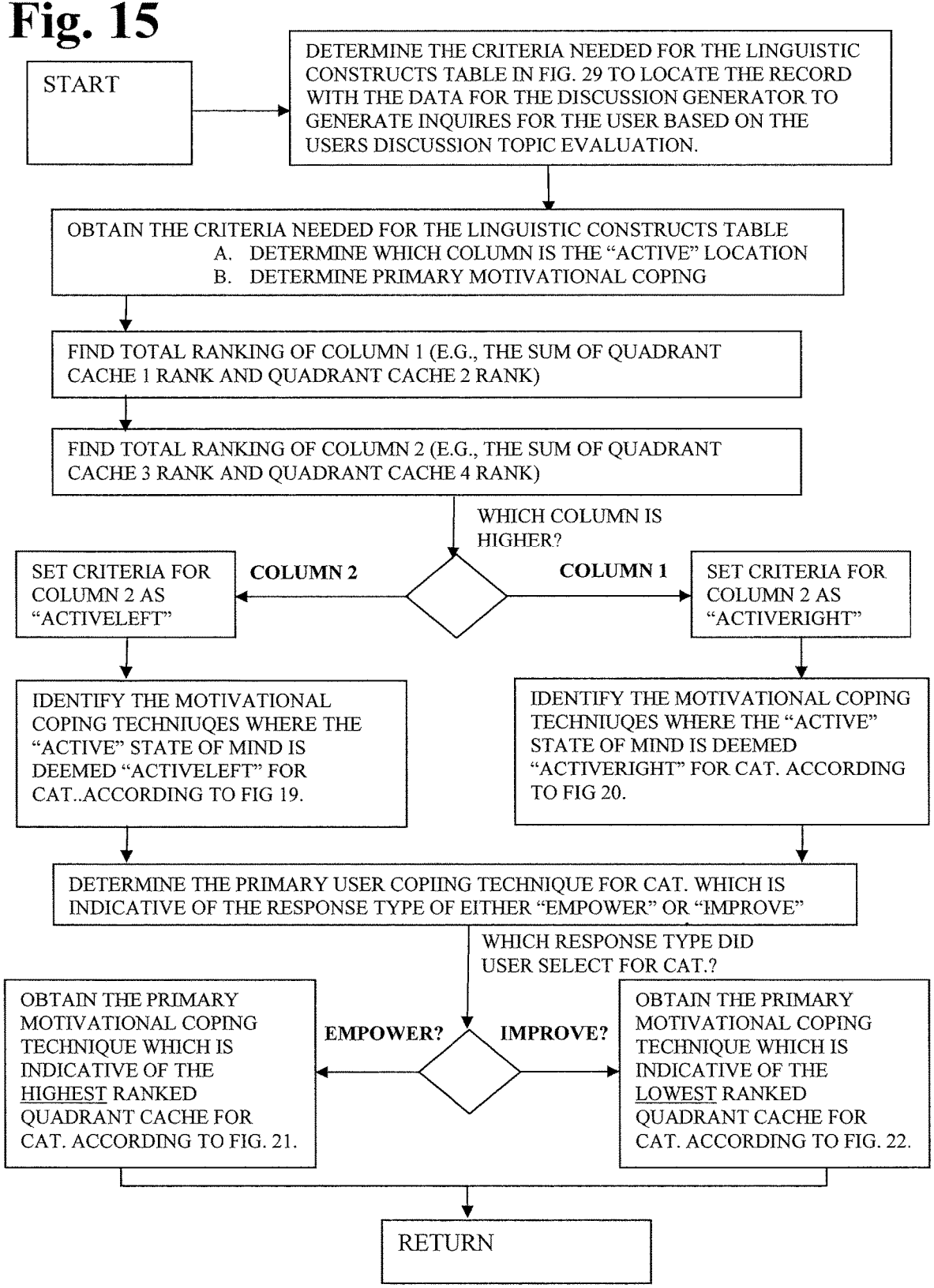
FIG. 15 shows a flowchart that represents the RESPONSE MANAGER 20 component in FIG. 4 in determining the criteria needed to locate the record in the Linguistic Constructs Table in FIG. 29 necessary for the INQUIRY BUILDER 18 component in FIG. 4 to build the inquiry to be generated back to the user through the DISCUSSION GENERATOR 5 component in FIG. 4. This criteria is based on the results of the response algorithm in FIG. 14 from the user's discussion topic evaluation.
Figure 16A:
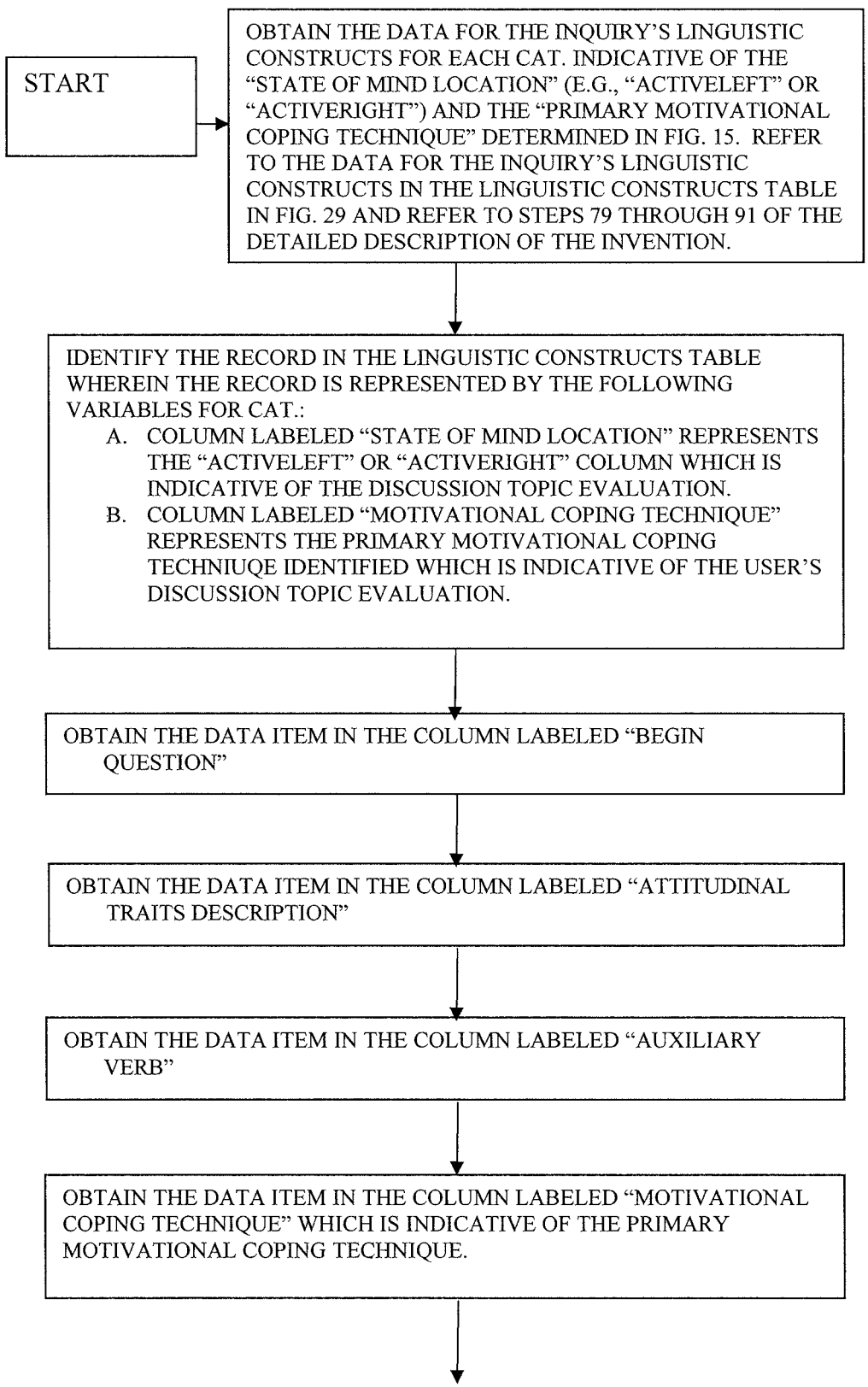
FIGS. 16A and 16B show a flowchart that represents the INQUIRY BUILDER 18 component in FIG. 4 in locating the data in the record from the Linguistic Constructs Table in FIG. 29 based on the criteria determined from FIG. 15.
Figure 16B:
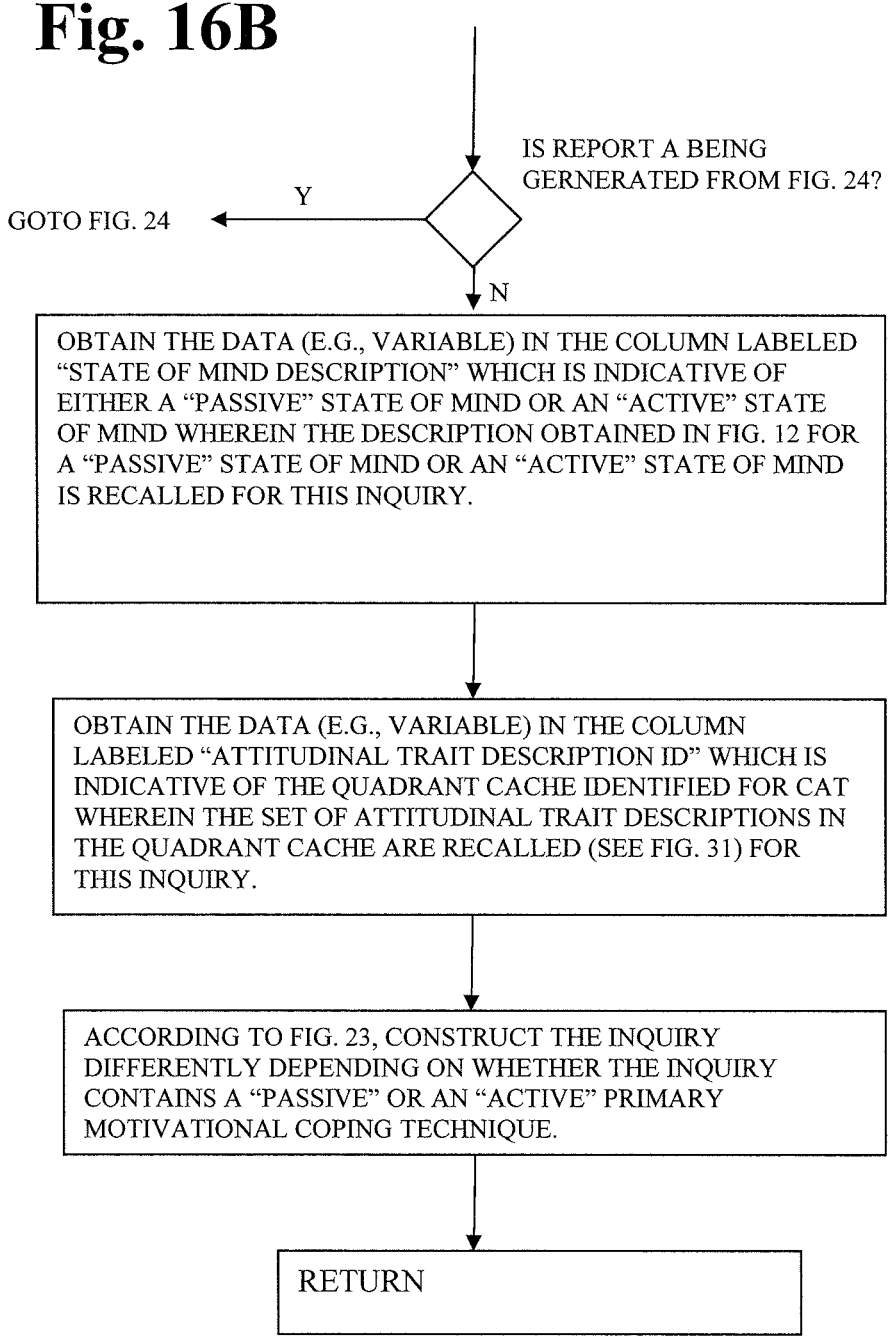
Figure 17:
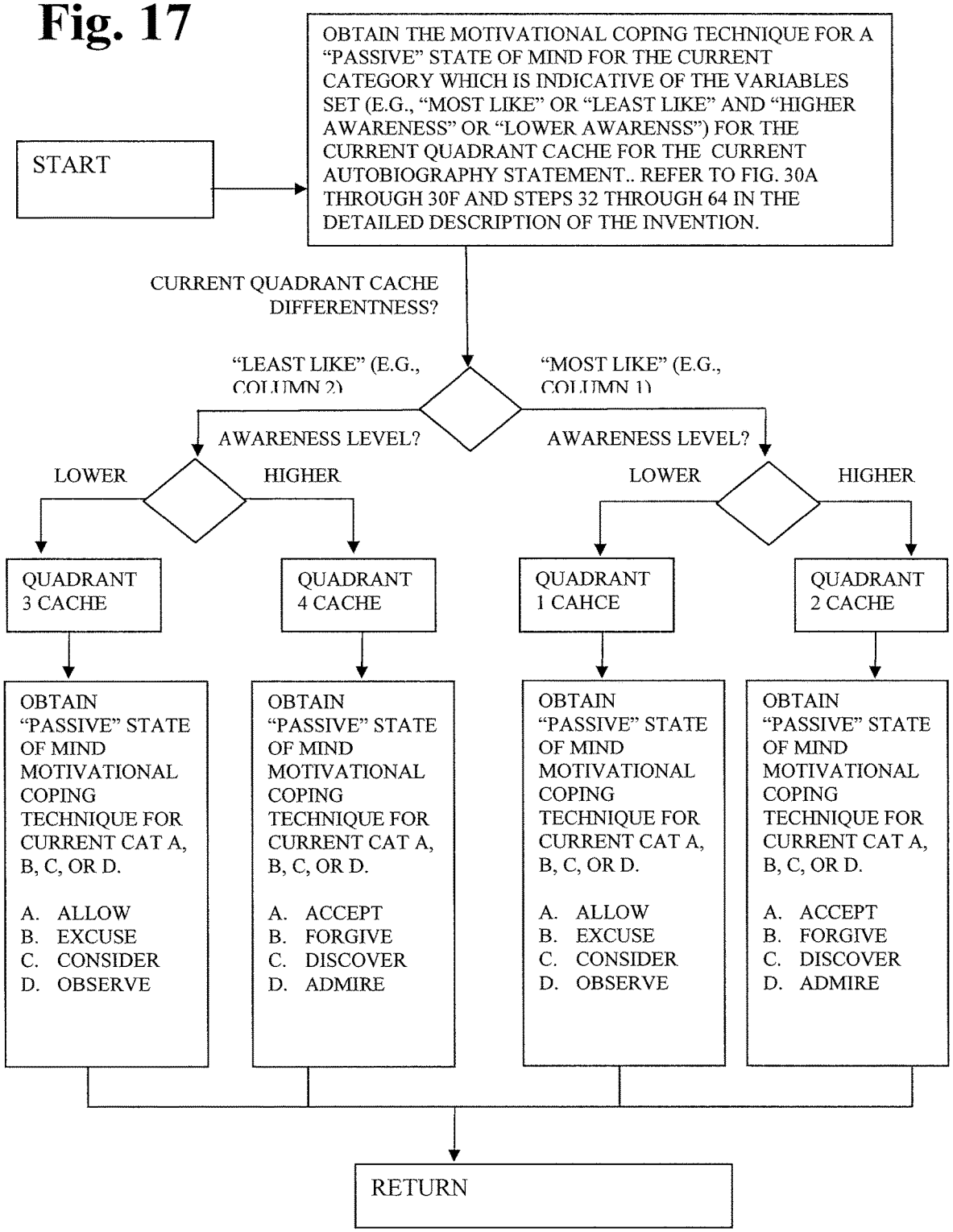
FIG. 17 shows a flowchart that represents the process for obtaining the "passive" (e.g., suggesting less effort) motivational coping technique necessary for developing the autobiography statement needed for a particular quadrant cache for each fundamental category (e.g., confidence) when the user's is developing their autobiography.
Figure 18:
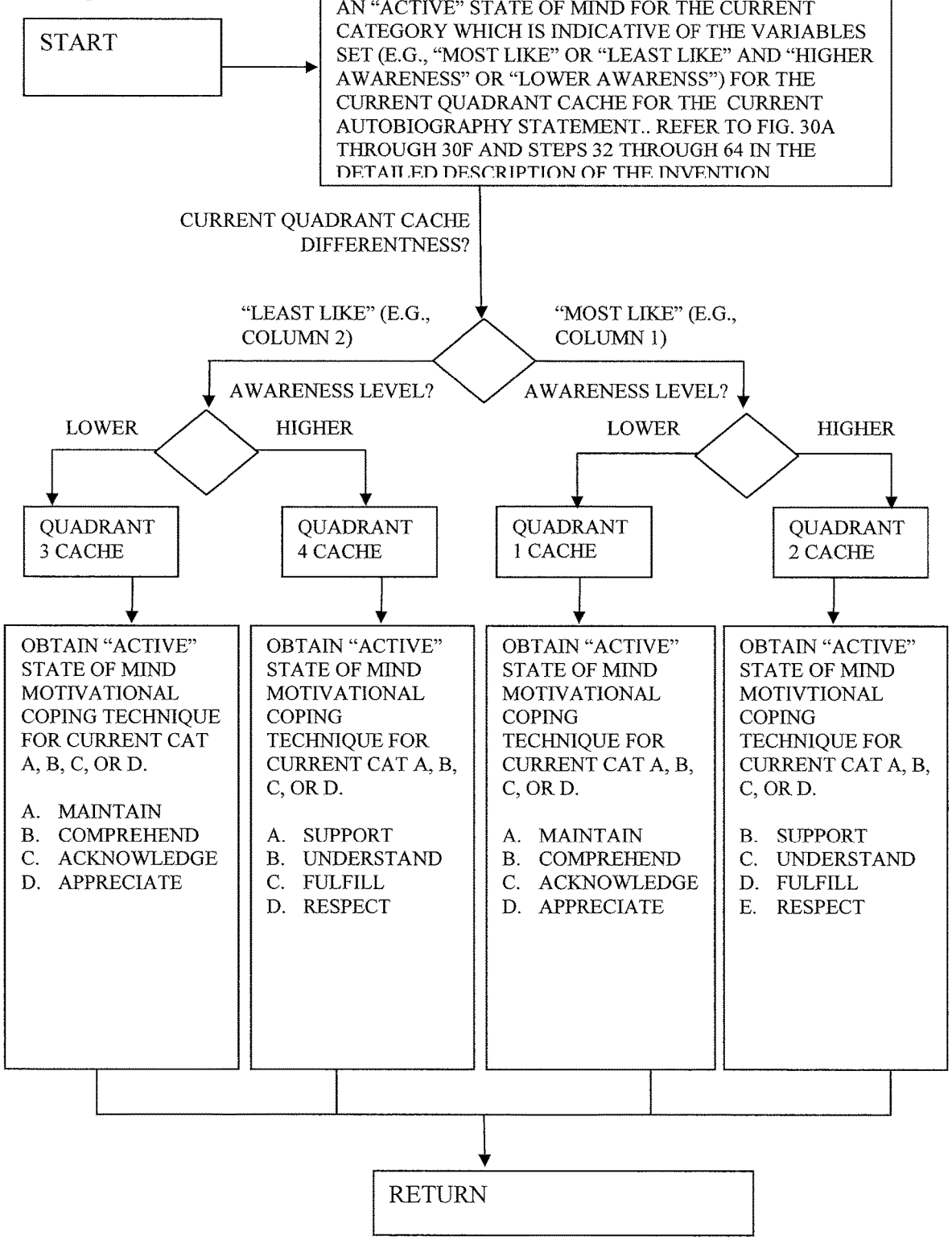
FIG. 18 shows a flowchart that represents the process for obtaining the "active" (e.g., suggesting more effort) motivational coping technique necessary for developing the autobiography statement needed for a particular quadrant cache for each fundamental category (e.g., confidence) when the user's is developing their autobiography.
Figure 19:
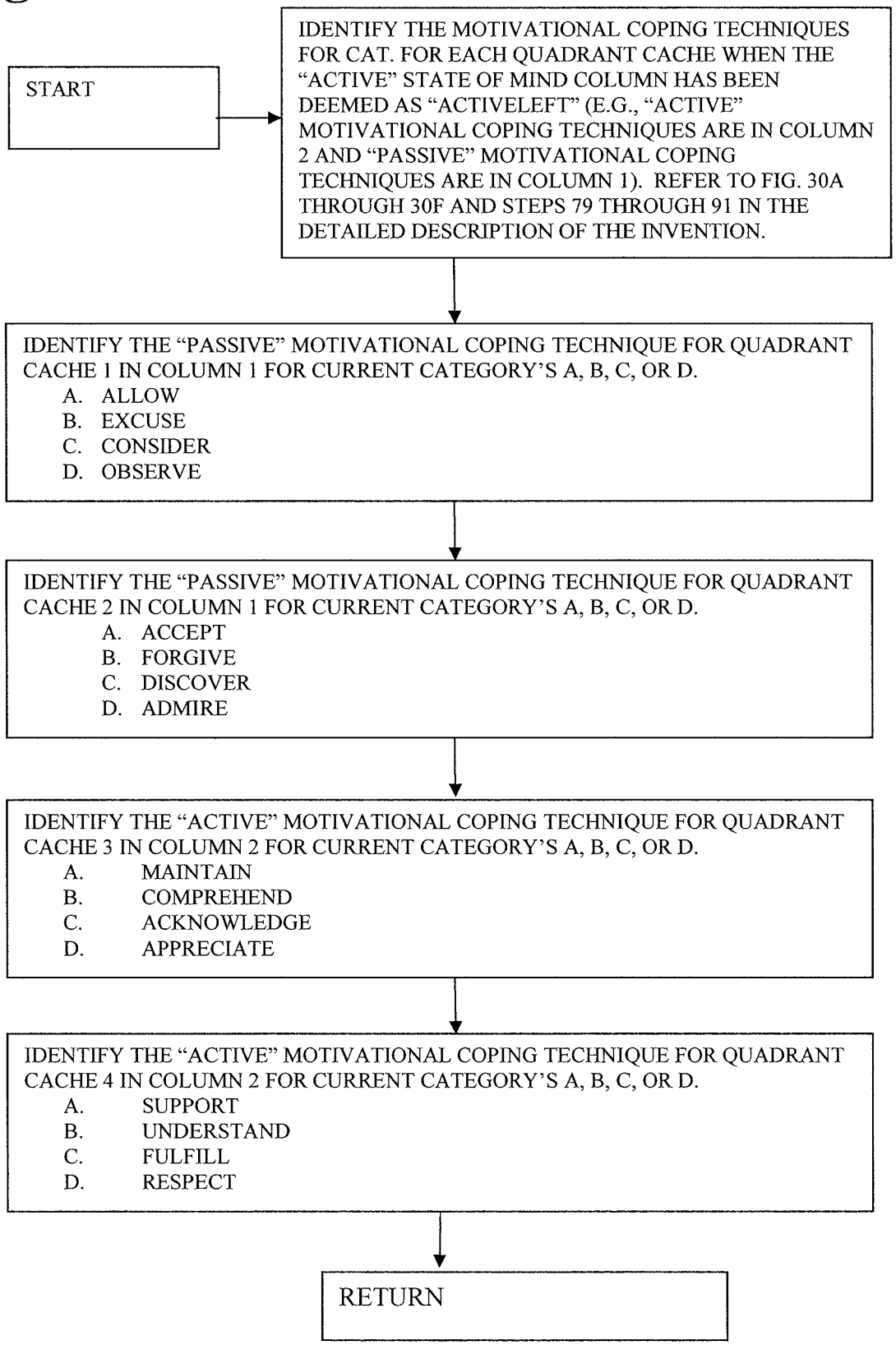
FIG. 19 shows a flowchart that represents the process for assigning the motivational coping techniques wherein the "active" motivational coping techniques occupy the "least like" quadrant caches and the "passive" motivational coping techniques occupy the "most like" quadrant caches (refer to FIG. 30a through FIG. 30f) as a result of the user's discussion topic evaluation.
Figure 20:
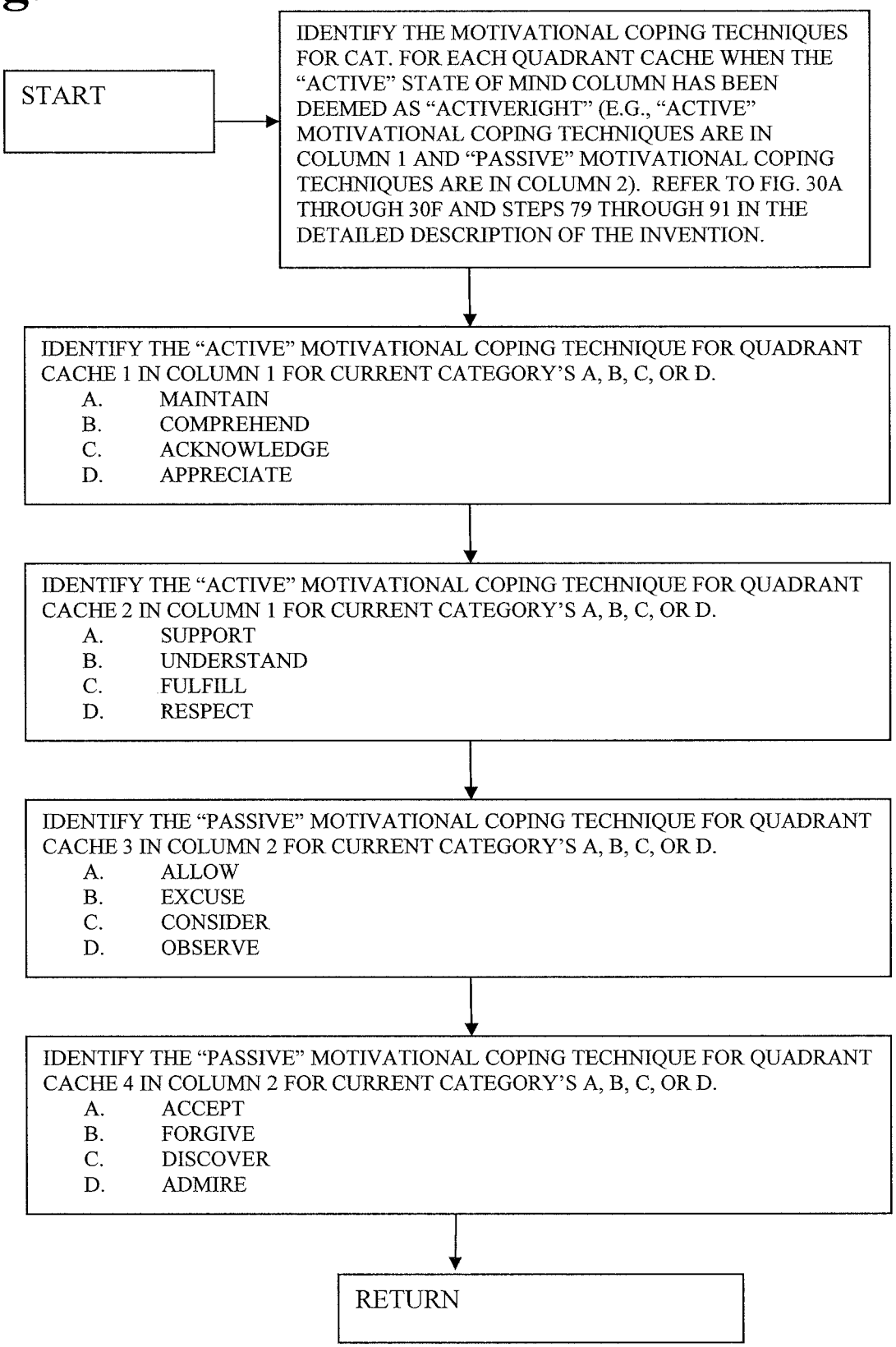
FIG. 20 shows a flowchart that represents the process for assigning the motivational coping techniques wherein the "passive" motivational coping techniques occupy the "least like" quadrant caches and the "active" motivational coping techniques occupy the "most like" quadrant caches (refer to FIG. 30a through FIG. 30f) as a result of the user's discussion topic evaluation.
Figure 21:
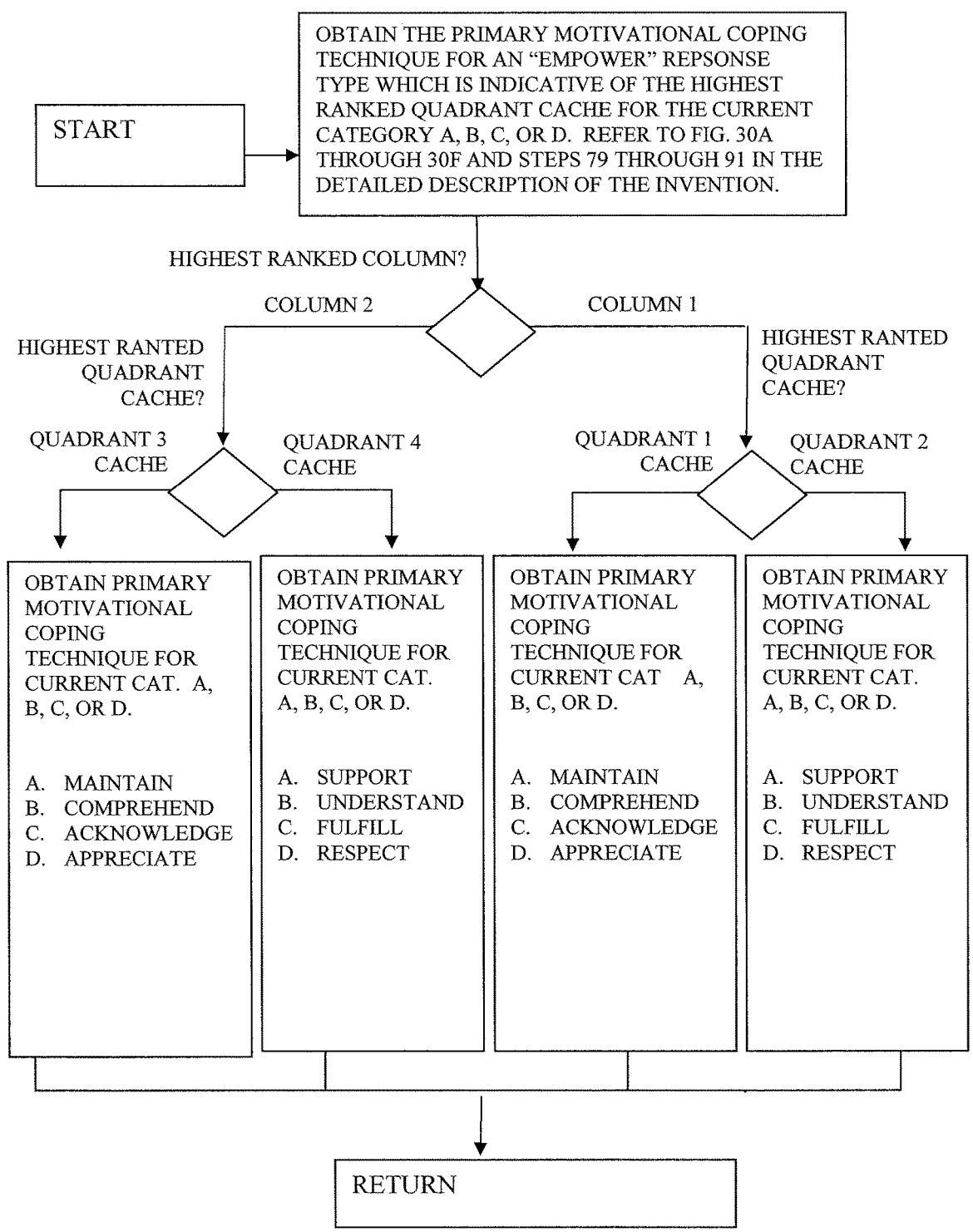
FIG. 21 shows a flowchart that represents the process for identifying the primary motivational coping technique for each fundamental category (e.g., confidence) when the user has requested an "empower" response type in a discussion topic evaluation.
Figure 22:
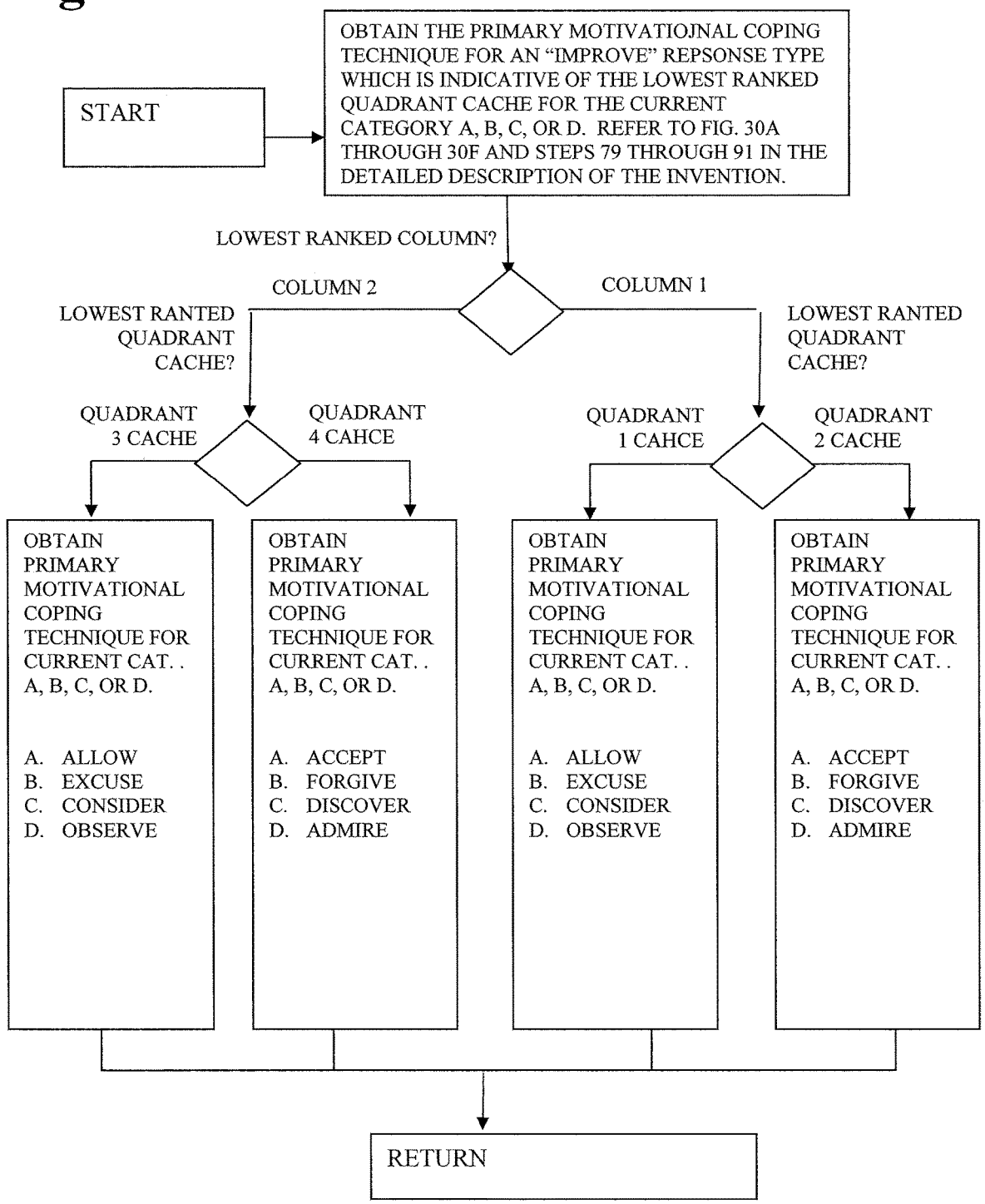
FIG. 22 shows a flowchart that represents the process for identifying the primary motivational coping technique for each fundamental category (e.g., confidence) when the user has requested an "improve" response type in a discussion topic evaluation.
Figure 23A:
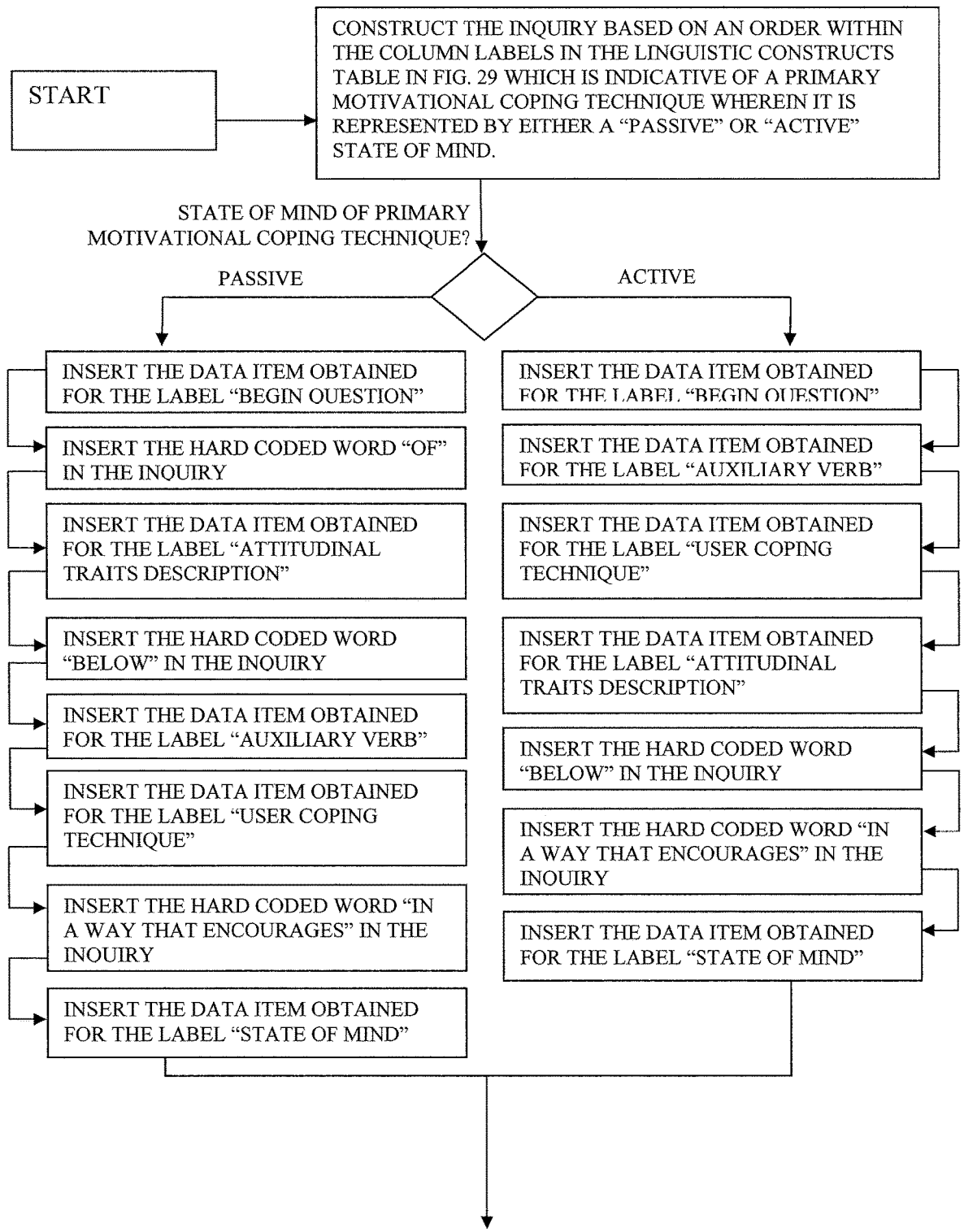
FIGS. 23A and 23B show a flowchart that represents the process for building the inquiry generated back to the user through the INQUIRY BUILDER 18 component in FIG. 4.
Figure 23B:
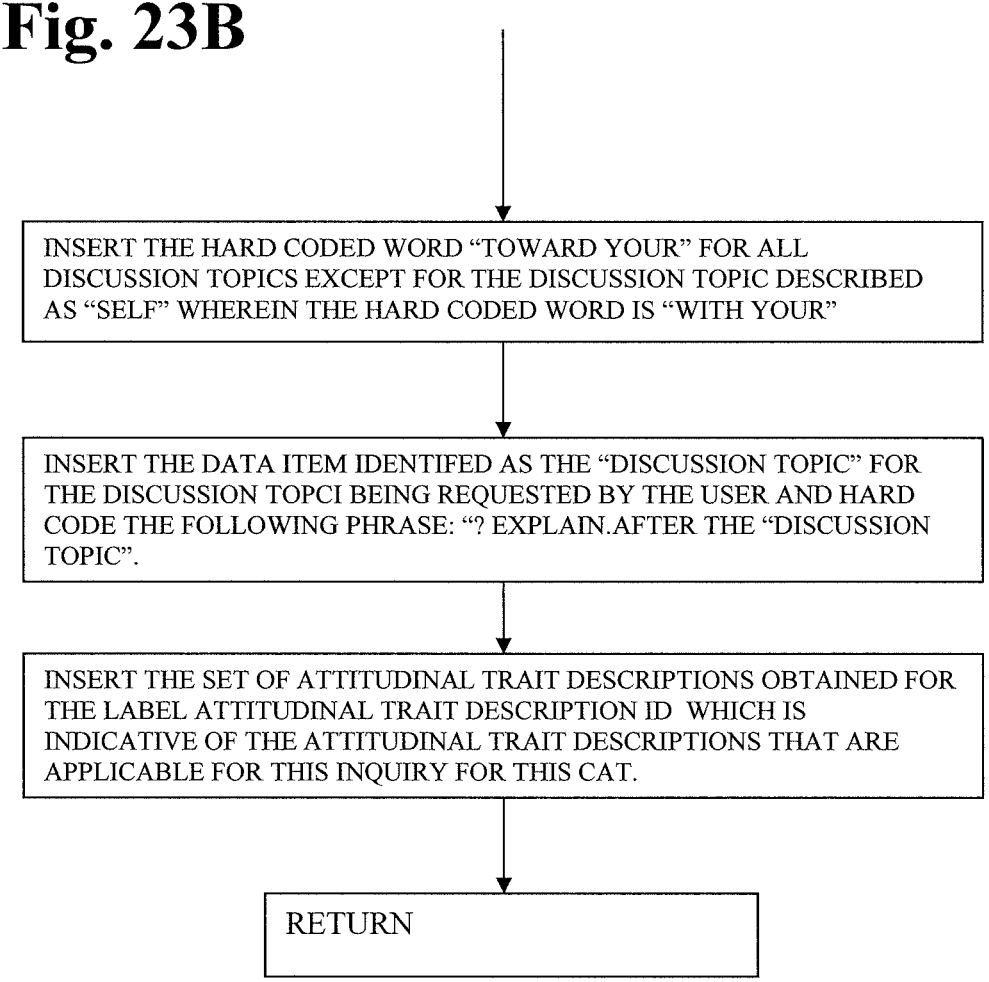
Figure 24A:
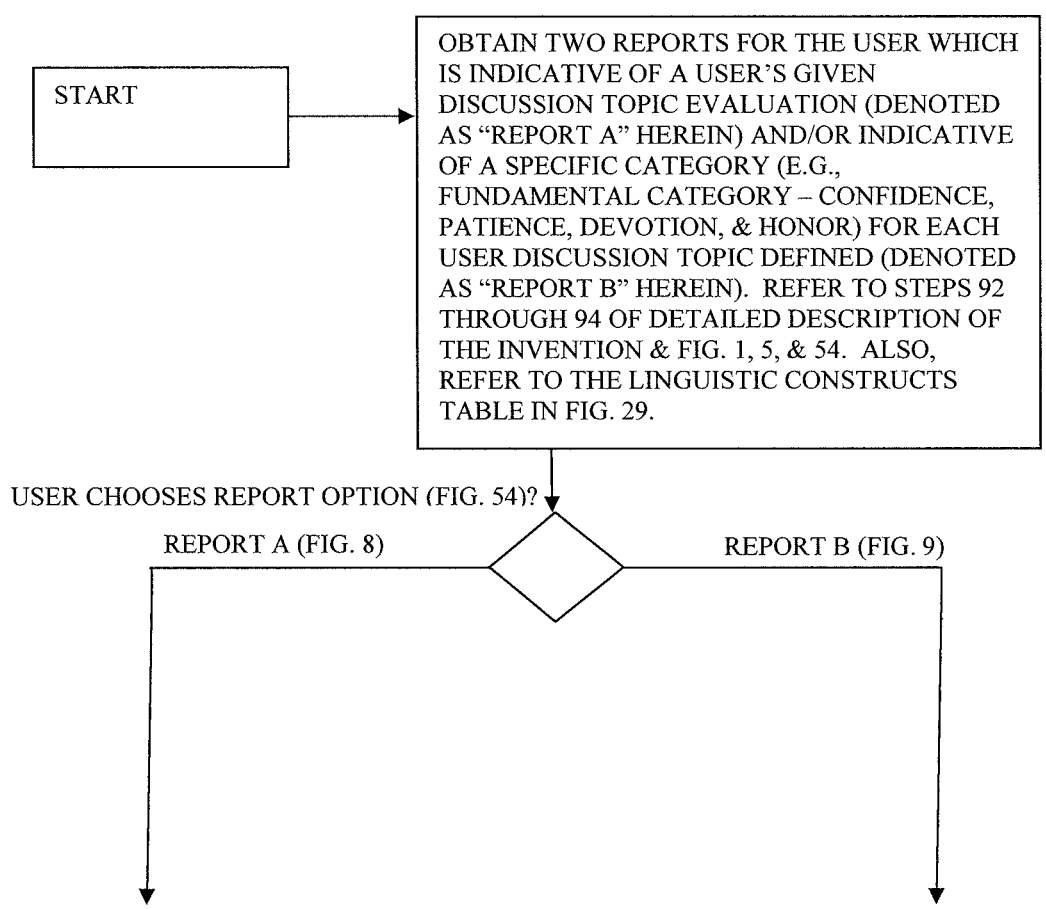
FIGS. 24A and 24B show a flowchart that represents the process for reporting journal entries by either showing the journal entry results of one discussion topic or by showing the journal entries for a specific fundamental category (e.g., confidence) in a specific date range of previously evaluated discussion topics.
Figure 24B:
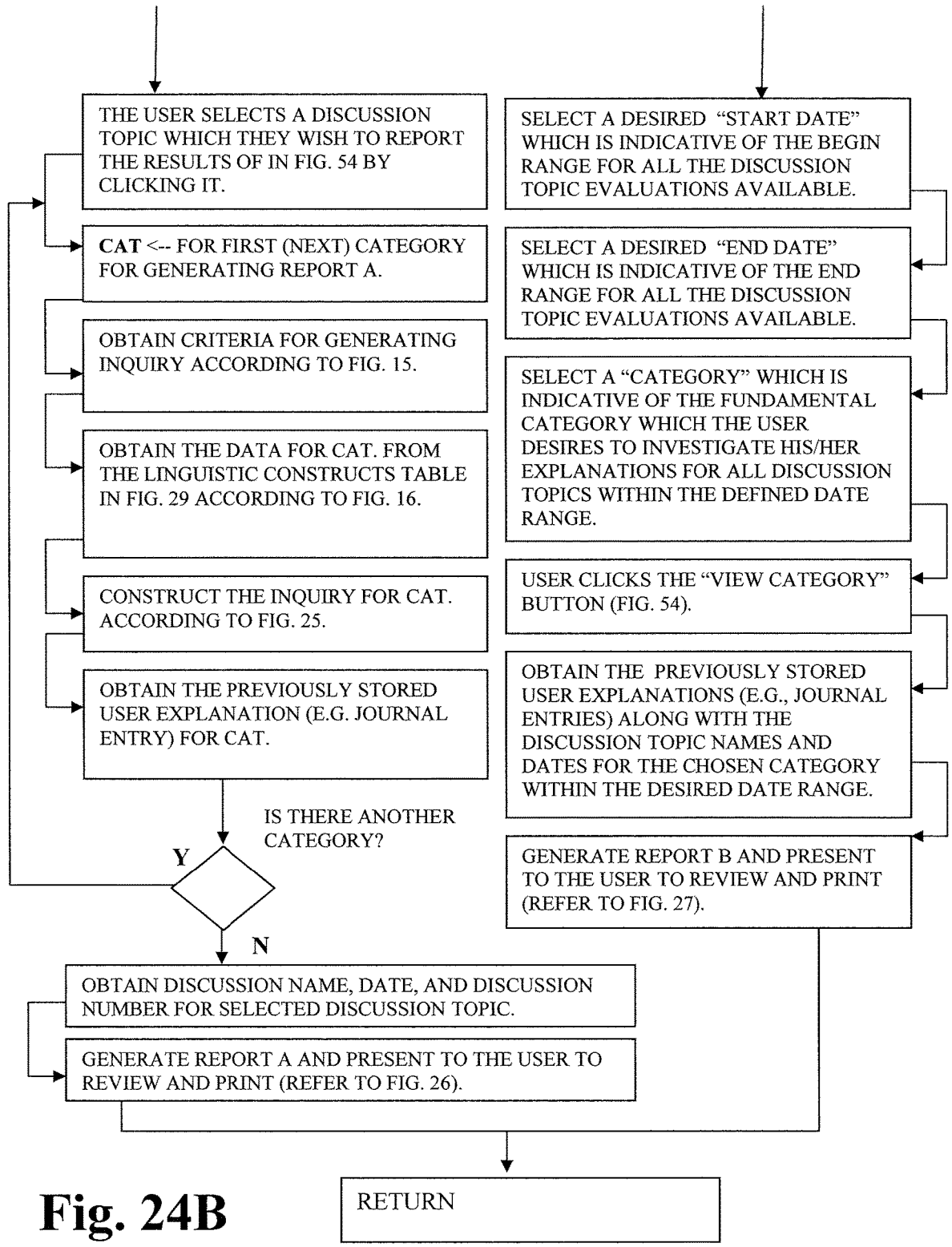
Figure 25:
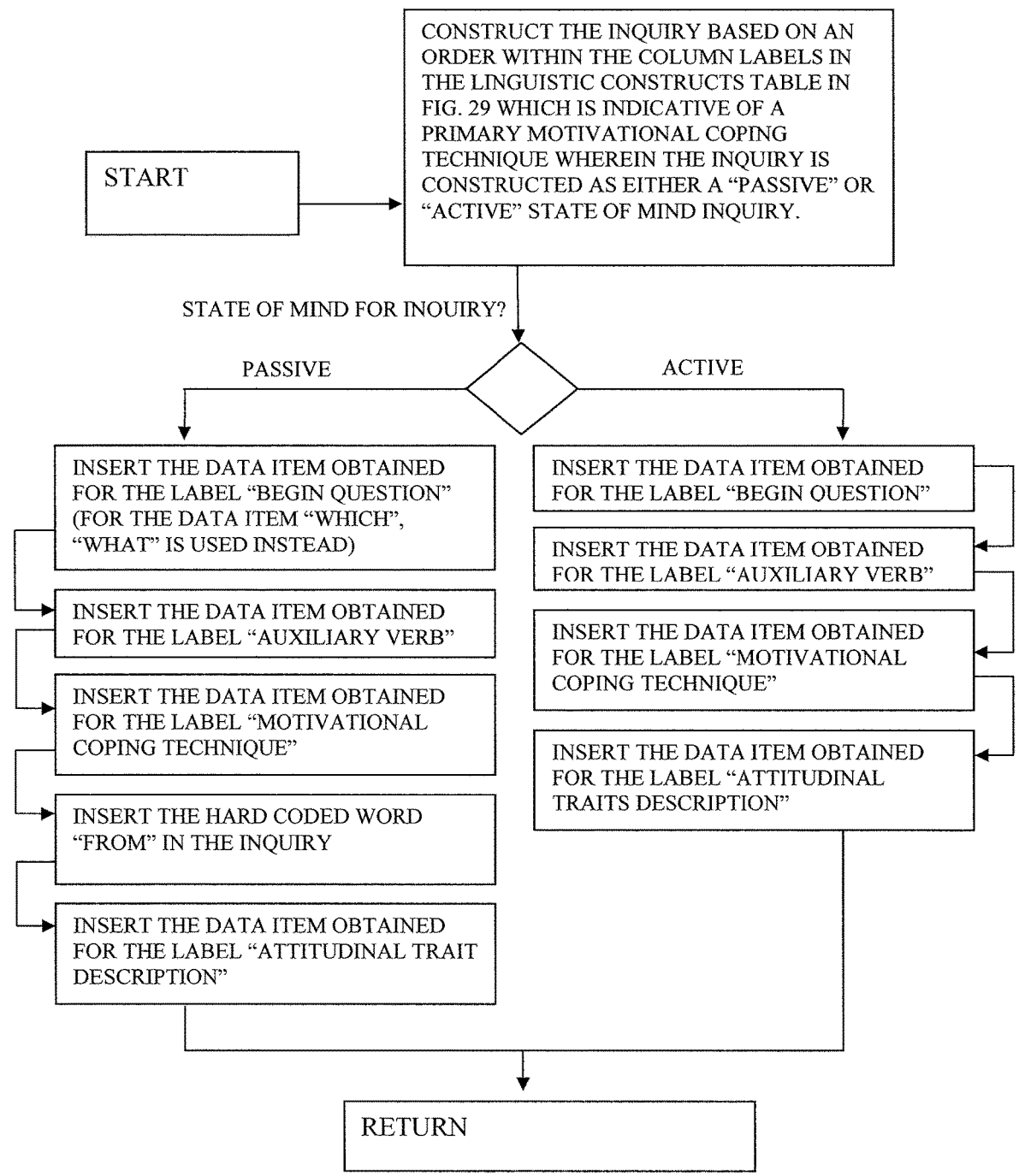
FIG. 25 shows a flowchart that represents the process for building questions that relate to the journal entries for the report showing the journal entry results of one discussion topic described in FIG. 24 above.

[71] Next, the user clicks the "SUBMIT" button in FIG. 48 to process the discussion topic evaluation which is stored for later use. However, before the evaluation is stored, a computational ranking algorithm called the response algorithm is performed which ranks (e.g., sub-ranks) each of the four quadrant caches for every fundamental category based on the user's discussion topic evaluation that are described in steps 69 through 72 above. This calculates how the user perceives the discussion topic being evaluated for each fundamental category. Refer to FIGS. 8 and 14.

[72] The response algorithm for fundamental category A (e.g., "confidence") will initially assign a sub-rank to either quadrant 1 cache or quadrant 2 cache (e.g., Column 1 representing the user's "most like" attitudinal trait descriptions) with the rank entered by the user (e.g., 7 in FIG. 48). By design, it is believed that the rank entered by the user reflects the user's understanding of his/her attitudes (e.g., "most like" attitudinal trait descriptions) as such attitudes relate to the discussion topic. In addition, since a "low" confidence level indicator is selected by the user, the user's rank of 7 (i.e., sub-rank) will be assigned to the lower awareness quadrant cache, or quadrant 1 cache in Column 1. Then the algorithm is designed to subtract 1 from 7 (7−1=6) and assigns a sub-rank of 6 to quadrant 2 cache, the upper quadrant cache in Column 1. Next, the response algorithm assigns sub-ranks to quadrant 3 cache and quadrant 4 cache (i.e., Column 2) called the "implied rank". The difference in the user's rank (e.g., 7) from the total possible rankings is 4 (e.g., 11−7=4) (e.g., 11 is used in one embodiment of this application because "11" encompasses all 10 possible ranks [e.g., 1 through 5 is the poor ranking range and 6 through 10 is the good ranking range] between 0 and 11; this logic eliminates the chance of the "highest" sub-rank being the same as the "lowest" sub rank which will confuse the discussion generator when generating either "empower" or "improve" inquires). Since a "low" confidence level indicator is selected by the user, the ranking of 4 is associated with quadrant 3 cache, the lower awareness quadrant cache. Next, the response algorithm is designed to subtract 1 from 4 (4−1=3) and assigns a sub-rank of 3 to quadrant 4 cache, the upper quadrant cache. Refer to FIGS. 8, 14, and 30*b*.

Figure 30A:
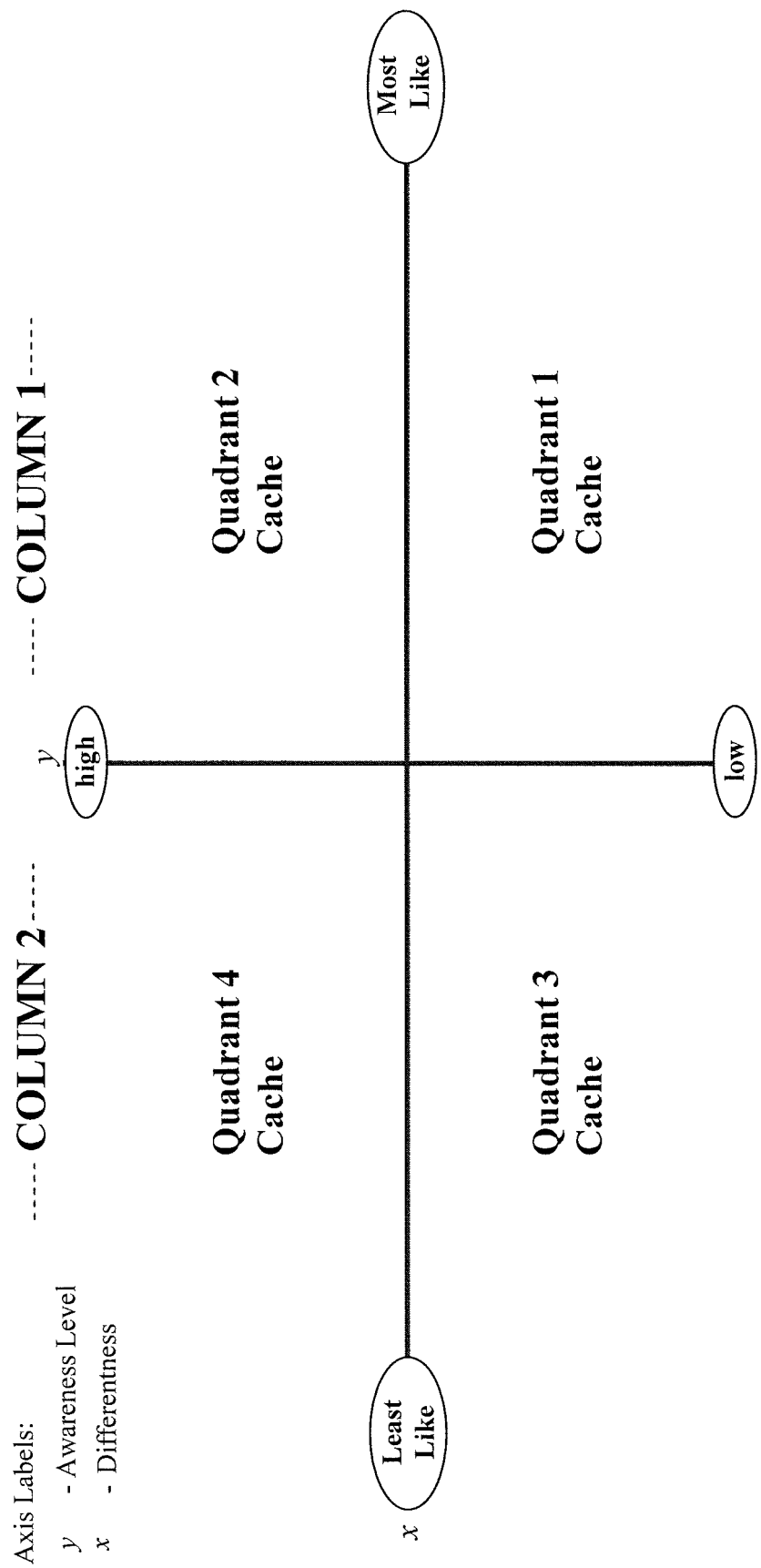
Figure 30C:
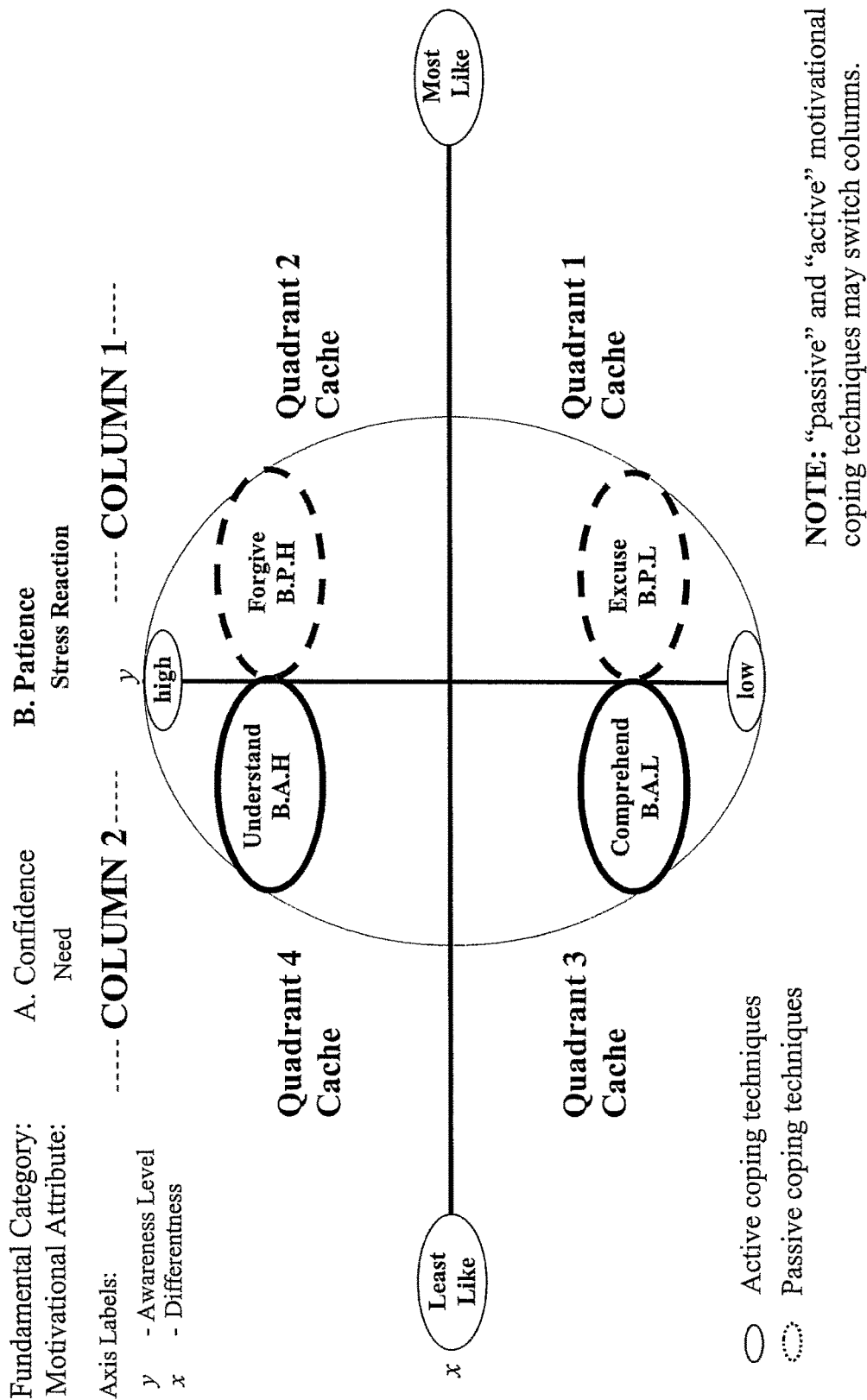

[73] The response algorithm for fundamental category B (e.g., "patience") will initially assign a sub-rank to either quadrant 1 cache or quadrant 2 cache (e.g., Column 1 representing the user's "most like" attitudinal trait descriptions) with the rank entered by the user (e.g., 4 in FIG. 48). By design, it is believed that the rank entered by the user reflects the user's understanding of his/her attitudes (e.g., "most like" or alternatively "least like" attitudinal trait descriptions) as such attitudes relate to the discussion topic. In addition, since a "high" confidence level indicator is selected by the user then the user's rank of 4 (i.e., sub-rank) will be assigned to the higher awareness quadrant cache, or quadrant 2 cache in Column 1. Then the algorithm is designed to subtract 1 from 4 (4−1=3) and assigns a sub-rank of 3 to quadrant 1 cache, the lower quadrant cache in Column 1. Next, the response algorithm assigns sub-ranks to quadrant 3 cache and quadrant 4 cache (i.e., Column 2) called the "implied rank". The difference in the user's rank (e.g., 4) from the total possible rankings is 7 (e.g., 11−4=7) (e.g., 11 is used in one embodiment of this application because "11" encompasses all 10 possible ranks [e.g., 1 through 5 is the poor ranking range and 6 through 10 is the good ranking range] between 0 and 11; this logic eliminates the chance of the "highest" sub-rank being the same as the "lowest" sub rank which will confuse the discussion generator when generating either "empower" or "improve" inquires). Since a "high" confidence level indicator is selected by the user then the ranking of 7 is associated with quadrant 4 cache, the higher awareness quadrant cache. Next, the response algorithm is designed to subtract 1 from 7 (7−1=6) and assigns a sub-rank of 6 to quadrant 3 cache, the lower quadrant cache. Refer to FIGS. 8, 14, and 30*c*.

[74] The response algorithm for fundamental category C (e.g., "devotion") will initially assign a sub-rank to either quadrant 1 cache or quadrant 2 cache (e.g., Column 1 representing the user's "most like" attitudinal trait descriptions) with the rank entered by the user (e.g., 8 in FIG. 48). By design, it is believed that the rank entered by the user reflects the user's understanding of his/her attitudes (e.g., "most like" or alternatively "least like" attitudinal trait descriptions) as such attitudes relate to the discussion topic. In addition, since a "high" confidence level indicator is selected by the user then the user's rank of 8 (i.e., sub-rank) will be assigned to the higher awareness quadrant cache, or quadrant 2 cache in Column 1. Then the algorithm is designed to subtract 1 from 8 (8−1=7) and assigns a sub-rank of 7 to quadrant 1 cache, the lower quadrant cache in Column 1. Next, the response algorithm assigns sub-ranks to quadrant 3 cache and quadrant 4 cache (i.e., Column 2) called the "implied rank". The difference in the user's rank (e.g., 8) from the total possible rankings is 3 (e.g., 11−8=3) (e.g., 11 is used in one embodiment of this application because "11" encompasses all 10 possible ranks [e.g., 1 through 5 is the poor ranking range and 6 through 10 is the good ranking range] between 0 and 11; this logic eliminates the chance of the "highest" sub-rank being the same as the "lowest" sub rank which will confuse the discussion generator when generating either "empower" or "improve" inquires). Since a "high" confidence level indicator is selected by the user then the ranking of 3 is associated with quadrant 4 cache, the higher awareness quadrant cache. Next, the response algorithm is designed to subtract 1 from 3 (3−1=2) and assigns a sub-rank of 2 to quadrant 3 cache, the lower quadrant cache. Refer to FIGS. 8, 14, and 30*d*.

Figure 30E:
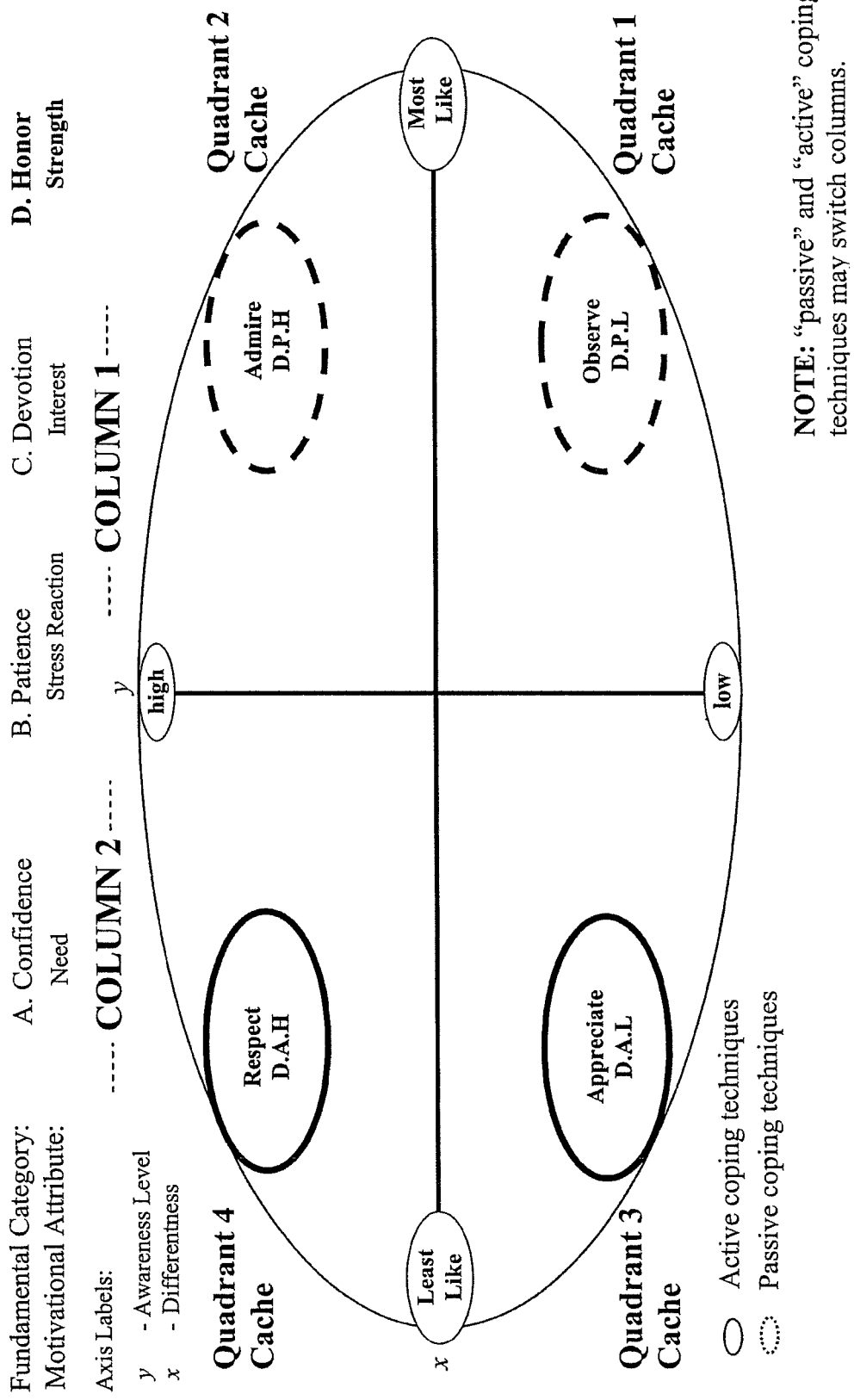
Figure 30F:
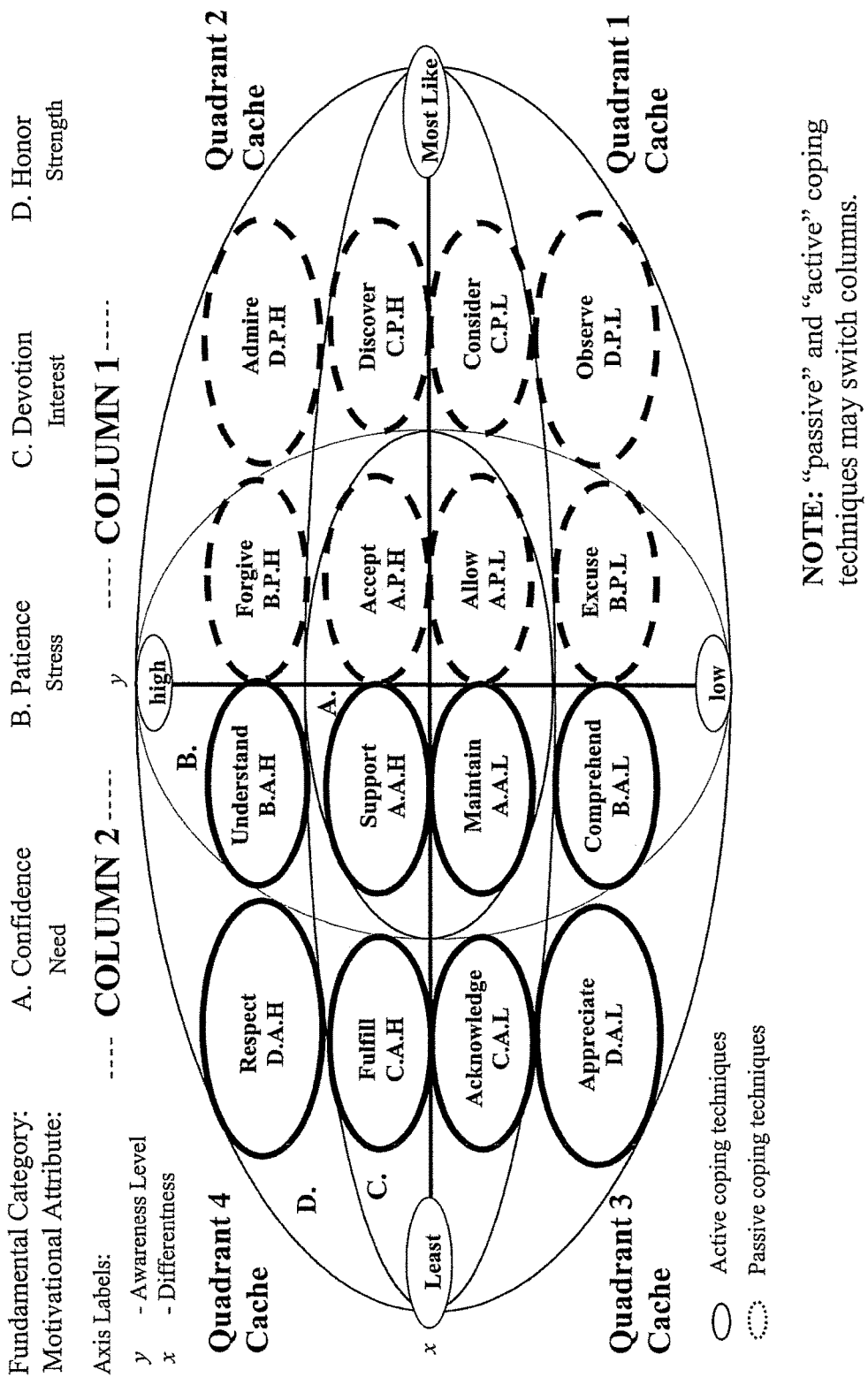
Figure 32:
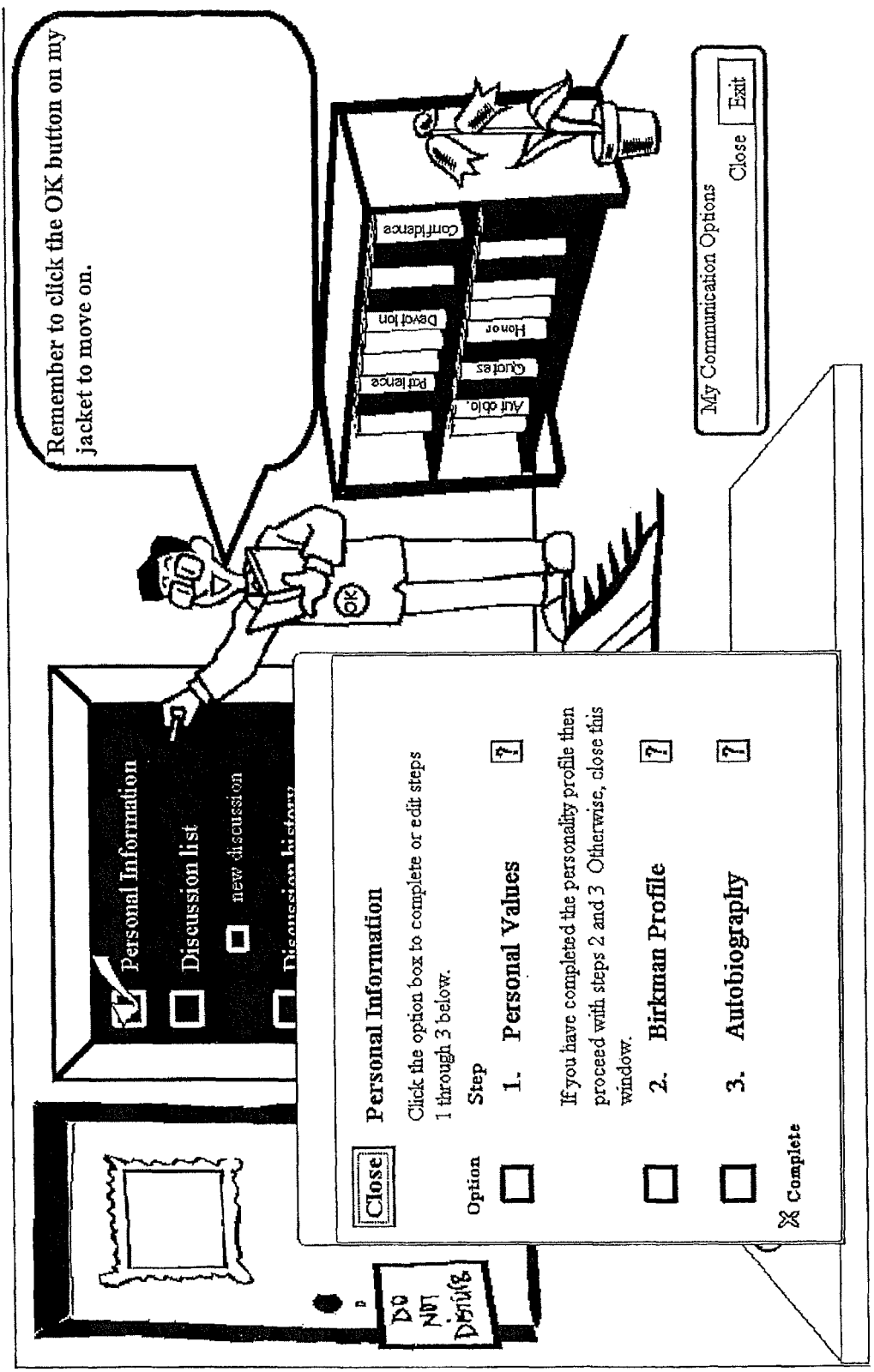
FIG. 32 shows a user interface to set up a user's personal information which includes defining personal values (e.g., state of mind descriptions), entering their user profile information (e.g., defining their sets of attitudinal trait descriptions based on the results of the Birkman Method), and developing their autobiography.

[75] The response algorithm for fundamental category D (e.g., "honor") will initially assign a sub-rank to either quadrant 1 cache or quadrant 2 cache (e.g., Column 1 representing the user's "most like" attitudinal trait descriptions) with the rank entered by the user (e.g., 5 in FIG. 48). By design, it is believed that the rank entered by the user reflects the user's understanding of his/her attitudes (e.g., "most like" or alternatively "least like" attitudinal trait descriptions) as such attitudes relate to the discussion topic. In addition, since a "low" confidence level indicator is selected by the user then the user's rank of 5 (i.e., sub-rank) will be assigned to the lower awareness quadrant cache, or quadrant 1 cache in Column 1. Then the algorithm is designed to subtract 1 from 5 (5−1=4) and assigns a sub-rank of 4 to quadrant 2 cache, the upper quadrant cache in Column 1. Next, the response algorithm assigns sub-ranks to quadrant 3 cache and quadrant 4 cache (i.e., Column 2) called the "implied rank". The difference in the user's rank (e.g., 5) from the total possible rankings is 6 (e.g., 11−5=6) (e.g., 11 is used in one embodiment of this application because "11" encompasses all 10 possible ranks [e.g., 1 through 5 is the poor ranking range and 6 through 10 is the good ranking range] between 0 and 11; this logic eliminates the chance of the "highest" sub-rank being the same as the "lowest" sub rank which will confuse the discussion generator when generating either "empower" or "improve" inquires). Since a "low" confidence level indicator is selected by the user then the ranking of 6 is associated with quadrant 3 cache, the lower awareness quadrant cache. Next, the response algorithm is designed to subtract 1 from 6 (6−1=5) and assigns a sub-rank of 5 to quadrant 4 cache, the upper quadrant cache. Refer to FIGS. 8, 14, and 30e.

[76] The results of the discussion topic evaluation derived from FIG. 48 are stored in a data structure. The user may evaluate and submit as many discussion topic evaluations as they like based on different discussion topics or the same discussion topic over many intervals of time. The result of a given discussion topic evaluation is dependent on how a user perceives the discussion topic at the time of evaluation.

Figure 49:
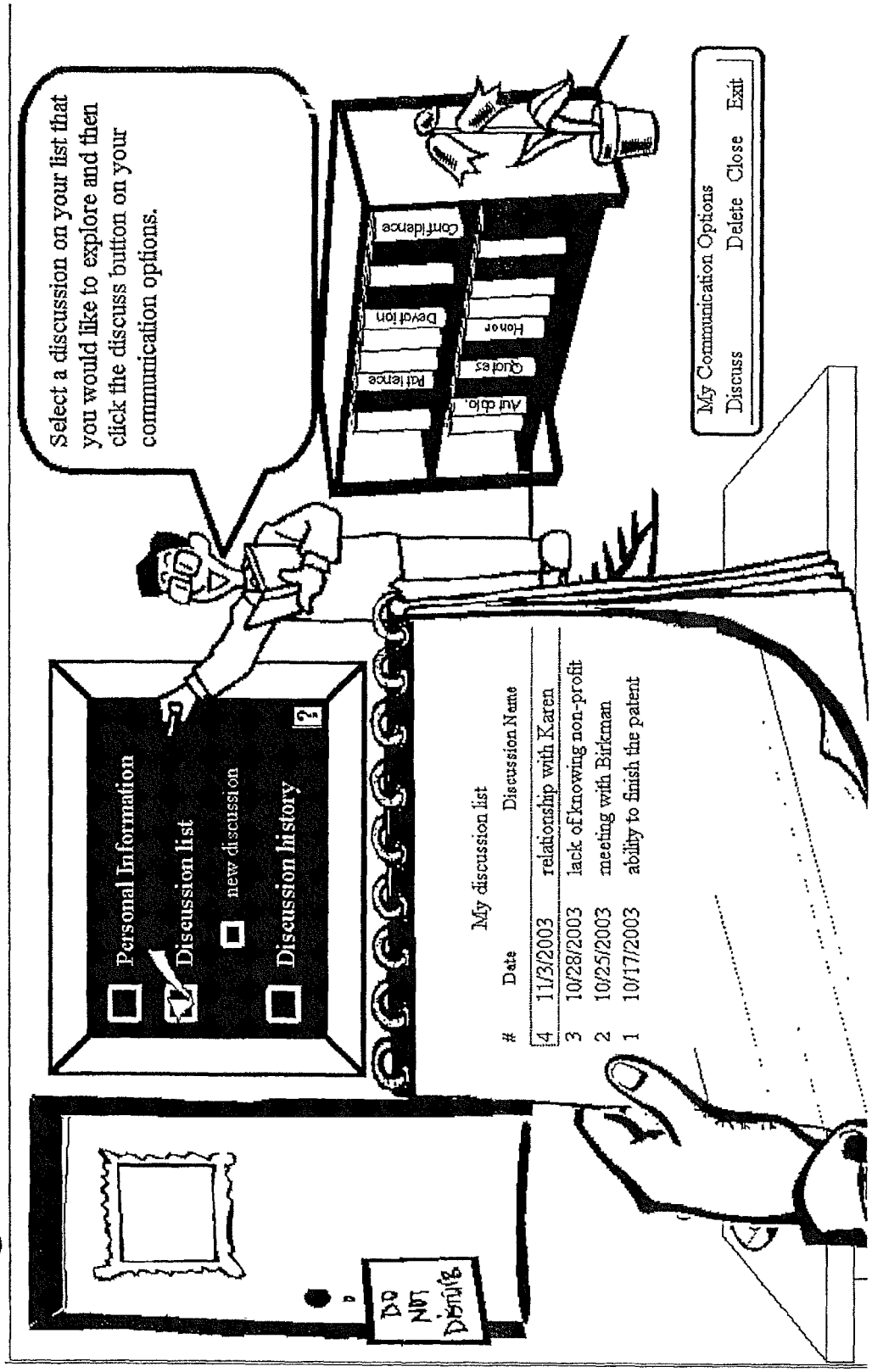
FIG. 49 shows a user interface wherein the user selects a previously defined and evaluated discussion topic from FIG. 48 in which the user wishes to investigate.

[77] The user chooses a discussion topic from the discussion topic list in FIG. 49. For this example, the user selects "relationship with Karen" and clicks the "discuss" button on the communication options panel in the lower right corner of FIG. 49. Next, a series of inquires (e.g., one for each fundamental category are generated by the discussion generator regarding the discussion topic. Each inquiry generated is based on how the discussion topic was ranked in steps 74 through 77 above. Refer to FIGS. 9, 15, 16, 19, 20, 21, 22, 23, 29, 30, and 31.

[78] For the fundamental category A (e.g., "confidence"), the RESPONSE MANAGER 20 component in FIG. 4 determines the primary motivational coping technique for the inquiry being generated. The inquiry's linguistic constructs or data assigned to this inquiry is based on the RESPONSE MANAGER 20 component in FIG. 4 determining two pieces of criteria which are: (i) the "active" state of mind column (e.g., either column 1 which is indicative of quadrant 1 cache and quadrant 2 cache, or column 2 which is indicative of quadrant 3 cache and quadrant 4 cache) and (ii) the primary motivational coping technique. To begin, the "passive" and "active" states of mind must be determined for each column in FIG. 30b. These states of mind are determined by adding the sub-ranks of the quadrant caches in column 1 and adding the sub-ranks of the quadrant caches in column 2 for the discussion topic "relationship with Karen". For fundamental category A in step 74, quadrant 1 cache is sub-ranked 7 and quadrant 2 cache is sub-ranked 6. Therefore, column 1 equals 13 (7+6=13). Quadrant 3 cache is sub-ranked 4 and quadrant 4 cache is sub-ranked 3. Therefore, column 2 equals 7 (4+3=7). The "active" state of mind will always exist in the column with the highest rank. As a result, column 1 (e.g., 13) will become the "active" state of mind, or "ActiveRight", and column 2 (e.g., 7) will become the "passive" state of mind (e.g., for this example, the "active" state of mind will exist in column 1 and the "passive" state of mind will exist in column 2 even though they are shown in FIG. 30b as opposite). Next, the motivational coping techniques are assigned to each quadrant cache. Therefore, since the "active" state of mind is defined as "ActiveRight", the motivational coping techniques will be labeled as follows: (A.P.L) Allow is assigned to quadrant 3 cache, (A.P.H) Accept is assigned to quadrant 4 cache, (A.A.L) Maintain is assigned to quadrant 1 cache, and (A.A.H) Support is assigned to quadrant 2 cache. As described in step 69, the user selected a response type of "improve". This means that the primary motivational coping technique chosen will be the lowest ranked quadrant cache. As a result, the primary motivational coping technique is in quadrant 4 cache (e.g., sub-ranked 3 in step 74), or (A.P.H) Accept. As a result, the RESPONSE MANAGER 20 component in FIG. 4 determines that the criteria for this inquiry is "ActiveRight" and "Accept". Refer to FIGS. 9, 15, 16, 19, 20, 21, 22, 23, 29, 30, and 31.

[79] The inquiry's linguistic constructs or data is built for the fundamental category A (i.e., "confidence") using the INQUIRY BUILDER 18 component in FIG. 4 using the Linguistic Constructs Table in FIG. 29 which is the table processed by the LINGUISTICS ORGANIZER 17 component in FIG. 4. First, the INQUIRY BUILDER 18 component in FIG. 4 locates the record necessary for assembling the inquiry by using the criteria (e.g., "ActiveRight" and "Accept") found in step 80 above. You'll notice that record #20 in the Linguistic Constructs Table in FIG. 29 is deemed "ActiveRight" under the column labeled state of mind location and "Accept" under the column labeled motivational coping technique. Therefore, the INQUIRY BUILDER 18 component in FIG. 4 determines that the data from record #20 will be used to assemble the inquiry for the fundamental category A inquiry. Finally, the inquiry may be built or assembled as follows. Starting with the begin question label or column of FIG. 29 and record #20, "Which" is identified as the data to start this inquiry (the word "which" corresponding to the passive state of mind as shown in FIG. 29). Next, within the motivational attribute description label, "others potentially important needs" is identified as the data used for the inquiry. Next, within the auxiliary verb label, "would you" is identified as the data used for this inquiry (the words "would you" corresponding to the passive state of mind and attitude trait descriptions "least like" the user or alternatively "will you" corresponds to attitudinal trait descriptions "most like" the user as shown in FIG. 29). Next, within the motivational coping technique label, "accept" is identified as the data used for this inquiry (corresponding to the primary motivational coping technique identified in step 80 above). Next, within the state of mind description label, "passive" is identified which is used to fetch the corresponding description defined in step 2 as the "passive" state of mind description (e.g., creativity, clarity, and satisfaction). Next, within the attitudinal trait description ID label, "A.2.4QCache4" is identified within the record. This identifies the user's "most like" or "least like" attitudinal trait descriptions used in the inquiry which can be found in FIG. 31 under the label A.2.4. As the result shown in FIG. 50, the PRESENTA- TION CONSTRUCTOR 21 component in FIG. 4 presents the inquiry as follows (note that words in single quotes are hard coded in the inquiry):

"Which 'of' others potentially important needs 'below' would you accept 'in a way that encourages' creativity, clarity, and satisfaction 'toward your' relationship with Karen? Explain."

an unemotional environment an environment based on trust issues reduced to their simplest form Refer to FIGS. 9, 15, 16, 19, 20, 21, 22, 23, 29, 30, and 31.

Figure 50:
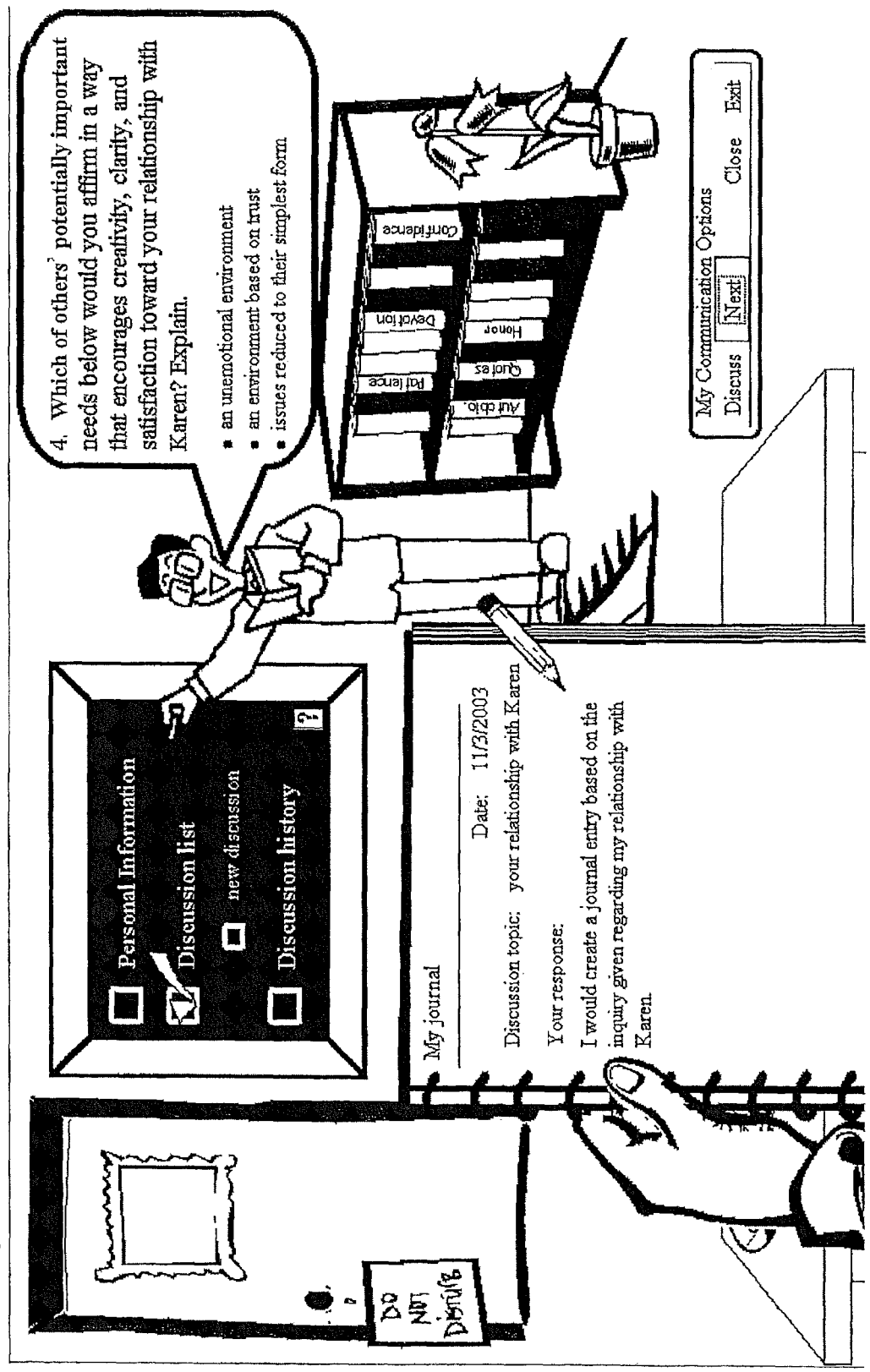
FIG. 50 shows a user interface wherein the user is presented with an inquiry for the fundamental category of "confidence" for the discussion topic selected from FIG. 49 above and wherein the user may enter a journal entry or answer to the inquiry in the electronic journal.

[80] The user enters an explanation in their electronic journal shown in FIG. 50 based on the inquiry described in step 81 above. This explanation is stored in a data structure for later reporting. Refer to FIGS. 9, 15, 16, 19, 20, 21, 22, 23, 29, 30, and 31.

[81] For the fundamental category B (e.g., "patience"), the RESPONSE MANAGER 20 component in FIG. 4 determines the primary motivational coping technique for the inquiry being generated. The inquiry's linguistic constructs or data assigned to this inquiry is based on the RESPONSE MANAGER 20 component in FIG. 4 determining two pieces of criteria which is (i) the "active" state of mind column (e.g., either column 1 which is indicative of quadrant 1 cache and quadrant 2 cache, or column 2 which is indicative of quadrant 3 cache and quadrant 4 cache) and (ii) the primary motivational coping technique. To begin, the "passive" and "active" states of mind must be determined for each column in FIG. 30c. These states of mind are determined by adding the sub-ranks of the quadrant caches in column 1 and adding the sub-ranks of the quadrant caches in column 2 for the discussion topic "relationship with Karen". For fundamental category B in step 75, quadrant 1 cache is sub-ranked 3 and quadrant 2 cache is sub-ranked 4. Therefore, column 1 equals 7 (3+4=7). Quadrant 3 cache is sub-ranked 6 and quadrant 4 cache is sub-ranked 7. Therefore, column 2 equals 7 (6+7=13). The "active" state of mind will always exist in the column with the highest rank. As a result, column 2 (e.g., 13) will become the "active" state of mind, or "ActiveLeft", and column 1 (e.g., 7) will become the "passive" state of mind (e.g., for this example, the "active" state of mind will exist in column 2 and the "passive" state of mind will exist in column 1 just as shown in FIG. 30c). Next, the motivational coping techniques are assigned to each quadrant cache. Therefore, since the "active" state of mind is defined as "ActiveLeft", the motivational coping techniques will be labeled as follows: (B.A.L) Comprehend is assigned to quadrant 3 cache, (B.A.H) Understand is assigned to quadrant 4 cache, (B.P.L) Excuse is assigned to quadrant 1 cache, and (B.P.H) Forgive is assigned to quadrant 2 cache. As described in step 70, the user selected a response type of "empower". This means that the primary motivational coping technique chosen will be the highest ranked quadrant cache. As a result, the primary motivational coping technique is in quadrant 4 cache (e.g., sub-ranked 7 in step 75), or (B.A.H) Understand. As a result, the RESPONSE MANAGER 20 component in FIG. 4 determines that the criteria for this inquiry is "ActiveLeft" and "Understand". Refer to FIGS. 9, 15, 16, 19, 20, 21, 22, 23, 29, 30, and 31.

[82] The inquiry's linguistic constructs or data is built for the fundamental category B (i.e., "patience") using the INQUIRY BUILDER 18 component in FIG. 4 using the Linguistic Constructs Table in FIG. 29 which is the table processed by the LINGUISTICS ORGANIZER 17 component in FIG. 4. First, the INQUIRY BUILDER 18 component in FIG. 4 locates the record necessary for assembling the inquiry by using the criteria (e.g., "ActiveLeft" and "Understand") found in step 83 above. You'll notice that record #8 in the Linguistic Constructs Table in FIG. 29 is deemed "ActiveLeft" under the column labeled state of mind location and "Understand" under the column labeled motivational coping technique. Therefore, the INQUIRY BUILDER 18 component in FIG. 4 determines that the data from record #8 will be used to assemble the inquiry for the fundamental category B inquiry. Finally, the inquiry may be built or assembled as follows. Starting with the begin question label, "How" is identified as the data to start this inquiry (the word "How" corresponding to the active state of mind as shown in FIG. 29). Next, within the motivational attribute description label, "others potentially difficult stress reactions" is identified as the data used for the inquiry. Next, within the auxiliary verb label, "could you" is identified as the data used for this inquiry (the words "could you" corresponding to the active state of mind and attitude trait descriptions "least like" the user or alternatively "can you" corresponds to attitudinal trait descriptions "most like" the user as shown in FIG. 29). Next, within the motivational coping technique label, "understand" is identified as the data used for this inquiry (corresponding to the primary motivational coping technique identified in step 83 above). Next, within the state of mind description label, "active" is identified which is used to fetch the corresponding description defined in step 3 as the "active" state of mind description (e.g., freedom, vitality, and connecting). Next, within the attitudinal trait description ID label, "B.2.4QCache4" is identified within the record. This identifies the user's "most like" or "least like" attitudinal trait descriptions used in the inquiry which can be found in FIG. 31 under the label B.2.4. As the result shown in FIG. 51, the PRESENTATION CONSTRUCTOR 21 component in FIG. 4 presents the inquiry as follows (note that words in single quotes are hard coded in the inquiry):

"How could you understand others potentially difficult stress reactions 'below' 'in a way that encourages' freedom, vitality, and connecting 'toward your' relationship with Karen? Explain."

failing to accept necessary change being impulsive discomfort with unusual ideas Refer to FIGS. 9, 15, 16, 19, 20, 21, 22, 23, 29, 30, and 31.

Figure 51:
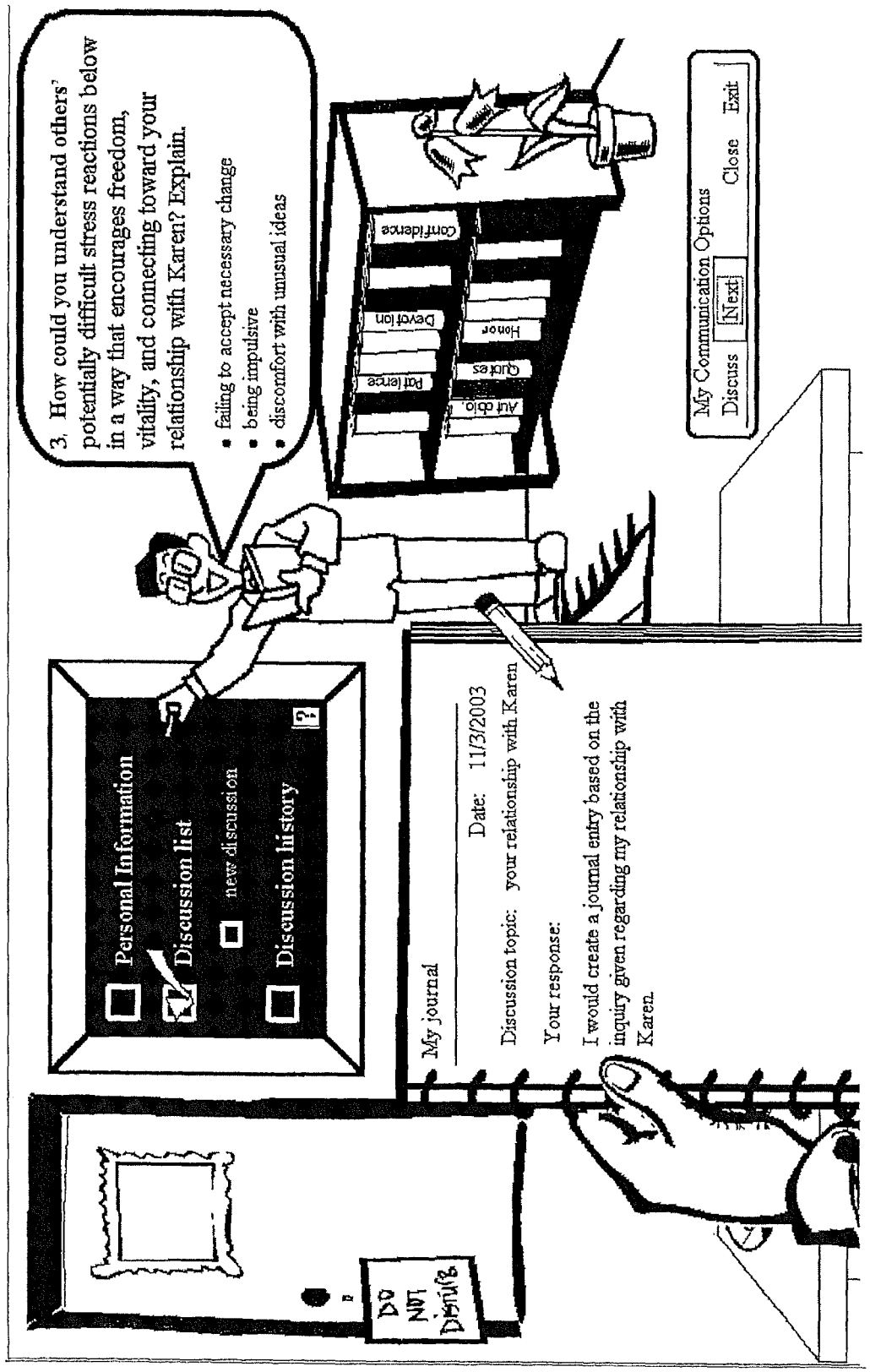
FIG. 51 shows a user interface wherein the user is presented with an inquiry for the fundamental category of "patience" for the discussion topic selected from FIG. 49 above and wherein the user may enter a journal entry or answer to the inquiry in the electronic journal.

[83] The user enters an explanation in their electronic journal shown in FIG. 51 based on the inquiry described in step 84 above. This explanation is stored in a data structure for later reporting. Refer to FIGS. 9, 15, 16, 19, 20, 21, 22, 23, 29, 30, and 31.

[84] For the fundamental category C (e.g., "devotion"), the RESPONSE MANAGER 20 component in FIG. 4 determines the primary motivational coping technique for the inquiry being generated. The inquiry's linguistic constructs or data assigned to this inquiry is based on the RESPONSE MANAGER 20 component in FIG. 4 determining two pieces of criteria which is (i) the "active" state of mind column (e.g., either column 1 which is indicative of quadrant 1 cache and quadrant 2 cache or column 2 which is indicative of quadrant 3 cache and quadrant 4 cache) and (ii) the primary motivational coping technique. To begin, the "passive" and "active" states of mind must be determined for each column in FIG. 30d. These states of mind are determined by adding the sub-ranks of the quadrant caches in column 1 and adding the sub-ranks of the quadrant caches in column 2 for the discussion topic "relationship with Karen". For fundamental category C in step 76, quadrant 1 cache is sub-ranked 7 and quadrant 2 cache is sub-ranked 8. Therefore, column 1 equals 15 (7+8=15). Quadrant 3 cache is sub-ranked 2 and quadrant 4 cache is sub-ranked 3. Therefore, column 2 equals 5 (2+3=5). The "active" state of mind will always exist in the column with the highest rank. As a result, column 1 (e.g., 15) will become the "active" state of mind, or "ActiveRight", and column 2 (e.g., 5) will become the "passive" state of mind (e.g., for this example, the "active" state of mind will exist in column 1 and the "passive" state of mind will exist in column 2 even though they are shown in FIG. 30d as opposite). Next, the motivational coping techniques are assigned to each quadrant cache. Therefore, since the "active" state of mind is defined as "ActiveRight", the motivational coping techniques will be labeled as follows: (C.P.L) Consider is assigned to quadrant 3 cache, (C.P.H) Discover is assigned to quadrant 4 cache, (C.A.L) Acknowledge is assigned to quadrant 1 cache, and (C.A.H) Fulfill is assigned to quadrant 2 cache. As described in step 71, the user selected a response type of "empower". This means that the primary motivational coping technique chosen will be the highest ranked quadrant cache. As a result, the primary motivational coping technique is in quadrant 2 cache (e.g., sub-ranked 8 in step 76), or (C.A.H) Fulfill. As a result, the RESPONSE MANAGER 20 component in FIG. 4 determines that the criteria for this inquiry is "ActiveRight" and "Fulfill". Refer to FIGS. 9, 15, 16, 19, 20, 21, 22, 23, 29, 30, and 31.

[85] The inquiry's linguistic constructs or data is built for the fundamental category C (i.e., "devotion") using the INQUIRY BUILDER 18 component in FIG. 4 using the Linguistic Constructs Table in FIG. 29 which is the table processed by the LINGUISTICS ORGANIZER 17 component in FIG. 4. First, the INQUIRY BUILDER 18 component in FIG. 4 locates the record necessary for assembling the inquiry by using the criteria (e.g., "ActiveRight" and "Fulfill") found in step 86 above. You'll notice that record #26 in the Linguistic Constructs Table in FIG. 29 is deemed "ActiveRight" under the column labeled state of mind location and "Fulfill" under the column labeled motivational coping technique. Therefore, the INQUIRY BUILDER 18 component in FIG. 4 determines that the data from record #26 will be used to assemble the inquiry for the fundamental category C inquiry. Finally, the inquiry may be built or assembled as follows. Starting with the begin question label, "How" is identified as the data to start this inquiry (the word "How" corresponding to the active state of mind as shown in FIG. 29). Next, within the motivational attribute description label, "others potentially difficult stress reactions" is identified as the data used for the inquiry. Next, within the auxiliary verb label, "can you" is identified as the data used for this inquiry (the words "can you" corresponding to the active state of mind and attitude trait descriptions "most like" the user or alternatively "could you" corresponds to attitudinal trait descriptions "least like" the user as shown in FIG. 29). Next, within the motivational coping technique label, "fulfill" is identified as the data used for this inquiry (corresponding to the primary motivational coping technique identified in step 86 above). Next, within the state of mind description label, "active" is identified which is used to fetch the corresponding description defined in step 3 as the "active" state of mind description (e.g., freedom, vitality, and connecting). Next, within the attitudinal trait description ID label, "C.1.2QCache2" is identified within the record. This identifies the user's "most like" or "least like" attitudinal trait descriptions used in the inquiry which can be found in FIG. 31 under the label C.1.2. As the result shown in FIG. 52, the PRESENTATION CONSTRUCTOR 21 component in FIG. 4 presents the inquiry as follows (note that words in single quotes are hard coded in the inquiry):
"How can you fulfill your most passionate interests 'below' 'in a way that encourages' freedom, vitality, and connecting 'toward your' relationship with Karen? Explain."
educational approaches to development
comfort in problem solving and crisis intervention
managing through knowledge and expertise
Refer to FIGS. 9, 15, 16, 19, 20, 21, 22, 23, 29, 30, and 31.

Figure 52:
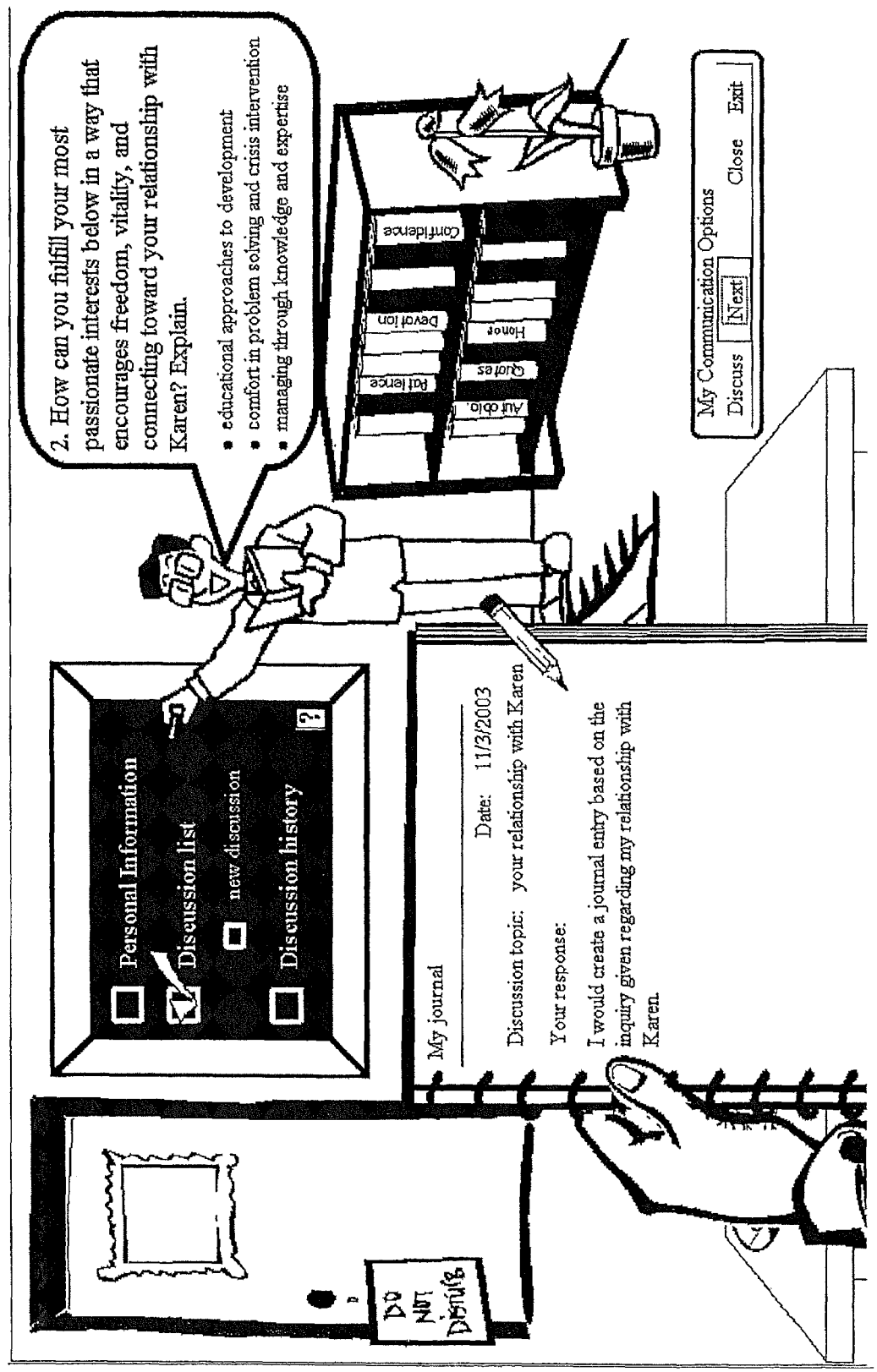
FIG. 52 shows a user interface wherein the user is presented with an inquiry for the fundamental category of "devotion" for the discussion topic selected from FIG. 49 above and wherein the user may enter a journal entry or answer to the inquiry in the electronic journal.

[86] The user enters an explanation in their electronic journal shown in FIG. 52 based on the inquiry described in step 87 above. This explanation is stored in a data structure for later reporting. Refer to FIGS. 9, 15, 16, 19, 20, 21, 22, 23, 29, 30, and 31.

[87] For the fundamental category D (e.g., "honor"), the RESPONSE MANAGER 20 component in FIG. 4 determines the primary motivational coping technique for the inquiry being generated. The inquiry's linguistic constructs or data assigned to this inquiry is based on the RESPONSE MANAGER 20 component in FIG. 4 determining two pieces of criteria which is (i) the "active" state of mind column (e.g., either column 1 which is indicative of quadrant 1 cache and quadrant 2 cache or column 2 which is indicative of quadrant 3 cache and quadrant 4 cache) and (ii) the primary motivational coping technique. To begin, the "passive" and "active" states of mind must be determined for each column in FIG. 30e. These states of mind are determined by adding the sub-ranks of the quadrant caches in column 1 and adding the sub-ranks of the quadrant caches in column 2 for the discussion topic "relationship with Karen". For fundamental category D in step 77, quadrant 1 cache is sub-ranked 5 and quadrant 2 cache is sub-ranked 4. Therefore, column 1 equals 9 (5+4=9). Quadrant 3 cache is sub-ranked 6 and quadrant 4 cache is sub-ranked 5. Therefore, column 2 equals 11 (6+5=11). The "active" state of mind will always exist in the column with the highest rank. As a result, column 2 (e.g., 11) will become the "active" state of mind, or "ActiveLeft", and column 2 (e.g., 9) will become the "passive" state of mind (e.g., for this example, the "active" state of mind will exist in column 2 and the "passive" state of mind will exist in column 1 just as shown in FIG. 30e). Next, the motivational coping techniques are assigned to each quadrant cache. Therefore, since the "active" state of mind is defined as "ActiveLeft", the motivational coping techniques will be labeled as follows: (D.A.L) Appreciate is assigned to quadrant 3 cache, (D.A.H) Respect is assigned to quadrant 4 cache, (D.P.L) Observe is assigned to quadrant 1 cache, and (D.P.H) Admire is assigned to quadrant 2 cache. As described in step 72, the user selected a response type of "empower". This means that the primary motivational coping technique chosen will be the highest ranked quadrant cache. As a result, the primary motivational coping technique is in quadrant 3 cache (e.g., sub-ranked 6 in step 77), or (D.A.L) Appreciate. As a result, the RESPONSE MANAGER 20 component in FIG. 4 determines that the criteria for this inquiry is "ActiveLeft" and "Appreciate". Refer to FIGS. 9, 15, 16, 19, 20, 21, 22, 23, 29, 30, and 31.

[88] The inquiry's linguistic constructs or data is built for the fundamental category D (i.e., "honor") using the INQUIRY BUILDER 18 component in FIG. 4 using the Linguistic Constructs Table in FIG. 29 which is the table processed by the LINGUISTICS ORGANIZER 17 component in FIG. 4. First, the INQUIRY BUILDER 18 component in FIG. 4 locates the record necessary for assembling the inquiry by using the criteria (e.g., "ActiveLeft" and "Appreciate") found in step 89 above. You'll notice that record #15 in the Linguistic Constructs Table in FIG. 29 is deemed "ActiveLeft" under the column labeled state of mind location and "Appreciate" under the column labeled motivational coping technique. Therefore, the INQUIRY BUILDER 18 component in FIG. 4 determines that the data from record #15 will be used to assemble the inquiry for the fundamental category D inquiry. Finally, the inquiry may be built or assembled as follows. Starting with the begin question label, "How" is identified as the data to start this inquiry (the word "How" corresponding to the active state of mind as shown in FIG. 29). Next, within the motivational attribute description label, "others potential strengths" is identified as the data used for the inquiry. Next, within the auxiliary verb label, "could you" is identified as the data used for this inquiry (the words "could you" corresponding to the active state of mind and attitude trait descriptions "least like" the user or alternatively "can you" corresponds to attitudinal trait descriptions "most like" the user as shown in FIG. 29). Next, within the motivational coping technique label, "appreciate" is identified as the data used for this inquiry (corresponding to the primary motivational coping technique identified in step 89 above). Next, within the state of mind description label, "active" is identified which is used to fetch the corresponding description defined in step 3 as the "active" state of mind description (e.g., freedom, vitality, and connecting). Next, within the attitudinal trait description ID label, "D.2.3QCache3" is identified within the record. This identifies the users "most like" or "least like" attitudinal trait descriptions used in the inquiry which can be found in FIG. 31 under the label D.2.3. As the result shown in FIG. 53, the PRESENTATION CONSTRUCTOR 21 component in FIG. 4 presents the inquiry as follows (note that words in single quotes are hard coded in the inquiry): "How can you appreciate others potential strengths 'below' 'in a way that encourages' freedom, vitality, and connecting 'toward your' relationship with Karen? Explain."
concentrates attention well
oriented toward individual advantage
able to work well alone Refer to FIGS. 9, 15, 16, 19, 20, 21, 22, 23, 29, 30, and 31.

Figure 53:
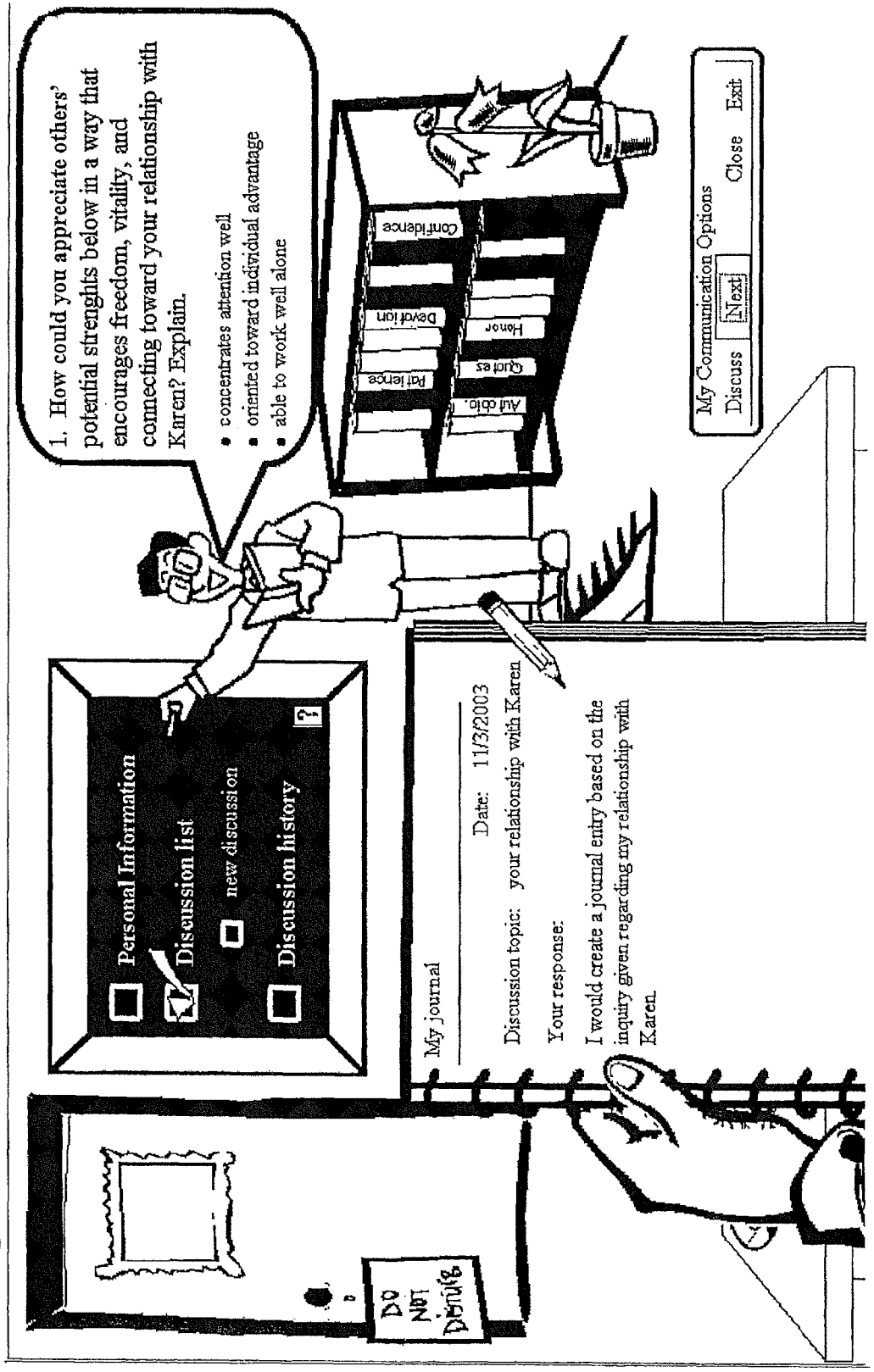
FIG. 53 shows a user interface wherein the user is presented with an inquiry for the fundamental category of "honor" for the discussion topic selected from FIG. 49 above and wherein the user may enter a journal entry or answer to the inquiry in the electronic journal.

[89] The user enters an explanation in their electronic journal shown in FIG. 53 based on the inquiry described in step 90 above. This explanation is stored in a data structure for later reporting. Refer to FIGS. 9, 15, 16, 19, 20, 21, 22, 23, 29, 30, and 31.

[90] A user may choose two different ways (FIG. 26 & FIG. 27) to report and review their discussion topics. Refer to FIGS. 24, 25, 26, 27, and 54.

[91] Report A (denoted as "view discussion report" herein from FIG. 26), reviews the discussion topic explanations (e.g., journal entries) for a given discussion topic. The user simply chooses a discussion topic in FIG. 54 (e.g., A) and a report is generated that provides the related inquiry and the related user explanation for each of the fundamental categories (A through D) for the given discussion topic. Refer to FIGS. 24, 25, 26, and 54.

[92] Report B, (denoted as "view category report" herein from FIG. 27), reviews the explanations for a given fundamental category within a date range for specified number of discussion topics in FIG. 54. In other words, a user may want to review all of their explanations for the fundamental category "confidence" for a range of discussions between Oct. 17, 2003 and Nov. 3, 2003. Refer to FIGS. 24, 25, 27, and 54.

Detailed Description of the Linguistic Constructs Table

This section is a detailed description of the Linguistic Constructs Table (refer to FIG. 29) in which the linguistic constructs or data for all the inquiries generated by the discussion generator are constructed. This table's design is based on the design of the Relationship Anatomy Model (see FIG. 30*a* through FIG. 30*f*) and captures the essential information necessary for generating inquiries from the DISCUSSION GENERATOR 5 component in FIG. 4 and for generating the autobiography statements necessary for the AUTOBIOGRAPHY DEVELOPER 25 component in FIG. 5. In general, the essential information or data that is captured for the Linguistic Constructs Table (processed in the LINGUISTICS ORGANIZER 17 component in FIG. 4) are the:

1. Fundamental categories derived from the FUNDAMENTAL CATEGORY CONSTRUCTOR 14 component which is conducted by the FACILITATOR 2 component in FIG. 1 (e.g., the facilitator).
2. Motivational Attributes from the MOTIVATIONAL ATTRIBUTE CONSTRUCTOR 10 component in FIG. 2 which are derived or predetermined from the USER PROFILE 9 component in FIG. 2 which is conducted by the USER 1 (e.g., the user) and may be modified by the FACILITATOR 2 component in FIG. 1 (e.g., the facilitator).
3. Motivational Coping Techniques from the MOTIVATIONAL COPING TECHNIQUE CONSTRUCTOR 15 component in FIG. 3 which is conducted by the FACILITATOR 2 component in FIG. 1 (e.g., the facilitator).
4. The user's sets of attitudinal trait descriptions (e.g., plenty of time for complex decisions—is a "need" description) are classified by the MOTIVATION EQUALIZER 11 component in FIG. 2 and the MOTIVATION AMPLIFIER 12 component in FIG. 2 and stored in appropriate data structures which represent each quadrant cache for each fundamental category (refer to FIG. 30*a*). These sets are identified in the Linguistic Constructs Table in FIG. 29 by unique names (e.g., A.1.1QCache1 in FIG. 29 under the label attitudinal trait description ID) which are "linked" to each set of attitudinal trait descriptions in FIG. 31.

First, referring to FIG. 29, the first two columns are labeled Fundamental Category and Motivational Attribute. The data defined in these columns are derived or predefined by the FACILITATOR 2 component in FIG. 1 (e.g., the facilitator) for the Fundamental Category and the USER PROFILE 9 component in FIG. 2 conducted by the USER 1 (e.g., the user) and may be modified by the FACILITATOR 2 component in FIG. 1 (e.g., the facilitator) for the Motivational Attribute. The Fundamental Category consists of four different categories referred to throughout one embodiment of this application (e.g., confidence, patience, devotion, and honor) which are defined by the FACILITATOR 2 component in FIG. 1 (e.g., the facilitator). The other column is labeled Motivational Attribute. As described in the Terms and Definitions section of this application, a motivational attribute is the source for developing or evolving a fundamental category. The motivational attributes (e.g., needs, stress reactions, interests, and strengths) consists of four different attributes referred to throughout one embodiment of this application which respectively correspond to each fundamental category (e.g., confidence, patience, devotion, and honor) which are defined by the USER PROFILE 9 component in FIG. 2 conducted by the USER 1 (e.g., the user) and may be modified by the FACILITATOR 2 component in FIG. 1 (e.g., the facilitator). You'll notice there are two sets of the four fundamental categories in the Linguistic Constructs Table. For example, "confidence" is listed four times (e.g., records 1 through 4) at the top of the table and then again listed four times (e.g., records 17 through 20) toward the bottom of the table. The same logic applies to the motivational attributes. The reason for this is somewhat complex and will be better described later in this description when referring to the Motivational Coping Technique label. Both the Fundamental Category and Motivational Attribute labels contain data which are not directly extracted for any inquiry generated by this system but serve only as information used to organize the remainder of the linguistic constructs or data described herein. For the purpose of simplifying the remainder of this description, refer to FIG. 29 and/or FIG. 30*a* through FIG. 30*f* when requested by this writer. The next column in FIG. 29 is called the State of Mind Location which identifies the "active" state of mind for a given fundamental category or inquiry (i.e., one inquiry is generated for each fundamental category and every fundamental category is represented for each discussion topic). Referring to FIG. 30*a*, the "active" state of mind will either be located on the "right" (e.g., Column 1) or "left" (e.g., Column 2) side of the model depending on how the user evaluates a discussion topic. The "active" state of mind reflects where the user's attention is mostly focused within each fundamental category when evaluating a given discussion topic. For example, if a user ranks the following true/untrue statement which supports the fundamental category "confidence", "I have 100% complete trust and faith regarding my relationship with Karen" (see FIG. 48), a 10 then the user is implying that their "needs" (e.g., motivational attribute for "confidence") are most likely being met in their relationship with Karen (e.g., discussion topic). Based on the response algorithm, Column 1 (e.g., which represents the user's "most like" attitudinal trait descriptions) will reflect a higher score than in Column 2. Therefore, Column 1 will represent the "active" state of mind location, or "ActiveRight". To better explain the linguistic constructs or data in the State of Mind Location column (e.g., "ActiveLeft" and "ActiveRight") please refer to FIG. 30*b*. Note that in FIG. 30*b*, quadrant 1 cache and quadrant 2 cache are indicative of column 1 (e.g., the "right" side of the Relationship Anatomy Model) and quadrant 3 cache and quadrant 4 cache are indicative of column 2 (e.g., the "left" side of the Relationship Anatomy Model). Also note that the response algorithm assigns a unique sub-rank to each of the four quadrant caches based on the rank provided by the user for each true/untrue statement which is designed based on each fundamental category when evaluating a given discussion topic (see FIG. 48). The "active" state of mind location will either exist on the "right" (e.g., column 1 or "ActiveRight") or "left" (e.g., Column 2 or "ActiveLeft") side of the model, but never both at once. The column which is not "Active" will represent the "Passive" state of mind. The side of the model which represents the "active" state of mind is dependent on how a user evaluates a given discussion topic in the DISCUSSION TOPIC EVALUATION 19 component in FIG. 4. The "active" state of mind is determined by adding the sub-ranks in each column from a previously evaluated discussion topic. The higher sub-ranked column will always represent the "active" (e.g., suggesting more effort) state of mind and the lower sub-ranked column will always represent the "passive" (e.g., suggesting less effort) state of mind. Therefore, "ActiveLeft" is indicative of the higher sub-ranked column being the "left" side, or being column 2. And "ActiveRight" is indicative of the higher sub-ranked column being the "right" side, or being column 1. In other words, column 2 is deemed to be "active" (e.g., "ActiveLeft") when the total sub-rank of quadrant 3 cache plus quadrant 4 cache is higher than when adding the total sub-rank of quadrant 1 cache plus quadrant 2 cache. Conversely, column 1 is deemed to be "active" (e.g., "ActiveRight") when the total sub-rank of quadrant 1 cache plus quadrant 2 cache is higher than when adding the total sub-rank of quadrant 3 cache plus quadrant 4 cache.

Next, the column labeled Begin Question incorporates two different descriptions indicative of "passive" and "active" state of mind inquiries. These descriptions are "Which" and "How" (NOTE: A "Which" description is derived from the word "What", which is believed to be a more "passive" (e.g., suggesting less effort) way of structuring "passive" state of mind inquiries). "Which" descriptions represent the "passive" state of mind inquiries and "How" descriptions represent the "active" (e.g., suggesting more effort) state of mind inquiries. A "Which" (e.g., "What") inquiry directs a user to create journal entries wherein the user initiates reflection and/or thought toward the discussion topic where no "action" is implied, but rather a thought or lesson of some sort. However, a "How" inquiry assumes that a user may want to create journal entries wherein the user initiates an action for the discussion topic. Note that when a "Which" inquiry is generated it will always refer to a "passive" state of mind. Conversely, when a "How" inquiry is generated it will always refer to an "active" state of mind. For example, in record #1 the begin question is "Which" and in the State of Mind column (described later in this section) for record #1, is identified as "passive".

Next, in FIG. 29, the column labeled Motivational Attribute Description describes the set of attitudinal trait descriptions (e.g., your needs) classified within a specific quadrant cache (e.g., A.1.1 shown in FIG. 31) for a specific fundamental category (e.g., confidence) and the corresponding motivational attribute (e.g., need). For example, in record #1, the data in the Motivational Attribute Description column reads, "your needs". This description represents the set of attitudinal trait descriptions for the quadrant 1 cache that represents a set of "need" attitudinal trait descriptions which are "most like" the user and where the user has previously (e.g., classified in the MOTIVATIONAL AMPLIFIER 12 component in FIG. 2) demonstrated or classified a "lower" awareness. In addition, to reflect this set of attitudinal trait descriptions for the fundamental category "confidence" the data in the column called Attitudinal Trait Description ID (described later in this section) are represented by the identifier in this column. For example, record #1 in the Attitudinal Trait Descriptions ID column shows the identifier "A.1.1 QCache 1". This identifier is linked to the set of attitudinal trait descriptions labeled A.1.1 in FIG. 31 for the fundamental category "confidence" and the corresponding motivational attribute "need". Therefore, when an inquiry requires the set of attitudinal trait descriptions from A.1.1 in FIG. 31 then this set is called from the identifier (e.g., A.1.1QCache 1) in the Linguistic Constructs Table in FIG. 29.

To gain even a greater understanding of how the data is designed in the column labeled Motivational Attribute Description, more explanation may be necessary. The set of attitudinal trait descriptions listed in "A.1.1" in FIG. 31, as described above, refer to the users "most like" needs in which the user has a lower awareness. As described above, the data which describes this set of attitudinal trait descriptions in the column Motivational Attribute Description in FIG. 29 is called "your needs". However, when the attitudinal traits description describes the users "most like" higher awareness needs, as in record #2, the description reads, "your most important needs" (e.g., a description which reflects a higher awareness of such attitudinal trait descriptions). This description implies (i.e., by the word "important") that the user has obtained a higher awareness of these needs through the MOTIVATION AMPLIFIER 11 component in FIG. 2. Conversely, a user's "least like" needs (i.e., Column 2) in which they have a lower awareness of reads (as indicated in record #3), "others potential needs". And the user's "least like" needs in which they have a higher awareness of reads (as indicated in record #4), "others potentially important needs". The descriptor "important" in the Motivational Attribute Description column is used to imply a higher awareness of the motivational attribute "needs" for the fundamental category "confidence". The descriptor "difficult" in the Motivational Attribute Description column is used to imply the higher awareness of the motivational attribute "stress reactions" for the fundamental category "patience". The descriptor "passionate" in the Motivational Attribute Description column is used to imply the higher awareness of the motivational attribute "interests" for the fundamental category "devotion". And the descriptor "consistent" in the Motivational Attribute Description column is used to imply the higher awareness of the motivational attribute "strengths" for the fundamental category "honor". In addition, for the users "least like" attitudinal trait descriptions the word "potential(ly)" is used to imply that others may or may not have these sets attitudinal trait descriptions in comparison to the user.

Next, for the column in the Linguistic Constructs Table labeled Auxiliary Verb, this column describes the user's ability or potential ability in addressing a set of attitudinal trait descriptions associated with an inquiry based on the user's discussion topic evaluation. For example, in record #1, the Auxiliary Verb description reads, "will you". The data "will you" (referring to "passive" state of mind inquiries suggesting less effort in response) and "can you" (referring to "active" state of mind inquiries suggesting more effort in response) are indicative of the user's "most like" Attitudinal Trait Descriptions (e.g., column 1 in FIG. 31). It is believed that "will" and "can" describe an ability in which the user is capable of expressing sets of attitudinal trait descriptions that are "most like" themselves. Conversely, "would you" (referring to "passive" state of mind inquiries suggesting less effort in response) and "could you" (referring to "active" state of mind inquiries suggesting more effort in response) are indicative of the user's "least like" sets of attitudinal trait descriptions (e.g., column 2 in FIG. 31). It is believed that "would" and "could" describe an ability in which the user may or may not be capable of or choose to express the set(s) of attitudinal trait descriptions that are "least like" themselves.

Next, for the column in the Linguistic Constructs Table labeled Motivational Coping Technique, this column describes the motivational coping technique to be used in the inquiry for the record being identified from the RESPONSE MANAGER 20 component in FIG. 4. Through experimentation and observation, it is believed that the motivational coping techniques, (e.g., Allow, Accept, Maintain, and Support for the fundamental category "confidence") aids the user in understanding a suggested way in dealing with the specific set of attitudinal trait descriptions for a motivational attribute (e.g., "needs") while assisting the user in developing and evolving the fundamental category for which the motivational coping techniques are designed (e.g., "Confidence"). The motivational coping techniques are designed according to the coping evolution requirements (refer to the Detailed Design Of The Coping Evolution Requirements). Furthermore, there are two ways to present inquiries for every motivational coping technique. For example, the motivational coping technique, "allow", may generate an inquiry that reflects one set of attitudinal trait descriptions that are "most like" the user (e.g., a set labeled A.1.1 in FIG. 31) or a different set of attitudinal trait descriptions that are "least like" the user (e.g., a set labeled A.2.3 in FIG. 31), but never both at one time for a given discussion topic evaluation for a given fundamental category. This difference is dependent on how the user evaluates a discussion topic in the discussion topic evaluation within the DISCUSSION TOPIC EVALUATION 19 component in FIG. 4. Therefore, the Linguistic Constructs Table is designed to generate two different inquiries for each motivational coping technique. In other words, a motivational coping technique (e.g., Allow) will represent one set of attitudinal trait descriptions when the data in the State of Mind Location column is deemed "ActiveLeft" (e.g., a set labeled A.1.1 in FIG. 31) and another set of attitudinal trait descriptions when the data in the State of Mind Location column is deemed "ActiveRight" (e.g., a set labeled A.2.3 in FIG. 31). However, as described in the Detailed Description Of The Invention in steps 32 through 64, the autobiography statements generated for the user's autobiography present both possible motivational coping techniques (e.g., "passive" and "active") for each set of attitudinal trait descriptions which doesn't require a user to perform a discussion topic evaluation. As the reader of this application appreciates the scope of this invention, the logic regarding the operation of the motivational coping techniques will become more clear.

Next, for the column in the Linguistic Constructs Table labeled State of Mind Description describes the label for the state of mind description required for the inquiry being generated. This label is used to identify the "passive" (e.g., suggesting less effort) or "active" (e.g., suggesting more effort) state of mind description. For example, if the record being identified is a "passive" state of mind (as in record #1) then the description identified as a "passive" state of mind (e.g., creativity, clarity, and satisfaction) will be identified and built into the inquiry being generated from the INQUIRY BUILDER 18 component in FIG. 4. Conversely, if the record being identified is an "active" state of mind (as in record #3) then the description identified as an "active" state of mind (e.g., freedom, vitality, and satisfaction) will be identified and built into the inquiry being generated from the INQUIRY BUILDER 18 component in FIG. 4.

Last, the column in the Linguistic Constructs Table labeled Attitudinal Trait Description ID describes the label for the set of attitudinal trait descriptions located in a specific quadrant cache (refer to FIG. 31) required for the inquiry being generated. For example, if the record being identified has a label of "A.1.1QCache 1" (as in record #1) then the set of attitudinal trait descriptions for the motivational attribute "need" and its corresponding fundamental category "confidence" will populate the inquiry being generated (refer to the set of attitudinal trait descriptions in FIG. 31 labeled A.1.1).

In conclusion, the linguistic constructs in the Linguistic Constructs Table are designed specifically to generate inquiries that support a user in gaining understanding, insight, and motivation toward empowering or improving any discussion topic and used to generate autobiography statements that aid the user in developing their autobiography. Overtime, the user will learn more about themselves and the situations or relationships in which they wish to investigate through a discussion topic evaluation.

The Detailed Description of the Coping Evolution Requirements

This section is a detailed description of the coping evolution requirements. Through experimentation and observation it is believed that the integrity of this invention depends on how accurate the facilitator/user defines the content of the relationship anatomy model according to the requirements discussed in this section. In order to better understand this section, please refer to the Relationship Anatomy Model in FIGS. 30a through 30f.

In general, the coping evolution requirements consist of defining motivational coping techniques for each fundamental category in a way which helps to communicate or evolve each such fundamental category. For one embodiment of this application, there are two sets (e.g., one "passive" and one "active" state of mind) of motivational coping techniques for each fundamental category. "Passive" motivational coping techniques are defined as verbs which could also be used as transitive verbs (e.g., transitive verbs express an action carried from the subject to the object; requiring a direct object to complete meaning) that elicit a passive-oriented (e.g., suggests less effort) response from the user. "Active" motivational coping techniques are defined as verbs which could also be used as transitive verbs as described previously that elicit an active-oriented (e.g., suggests more effort) response from the user. For example, an "accept" motivational coping technique is designed to elicit a passive-oriented response (e.g., suggesting less effort) from the user and a "support" motivational coping technique is designed to elicit an active-oriented response (e.g., suggesting more effort) from the user for the fundamental category "confidence".

Within each set of motivational coping techniques there is one "higher" and one "lower" awareness motivational coping technique. A "higher" awareness motivational coping technique is defined as an advanced-oriented (e.g., "accept" is believed to be more advanced than "allow") motivational coping technique. A "lower" awareness motivational coping technique is defined as a novice-oriented (e.g., allow is believed to be more novice than "accept") motivational coping technique. For example, an "accept" motivational coping technique is designed to illicit an advanced-oriented response from the user and an "allow" motivational coping technique is designed to illicit a novice-oriented motivational coping technique. In other words, through experimentation and observation, one would first "allow" (e.g., novice-oriented) an instance before "accept(ing)" (e.g., advanced-oriented) an instance.

The requirements described above apply to each set of motivational coping techniques within each fundamental category.

Descriptions of Other Embodiments

As stated in the Summary Of The Invention, other user profile's which use a binary scale to measure a plurality of different behaviors, attitudes, preferences, etc. within one or more attributes may also be designed to interface with this invention. In addition, combining the results of two or more profiles may also interface with this invention.

In additional embodiments, processes could be designed to utilize the user's feedback (e.g., journal entries) or other relevant data to enhance or evolve and existing user profile wherein the user's experience may be captured and re-generated. Moreover, task management tools may be developed into this invention or an interface may be designed to work with other, well known, task management products.

Also, this design allows for an infinite number of variables (e.g., state of mind) to be defined for each quadrant cache, therefore, video clips may also be generated which provide user's a visual experience of a particular motivational coping technique associated with a particular quadrant cache. For example, if a user is asked to "support" (e.g., a motivational coping technique for the fundamental category "confidence") another person's "need" (e.g., plenty of time for complex decisions) then a video could be generated that plays a presentation that shows someone "supporting" another person who has a need for "plenty of time for complex decisions".

Last but not least, this product may also be designed to work over the internet and in conjunction with other user's utilizing this same interface, so that, people may interface together to strengthen their working or personal relationships.

To provide necessary and sufficient written disclosure and enablement of the various embodiments of the present invention, the following reference is incorporated by reference in its entirety: U.S. Pat. No. 8,597,028 to Paul et al.

The foregoing discussion of the invention has been presented for purposes of illustration and description. Further, the description is not intended to limit the invention to the form disclosed herein. Consequently, variation and modification commiserate with the above teachings, within the skill and knowledge of the relevant art, are within the scope of the present invention. The embodiment described hereinabove is further intended to explain the best mode presently known of practicing the invention and to enable others skilled in the art to utilize the invention as such, or in other embodiments, and with the various modifications required by their particular application or uses of the invention.

What is claimed is:

1. A method for facilitating personal development using a computing device by providing non-transitory machine-readable instructions on a tangible medium to perform steps, comprising:
   for each user of a plurality of users, perform the following collections of steps (1) through (13) by employing a computational system operatively configured for entering into a dialog with each of a plurality of users:
   (1) obtaining and storing, via a computer of a computational system operatively configured for entering into a corresponding dialogue with each of the plurality of users, data for each of one or more predetermined user motivations, each motivation identified as a driver of user perceptions for the plurality of users, wherein the data includes a set of one or more words descriptive of each of the user motivations; wherein step (1) includes a step of receiving the data for each of the one or more predetermined user motivations, via a computer display of a computational system operatively configured for entering into a corresponding dialogue with each of a plurality of users;

(2) for each corresponding portion of the data for the user motivations, additional steps of obtaining and storing, through a computer display of the computational system operatively configured for entering into a corresponding dialogue with each of a plurality of users, a corresponding portion of personal description data for the user, the corresponding portion of the personal description data having a plurality of user specific descriptions, each of the user specific descriptions being both: (A) specific to the user, and descriptive of personal traits describing how to relate to a situation of concern, and (B) related to the corresponding portion of the data for the user motivations, and sufficiently meaningful to the user to assist the user in his/her personal growth and development when the user specific description is presented to the user as an example of the corresponding portion of the data for the user motivations;

grouping, for each corresponding portion of the data for the user motivations, the user specific descriptions in the user's corresponding portion of personal description data by a second computational component of the computational system operatively configured for entering into a corresponding dialogue with each of a plurality of users, wherein each of the user specific descriptions is grouped according to: (i) whether the user specific description is more characteristic of the user or less characteristic of the user, and (ii) whether the user is more aware of the user specific description being characteristic of the user or less aware of the user specific description being characteristic of the user, the resulting groups being as (2-a) through (2-c) following:

(2-a) a first group for one or more of the user specific descriptions, each such user specific description in the first group describing a corresponding personal attribute that is: (i) more characteristic of the user, and (ii) the user is more aware of the corresponding attribute being characteristic of the user, (2-b) a second group for one or more of the user specific descriptions, each such user specific description in the second group describing a corresponding personal attribute that is: (i) less characteristic of the user, and (ii) the user is more aware of the corresponding attribute, recited immediately above, being less characteristic of the user, and (2-c) a third group for one or more of the user specific descriptions, each such user specific description in the third group describing a corresponding personal attribute that is: (i) more characteristic of the user, and (ii) the user is less aware of the corresponding attribute, recited immediately above, being more characteristic of the user;

(3) obtaining and storing for each of the user motivations, data indicative of each of a plurality of coping techniques, each coping technique describing a technique for use by the user in relating to another person or situation, wherein for each coping technique, the data therefor identifies a corresponding second set of one or more words describing the coping technique, and for at least some of the coping techniques, their corresponding second set of words are different;

wherein a substep is performed of classifying the data indicative of the coping techniques into the following data classifications (3-a) through (3-c):

(3-a) a first data classification that includes the data for a first one or more of the coping techniques, wherein for each of the first one or more coping techniques, the data therefor is: (i) associated, in a step of associating, with each of the first and second groups, and (ii) associated with additional data that identifies the coping technique as initiating more activities to change how the user relates to issues involving another person or situation rather than meditatively reflecting on the issues;

(3-b) a second data classification that includes data for a second one or more of the coping techniques, wherein for each of the second one or more coping techniques, the data therefor is: (i) associated, in a step of associating, with each of the third and fourth groups, and (ii) associated with additional data that identifies the coping technique as initiating more activities to change how the user relates to the issues involving another person or situation rather than meditatively reflecting on the issues;

(3-c) a third data classification that includes data for a third one or more of the coping techniques, wherein for each of the third one or more coping techniques, the data therefor is: (i) associated, in a step of associating, with each of the first and second groups, and (ii) associated with additional data that identifies the coping technique as monitoring and evaluating how the user relates to the issues involving another person or situation rather than initiating activities to change how the user relates to the issues;

(4) obtaining, via a computational system operatively configured for entering into a corresponding dialogue with each of a plurality of users, input for a topic identifying a target of concern to the user;

performing for each one of the user motivations the following collections of step (5) through (13):

(5) outputting to the user a request for the user to input an evaluation as to how the user relates to the target of concern relative to the one user motivation; wherein the step of outputting includes a step of presenting topic related data to the user via a computer display of the a computational system operatively configured for entering into a corresponding dialogue with each of a plurality of users to assist the user in his or her personal growth and development;

(6) receiving, via a computational system operatively configured for entering into a corresponding dialogue with each of a plurality of users, the evaluation indicative of the user's perception as to how the user relates to the target of concern, and a degree of confidence the user has in the evaluation;

(7) ranking, by a computational system operatively configured for entering into a corresponding dialogue with each of a plurality of users, the first, second, and third groups of user specific descriptions, for the one user motivation, using the evaluation and the degree of confidence, wherein the ranking assigns a ranking value for each of the first, second, and third groups, wherein for each of the groups the ranking value therefor is indicative of how well the user specific descriptions of the group in each of the first, second, and third groups relate to the user's perspective of the target of concern for assisting the user in his/her personal growth and development;
wherein the step of ranking is performed in response to an input to a computer display of the computational system;
(8) determining a primary one of the coping techniques for the one user motivation by the substeps (8-a) and (8-b):
(8-a) obtaining a plurality of assignments, for each of the first, second, and third data classifications for the one user motivation, one of the assignments being a pairing of: (i) the data for one of the coping techniques for the data classification, with (ii) a selected one of the associated groups for the one coping technique, wherein the selection is dependent upon ranking values; and
(8-b) selecting the primary coping technique as the coping technique wherein the data therefor is paired with a particular one of the first, second, and third groups, wherein the particular group is determined according to a result of a predetermined function of the ranking values;
(9) generating, based on the ranking, via a computational system operatively configured for entering into a corresponding dialogue with each of a plurality of users, a responsive presentation to the user in a non-transitory form that provides the user with topic related information to assist the user in his or her personal growth and development, the generating step including providing a presentation generator for generating presentations for interacting with a user and providing textual descriptions organized so that outputs to the user are generated from various personality/motivational perspectives, the responsive presentation including:
(9a) the set of one or more words descriptive of the one user motivation;
(10) electronically outputting the responsive presentation to the user as a computer display;
(11) electronically receiving a responsive user input inputted into a computer display of a computational system operatively configured for entering into a corresponding dialogue with each of a plurality of users, wherein the responsive user input is a response to the responsive presentation to the user;
(12) displaying the input for a topic identifying a target of concern to the user;
(13) storing, in non-transitory computer storage, linked data including: the responsive presentation, and the responsive user input, wherein the responsive presentation and the responsive user input are linked together for electronic access by a computational system operatively configured for entering into a corresponding dialogue with each of a plurality of users;
wherein the stored linked data is available for outputting the responsive presentation, and the responsive user input for assisting the user with his/her personal growth and development; and linking each user to an audio file, said audio file comprising a visualization exercise;
wherein said one or more predetermined user motivations include an attitudinal trait description;
wherein said attitudinal trait description represents how a user most likely behaves or least likely behaves and wherein the attitudinal trait description is consistent with a user profile; and
wherein said attitudinal trait description comprises a user's likely behavior.

* * * * *